(12) United States Patent
Rummery et al.

(10) Patent No.: US 8,636,007 B2
(45) Date of Patent: Jan. 28, 2014

(54) PATIENT INTERFACE SYSTEMS

(75) Inventors: Gerard Michael Rummery, Woodford (AU); Robert Edward Henry, Baulkham Hills (AU); Phoebe Katherine Hill, Neutral Bay (AU); Andrew Hurst, Illawong (AU); Fiona Catherine Carroll, Concord (AU)

(73) Assignee: ResMed Limited, Bella Vista (AU)

( * ) Notice: Subject to any disclaimer, the term of this patent is extended or adjusted under 35 U.S.C. 154(b) by 691 days.

(21) Appl. No.: 12/738,671

(22) PCT Filed: Oct. 22, 2008

(86) PCT No.: PCT/AU2008/001557
§ 371 (c)(1),
(2), (4) Date: Apr. 19, 2010

(87) PCT Pub. No.: WO2009/052560
PCT Pub. Date: Apr. 30, 2009

(65) Prior Publication Data
US 2010/0307502 A1    Dec. 9, 2010

Related U.S. Application Data

(60) Provisional application No. 61/031,173, filed on Feb. 25, 2008, provisional application No. 61/129,982, filed on Aug. 4, 2008.

(30) Foreign Application Priority Data

Oct. 22, 2007  (AU) ................................ 2007905737
Nov. 16, 2007  (AU) ................................ 2007906276

(51) Int. Cl.
*A61M 15/08*  (2006.01)
*A61M 16/06*  (2006.01)

(52) U.S. Cl.
USPC ............ 128/207.13; 128/207.18; 128/206.21; 128/200.26; 128/200.24

(58) Field of Classification Search
USPC ............ 128/200.24, 200.26, 203.22, 206.21, 128/207.13, 207.18
See application file for complete search history.

(56) References Cited

U.S. PATENT DOCUMENTS 3,013,556 A * 12/1961 Galleher, Jr. ............. 128/207.11
4,378,795 A *  4/1983 Feathers et al. .......... 128/202.27

(Continued)

FOREIGN PATENT DOCUMENTS

GB    2 200 281 A    8/1988
GB    2 385 533      8/2003

(Continued)

OTHER PUBLICATIONS

International Search Report mailed Jan. 6, 2009 in PCT/AU2008/001557.

(Continued)

*Primary Examiner* — Annette Dixon
(74) *Attorney, Agent, or Firm* — Nixon & Vanderhye P.C.

(57) ABSTRACT

A patient interface system for delivery of a supply of air at positive pressure to the entrance of a patient's airways for treatment of sleep disordered breathing includes an air delivery tube connected to a flexible portion of a plenum; a vent structure having sufficient rigidity to support its own weight under gravity and/or not to block or fold under tube movement or tube drag; and a patient interface structure. The patient interface structure includes a seal forming structure arranged on a top portion of the plenum; and a seal positioning and stabilizing structure connected to a flexible portion of the plenum. The seal-forming structure is substantially decoupled from a tube drag force.

64 Claims, 79 Drawing Sheets

(56) References Cited

U.S. PATENT DOCUMENTS

| | | | |
|---|---|---|---|
| 4,971,051 A | 11/1990 | Toffolon | |
| 5,042,478 A * | 8/1991 | Kopala et al. | 128/207.18 |
| 5,074,297 A | 12/1991 | Venegas | |
| 5,117,818 A * | 6/1992 | Palfy | 128/204.11 |
| 5,181,507 A * | 1/1993 | Michel et al. | 128/201.25 |
| 5,481,763 A * | 1/1996 | Brostrom et al. | 2/452 |
| 5,724,965 A * | 3/1998 | Handke et al. | 128/207.13 |
| 6,039,044 A | 3/2000 | Sullivan | |
| 6,119,694 A * | 9/2000 | Correa et al. | 128/207.13 |
| 6,192,886 B1 * | 2/2001 | Rudolph | 128/207.13 |
| 6,418,928 B1 | 7/2002 | Bordewick et al. | |
| 6,431,172 B1 * | 8/2002 | Bordewick | 128/207.18 |
| 6,595,214 B1 | 7/2003 | Hecker et al. | |
| 6,631,718 B1 | 10/2003 | Lovell | |
| 7,201,169 B2 * | 4/2007 | Wilkie et al. | 128/207.18 |
| 7,261,105 B2 * | 8/2007 | Fukunaga et al. | 128/204.18 |
| 2005/0205096 A1 * | 9/2005 | Matula et al. | 128/207.11 |
| 2006/0042629 A1 | 3/2006 | Geist | |
| 2006/0081250 A1 | 4/2006 | Bordewick et al. | |
| 2006/0201514 A1 * | 9/2006 | Jones et al. | 128/206.21 |
| 2006/0254593 A1 | 11/2006 | Chang | |
| 2006/0260614 A1 | 11/2006 | Biener et al. | |
| 2007/0137653 A1 | 6/2007 | Wood | |
| 2007/0251522 A1 * | 11/2007 | Welchel et al. | 128/201.15 |
| 2008/0196727 A1 * | 8/2008 | Ho et al. | 128/207.11 |
| 2009/0044808 A1 | 2/2009 | Guney et al. | |
| 2009/0050156 A1 | 2/2009 | Ng et al. | |

FOREIGN PATENT DOCUMENTS

| | | |
|---|---|---|
| JP | H09-10311 | 1/1997 |
| JP | 2000-325481 | 11/2000 |
| JP | 2002-28240 | 1/2002 |
| JP | 2003-512902 | 4/2003 |
| JP | 2007-516749 | 6/2007 |
| WO | WO 96/17643 | 6/1996 |
| WO | WO 01/32250 | 5/2001 |
| WO | WO 2005/063326 A1 | 7/2005 |
| WO | WO 2005/086943 A2 | 9/2005 |
| WO | WO 2006/074516 A1 | 7/2006 |
| WO | WO 2006/130903 | 12/2006 |
| WO | WO 2007/064665 | 6/2007 |
| WO | WO 2007/131267 A1 | 11/2007 |
| WO | WO 2009/052560 A1 | 4/2009 |

OTHER PUBLICATIONS

International Preliminary Report on Patentability mailed Dec. 1, 2009 in PCT/AU2008/001557.

Examination Report Mailed Aug. 11, 2011 in New Zealand Appln. No. 584110 (2 pages).

Examination Report mailed Aug. 11, 2011 in New Zealand Application No. 584110 (2 pages).

Examination Report mailed Oct. 5, 2011 in New Zealand Application No. 584110 (1 page).

Extended European Search Report issued in a corresponding EP Application No. 08841391.9, dated Feb. 12, 2013.

Japanese Notice of Reasons for Rejection w/English translation dated Feb. 12, 2013 in corresponding Japanese Patent Application No. 2010-530222 (10 pages total).

Office Action issued in a corresponding Chinese Patent Application No. 200880112819.X with English translation thereof (Apr. 16, 2013).

* cited by examiner

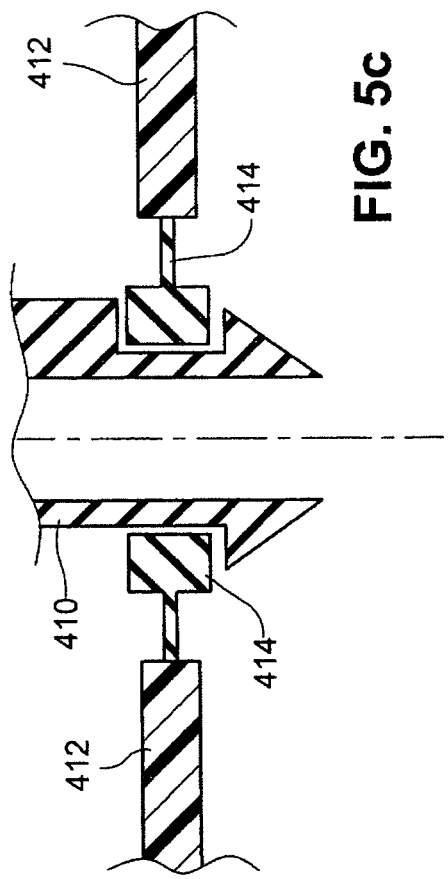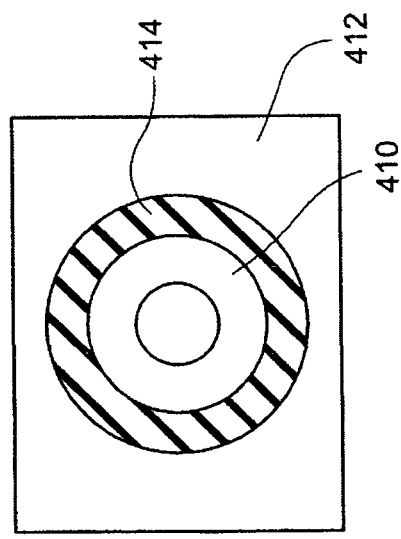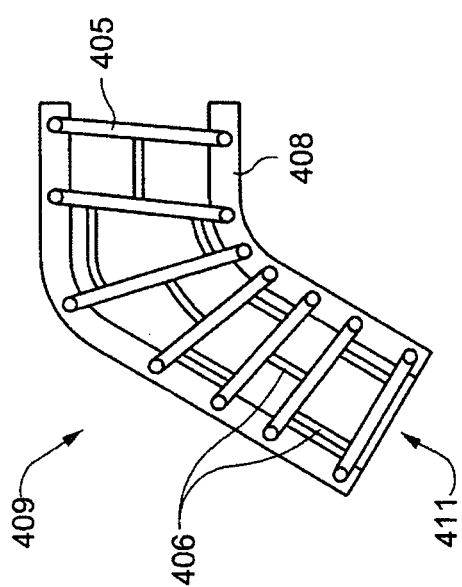

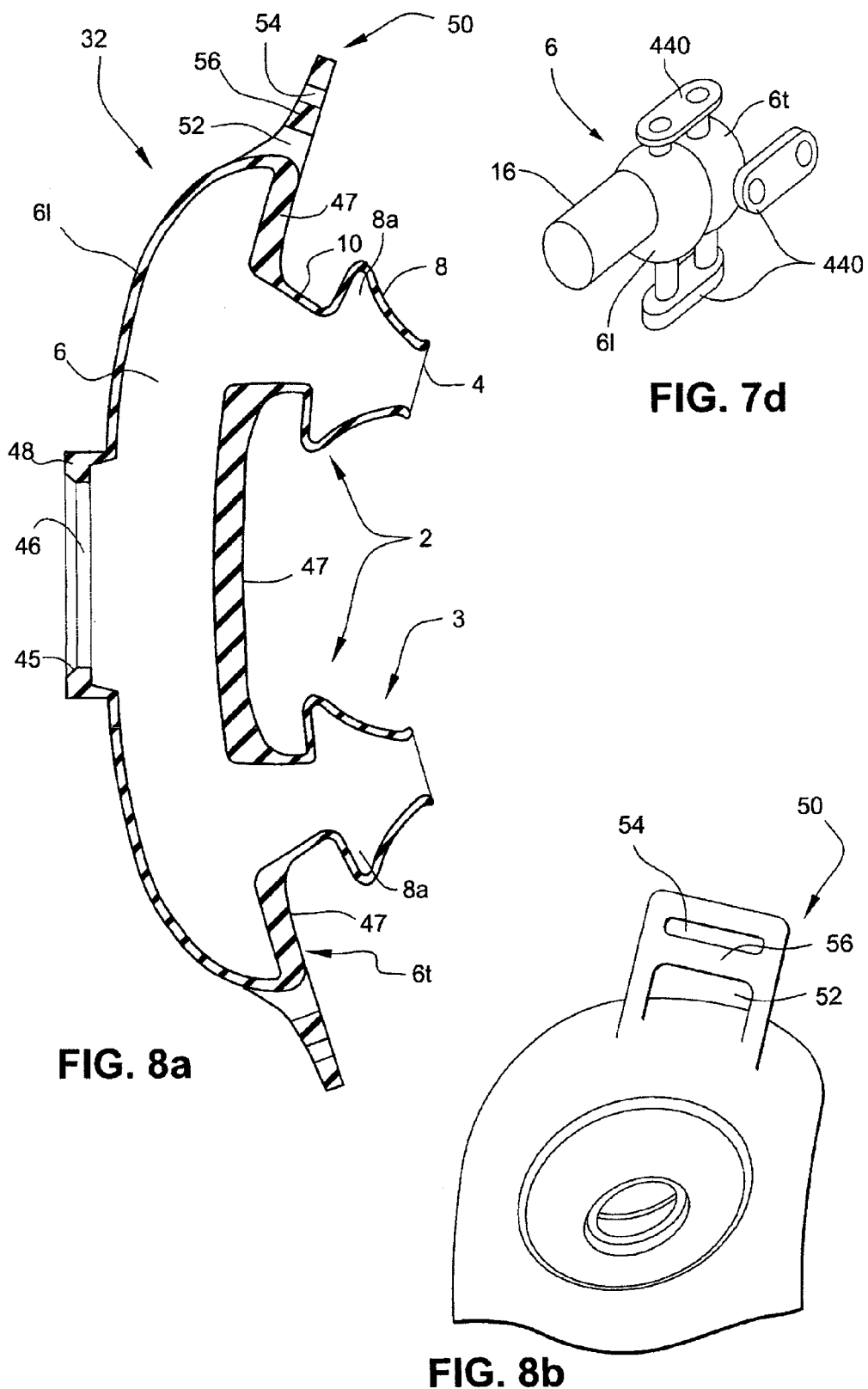

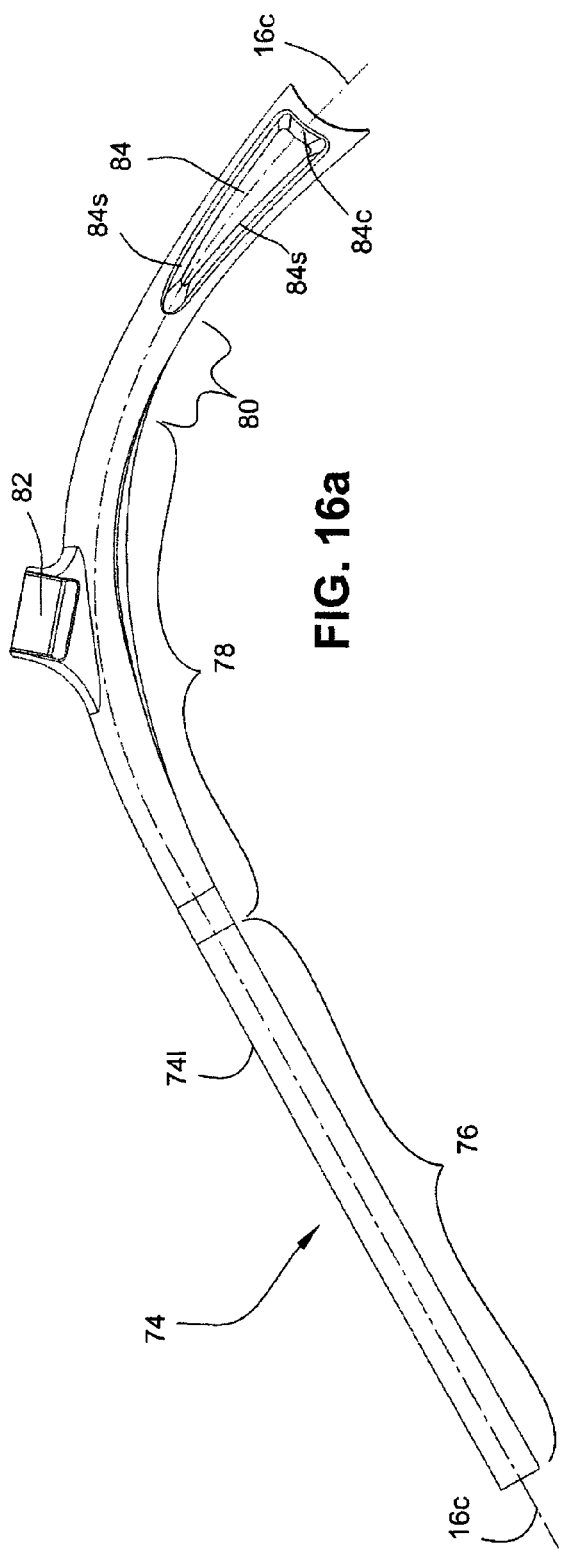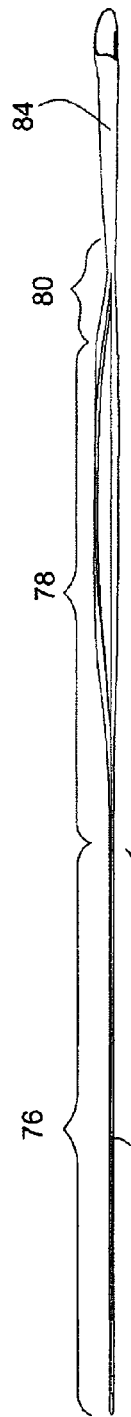

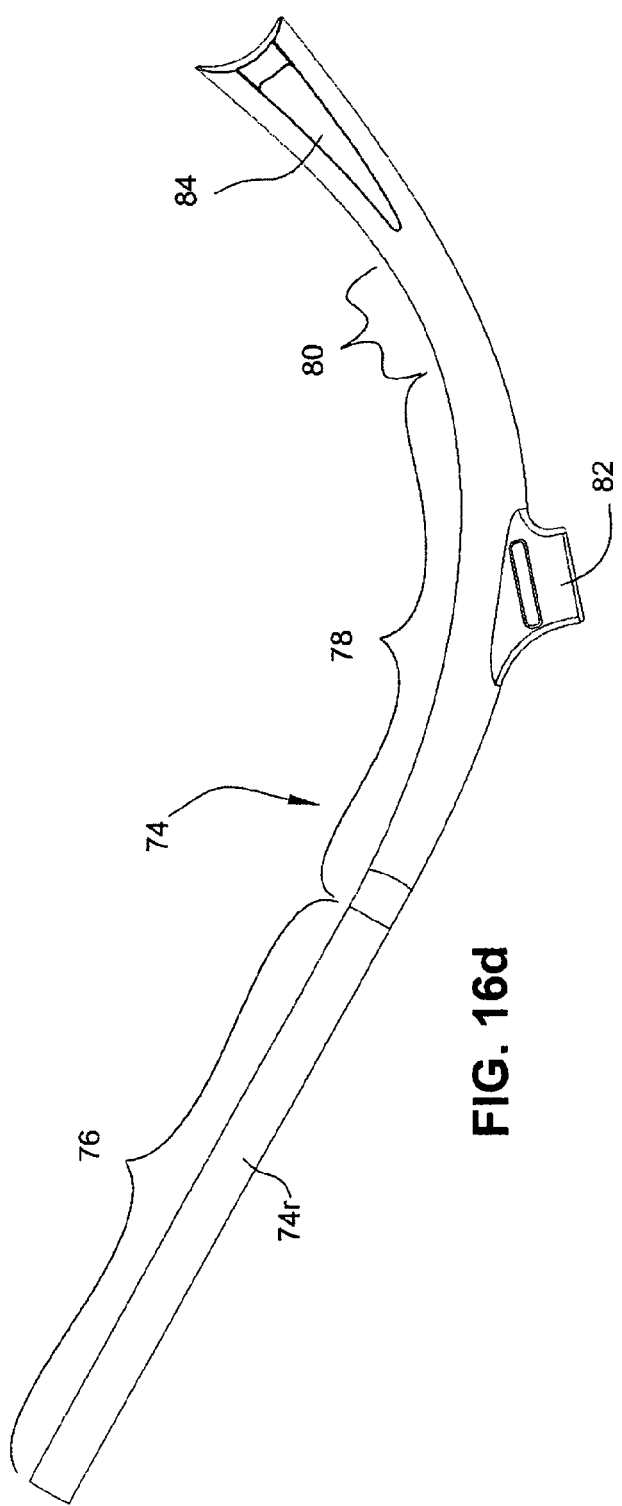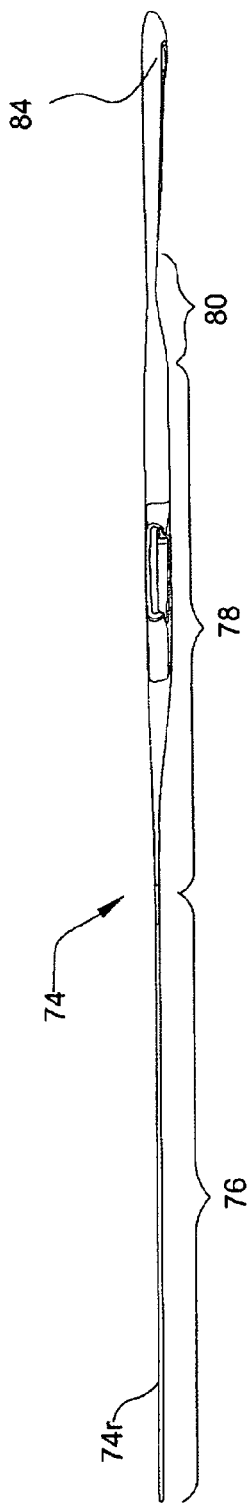
FIG. 16d
FIG. 16e

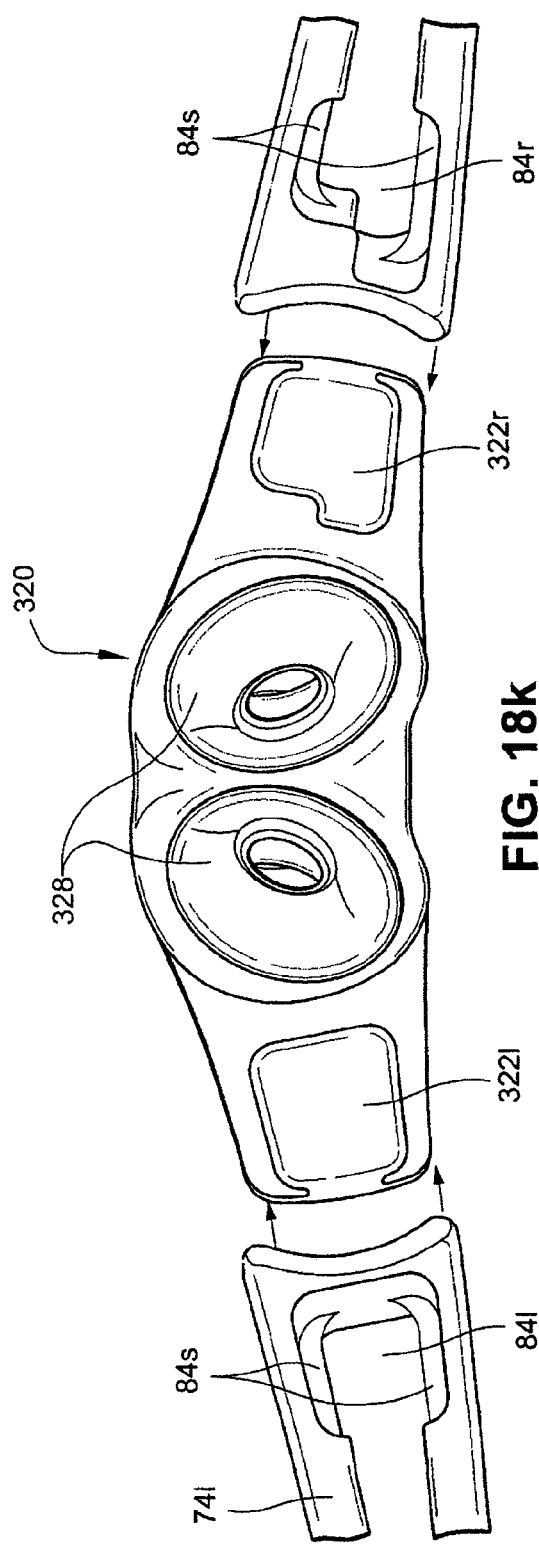
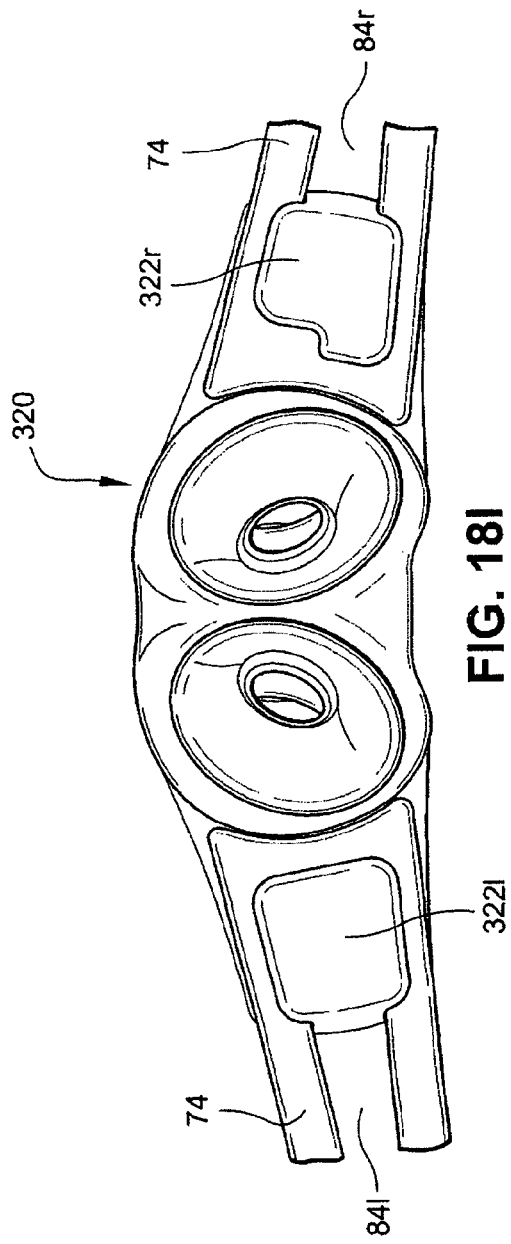
FIG. 18k
FIG. 18l

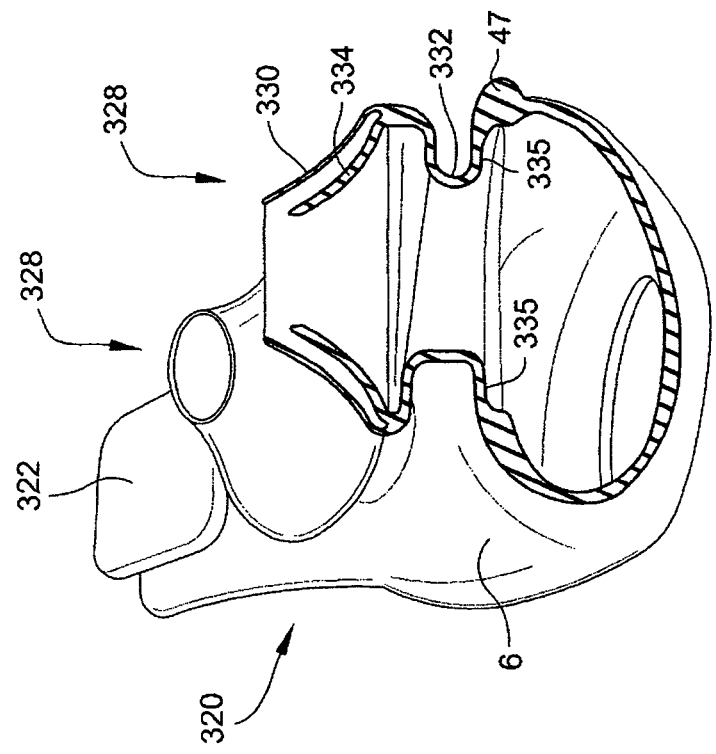
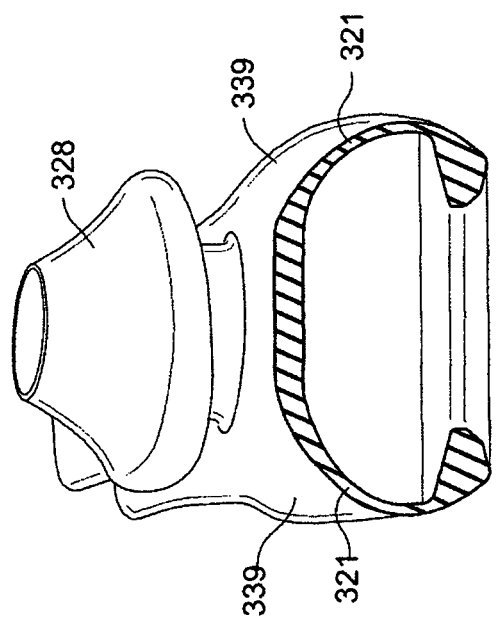
FIG. 18s
FIG. 18r

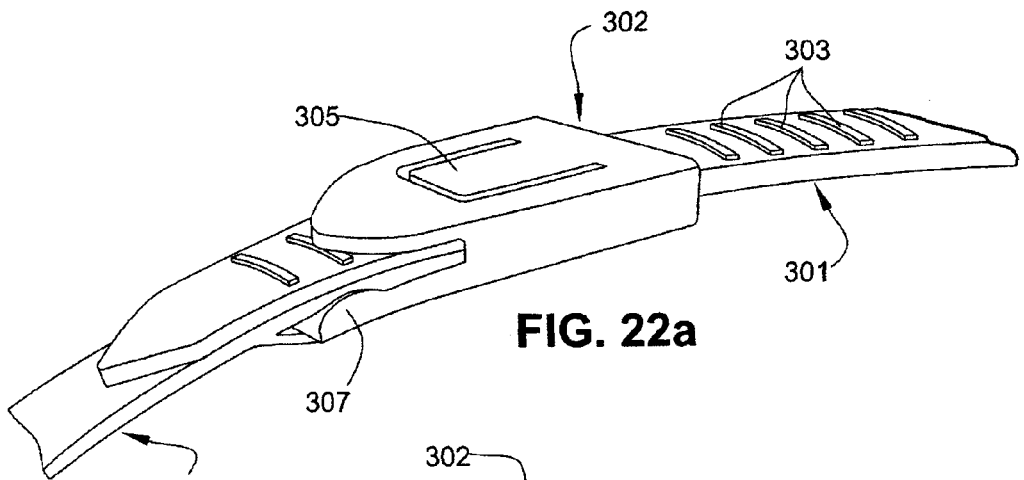
FIG. 22a
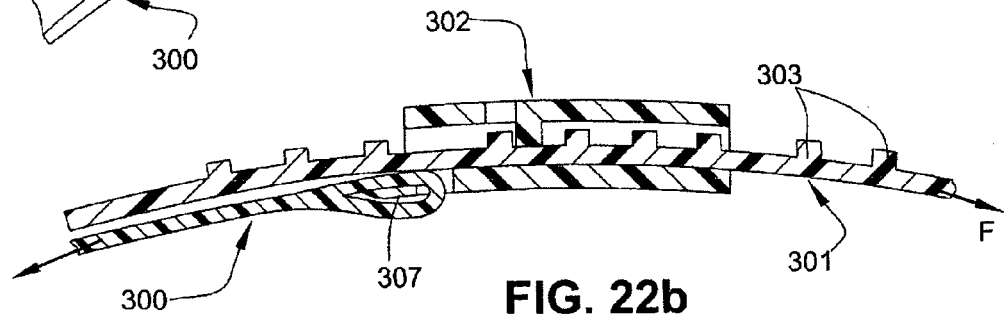
FIG. 22b
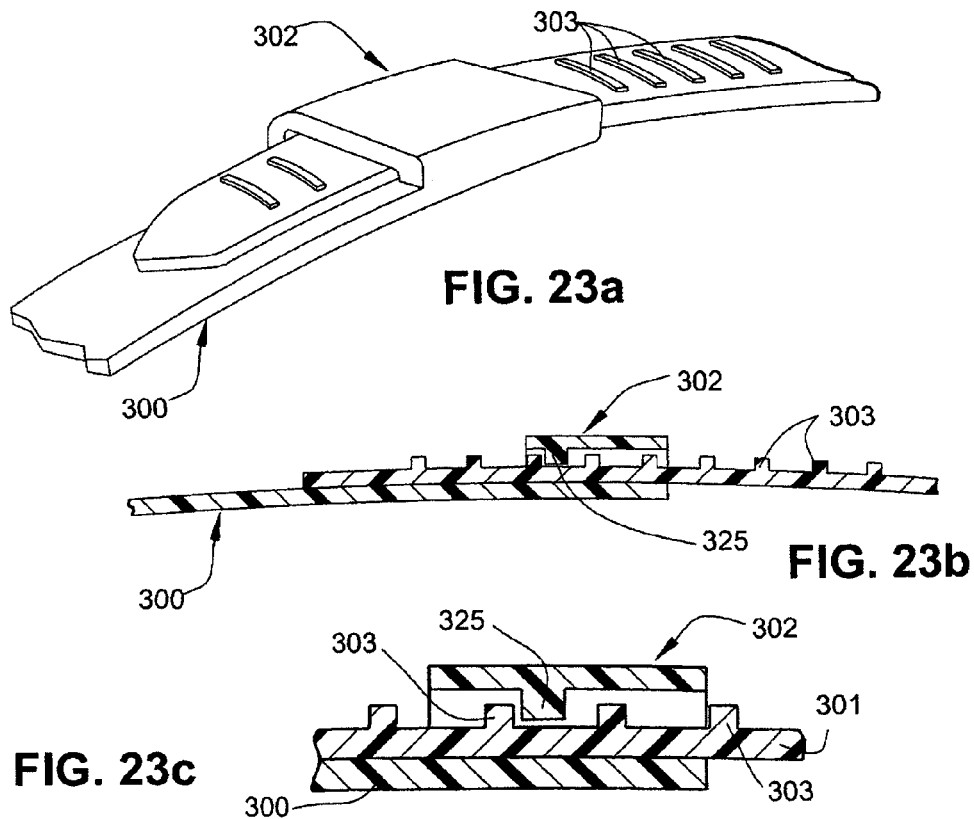
FIG. 23a
FIG. 23b
FIG. 23c

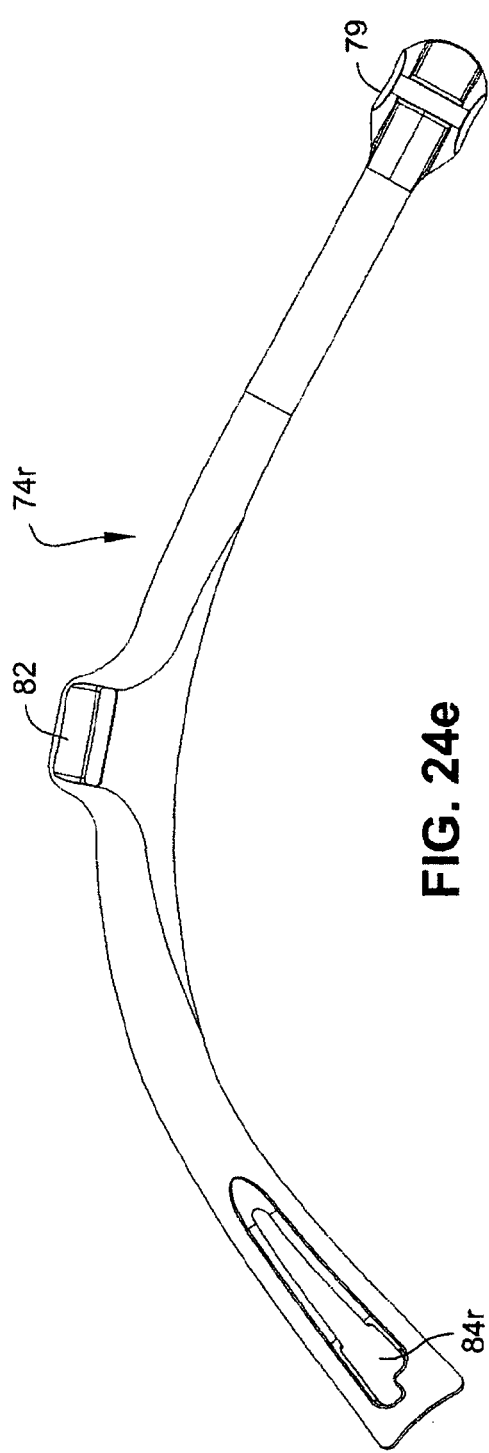
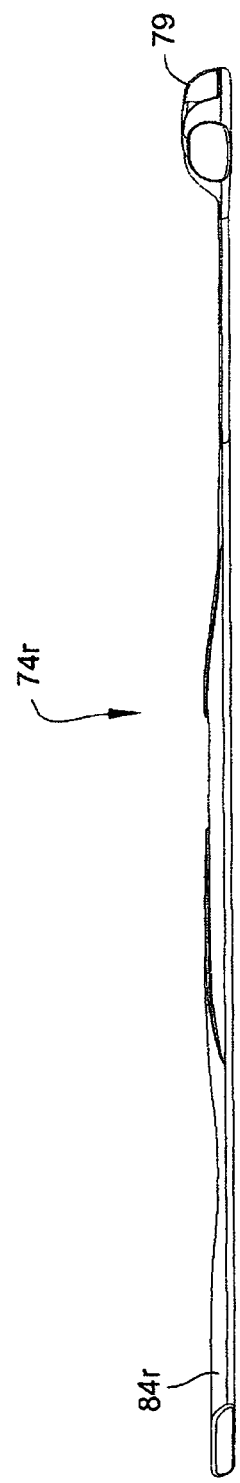
FIG. 24e
FIG. 24f

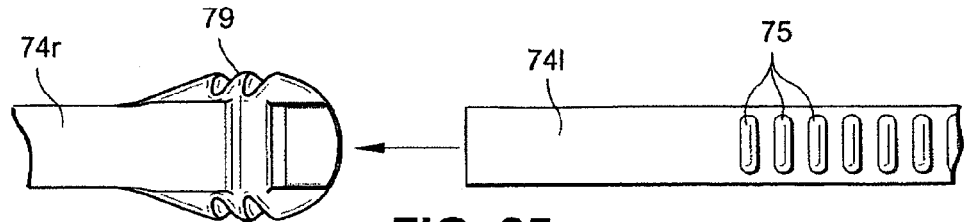
FIG. 25a
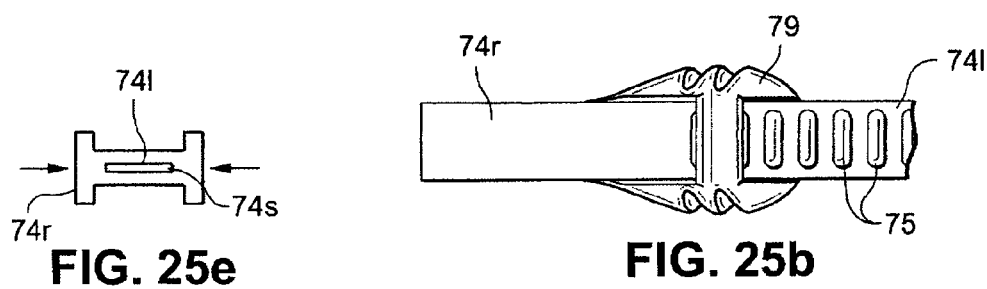
FIG. 25e  FIG. 25b
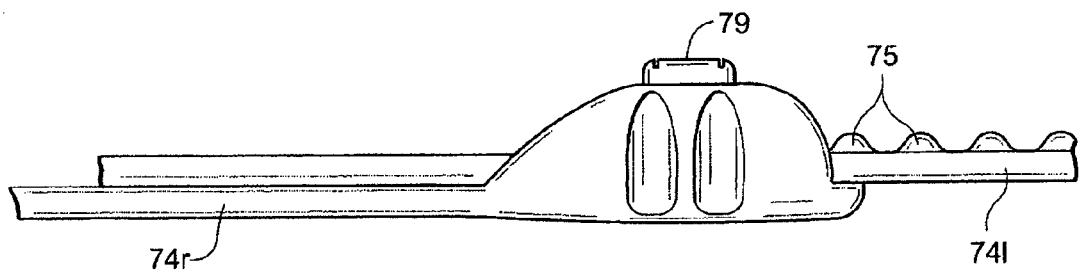
FIG. 25c
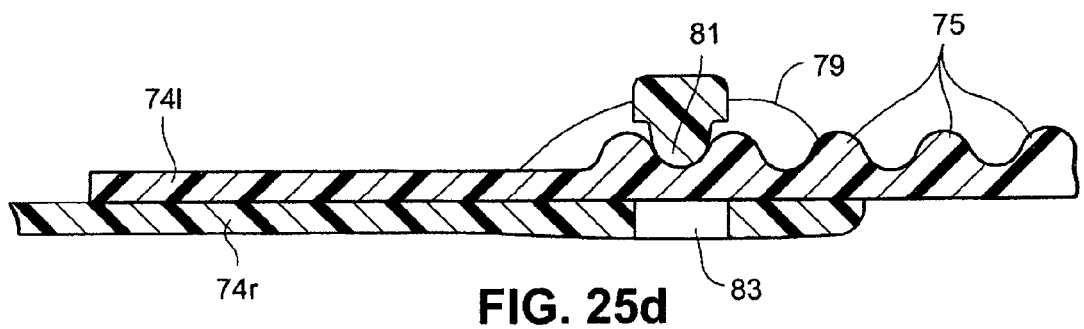
FIG. 25d
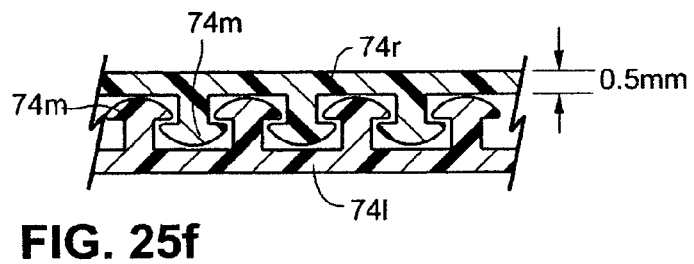
FIG. 25f

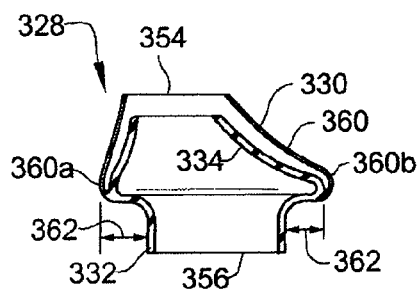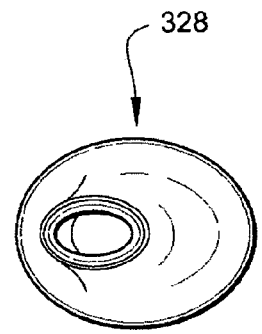
FIG. 28a   FIG. 28b
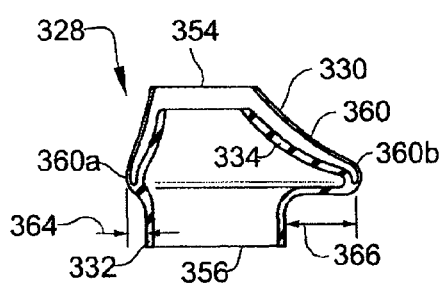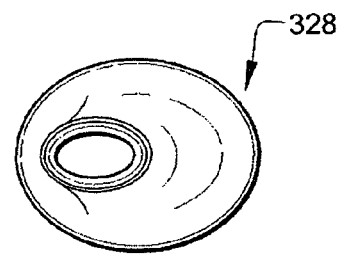
FIG. 29a   FIG. 29b
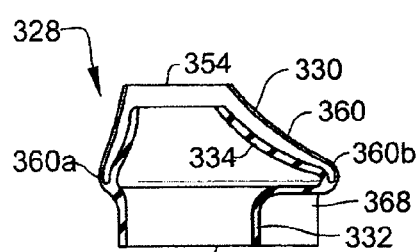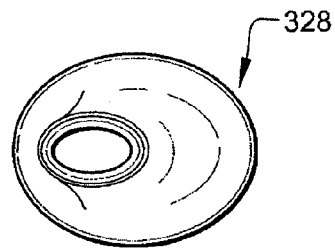
FIG. 30a   FIG. 30b
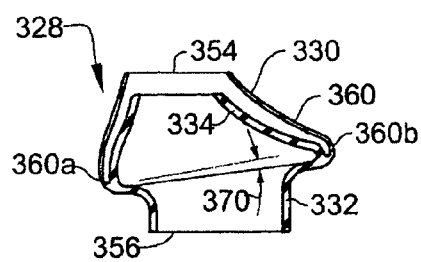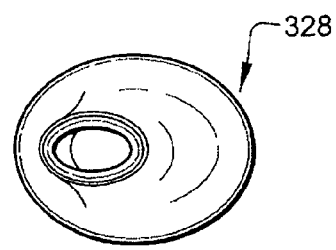
FIG. 31a   FIG. 31b

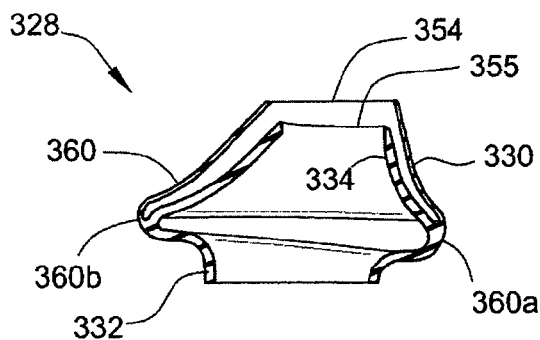 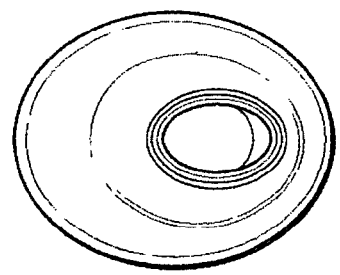
FIG. 33a    FIG. 33b
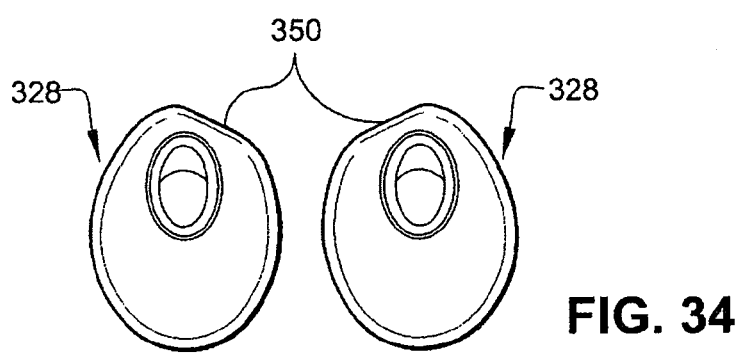
FIG. 34
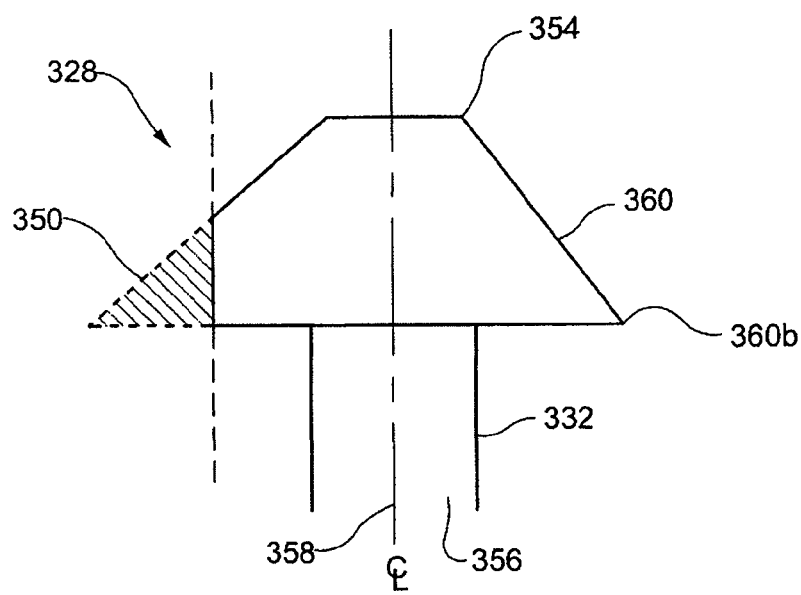
FIG. 35

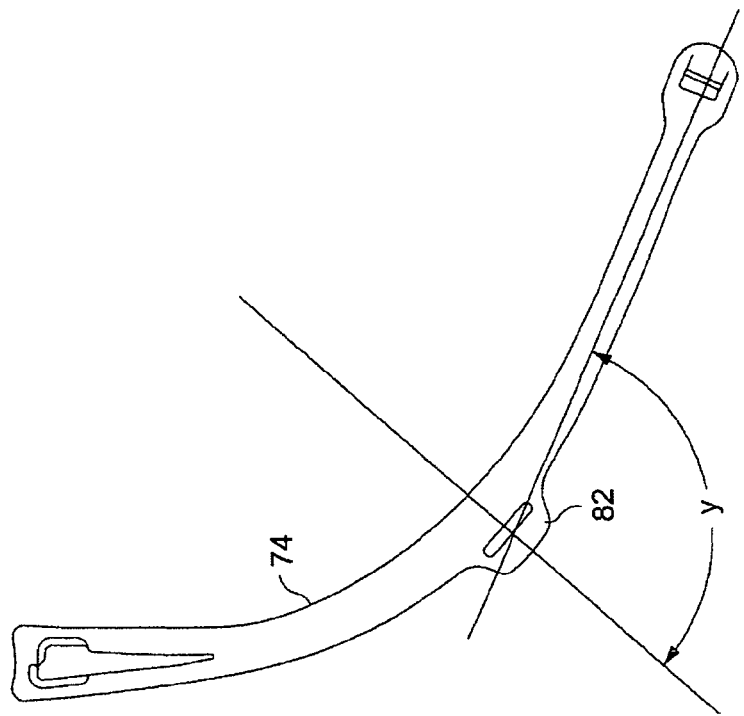
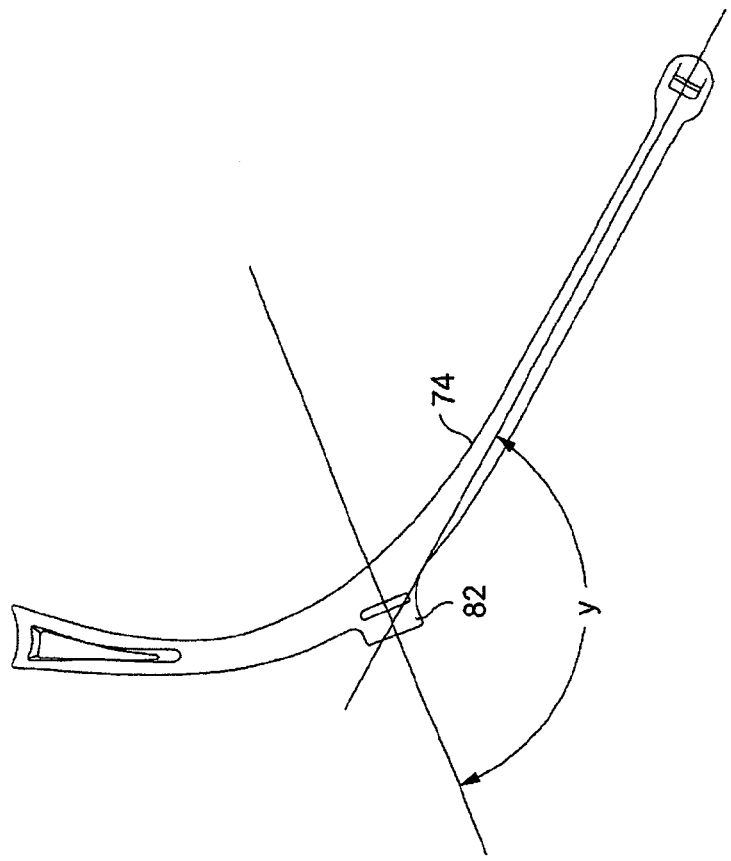

PATIENT INTERFACE SYSTEMS

CROSS REFERENCE TO RELATED APPLICATIONS

This application is the U.S. national phase of International Application No. PCT/AU2008/001557 filed Oct. 22, 2008 which designated the U.S. and claims priority to Australian Applications 2007905737 and 2007906276, filed Oct. 22, 2007 and Nov. 16, 2007, respectively, and U.S. Applications 61/031,173 and 61/129,982, filed Feb. 25, 2008 and Aug. 4, 2008, respectively, the entire contents of each being incorporated herein by reference.

FIELD OF THE INVENTIONS

The inventions relate to patient interfaces for delivery of respiratory therapy to a patient. Examples of such therapies include Continuous Positive Airway Pressure (CPAP), Non-Invasive Positive Pressure Ventilation (NIPPV), and Variable Positive Airway Pressure (VPAP). The therapy is used for treatment of various respiratory conditions including Sleep Disordered Breathing (SDB), for example Obstructive Sleep Apnea (OSA).

BACKGROUND OF THE INVENTIONS

1. Introduction

The provision of a supply of air at positive pressure to the entrance of a patient's airways for treatment of SDB was first disclosed in U.S. Pat. No. 4,944,310 to Sullivan. The delivery of the pressurized flow is facilitated by a patient interface, such as a mask. Mask systems may be classified as "nasal masks," "full-face masks," "nose and mouth masks" and a variety of nozzle designs, including "nasal pillows," "nasal puffs," "nasal prongs" and "nasal cannulae" designs. An example of a nasal pillow-type mask system is disclosed in WO 2004/073778 (Gunaratnam et al.), the contents of which are hereby incorporated by reference.

While different manufacturers use different terminology to refer to different components, patient interfaces systems, also called mask systems, typically comprise:

(i) a cushioning element
(ii) a headgear system to position and retain the cushioning element in position;
(iii) a rigid structure, known as a frame or shell; and
(iv) an air delivery tube.

Cushioning Element

The cushioning element, or cushion, generally includes a soft, conforming structure made from a material such as a silicone, a gel, or a foam. In use the cushion is held against the appropriate part of the face to effect a seal. The cushioning element should form an adequate seal with the entrance to the airways in order to maintain sufficient air pressure for splinting open the airways. In some cases it may not be necessary to form a complete seal provided an adequate supply of air can be provided at appropriate pressures and flow rates for effective therapy.

Nasal pillows and nasal puffs form a seal on the outside of the nares, whereas nasal prongs and nasal cannulae are positioned further into the nares and may form a seal on an inside surface of a nare, rather than an outside surface. The location of the seal is a consideration because different surfaces have different orientations, meaning that the force vector needed to form a seal may have a different direction. This may result in a headgear that is appropriate for one design being inappropriate for another. Furthermore, different seal types may be preferred by different patients, and may be regarded as being more comfortable by some patients.

Headgear System

A mask system typically further comprises a range of frame and headgear systems intended to provide force vectors of appropriate magnitude and direction to hold the cushion in place.

Frame

Many mask systems include a rigid, or semi-rigid, structure referred to as a shell or frame. Together the cushioning element and the frame may define a chamber. Typically, the cushion, headgear and an air delivery tube are attached to the frame. The frame serves as an anchoring point for the cushion, headgear and tube. Past efforts in mask design have been directed towards mechanisms for anchoring the frame in a fixed position with respect to the face and then attaching the cushion to the frame to form a seal.

Tube

Many mask systems require some form of tube, hose, or conduit to deliver the flow of air to the mask for breathing by the patient. In use, tube drag forces can disrupt the effectiveness of the seal. This can be the result of the weight of the tube and/or movement of the patient. While tube drag can be alleviated to some extent by the use of swivels, ball and socket joints, and tube anchoring arrangements, many patients feel the need to over-tighten headgear straps in an attempt to reduce the problem, leading to discomfort.

2. Prior Art

Design of an effective respiratory mask system requires consideration of many factors. Apparently subtle changes may improve or decrease comfort or effectiveness.

While millions of people suffer from the condition of sleep disordered breathing, many fail to comply with therapy because of problems with comfort, ease of use, stability, leak, and obtrusiveness, and thus expose themselves to health risks.

Some prior art mask systems attempt to anchor a rigid frame in a fixed position with respect to the face and require patients to increase headgear tension to a level sufficiently high to overcome the seal disruptive effects of patient movement, and/or tube drag.

Whilst some smaller patient interfaces (such as some nasal puffs, and some nasal prongs) may be less obtrusive than larger masks (such as a full-face mask) they can suffer from a lack of stability. Interface stability of such smaller interfaces was improved by holding the frame in a fixed position in front and below the patient's nares. The cushion, including the nozzles, extends from this frame to the nares. The frame was held in a rigid fashion (i.e. a set location) aiming to ensure correct alignment of the pillows.

Some prior art patient interfaces included swivel elbows or ball-and-socket joints.

Some headgear designs incorporated semi-rigid elements that increased stability of the mask frame. Some frames were designed having a horizontally central tube attachment point.

Some prior patient interfaces have required patients to increase headgear tension forces to a high level in an attempt to overcome disruptive forces. This can lead to excessive forces on sensitive regions of the face, resulting in discomfort to the patient.

Referring to FIG. 1, a prior art respiratory mask system may include a cushion 24 comprising, for example, nasal pillows. The cushion 24 is supported on a rigid frame or shell 18 and a flexible component 22, for example a gusset, is provided between the cushion 24 and the frame 18. An air delivery hose or tube 16 is connected to the frame 18 for the delivery of the flow of pressurized breathable gas. A rigid headgear 20 is connected to the frame 18 to maintain the cushion 24 in sealing contact with the nose of the patient 1.

Cushions which may be used in such a prior art respiratory mask system as shown in FIG. 1 include those disclosed, for example, in ResMed Ltd.'s Swift® LT.

FIG. 2 schematically illustrates another respiratory mask system according to the prior art, the Fisher & Paykel Infinity® 481 mask. A cushion 24 comprising nasal prongs 23 is attached to a mask frame or shell 18. The mask frame includes headgear connectors 26 provided on sides of the mask frame 18. A vent including a plurality of vent holes 28 is also provided in the mask frame 18.

The mask frame 18 is connected to an air delivery hose or tube 16 by a swivel elbow 17. The air delivery tube 16 is connected to a flow of pressurized breathable gas, such as generated by a blower or flow generator, by a coupling element 30.

As the headgear is connected to the mask frame 18 by the headgear connectors 26, any relative movement between the mask frame 18 and the patient's face may result in a disruption of any seal that may have formed.

SUMMARY OF THE INVENTION

One aspect relates to providing comfortable, stable, effective, unobtrusive patient interface systems for delivering a supply of air at positive pressure to the entrance of a patient's airways. Another aspect relates to a patient interface system that fits a wide range of patients, has improved manufacturability and improved ease-of-use.

Another aspect relates to providing patient interface systems where forces applied to the patient interface structure, such as from tube drag forces or movement of the patient, does not disrupt the seal between the patient interface structure and the patient's airways.

Yet another aspect relates to providing patient interface systems where the patient interface structure, which includes a seal, and a seal positioning and stabilizing structure are coupled to the patient and the air delivery tube is decoupled from the seal. Another aspect is that forces on an air delivery tube and elbow are decoupled from pillows and headgear.

A further aspect relates to patient interface systems in which tension of the seal positioning and stabilizing structure may be set with a lesser regard to overcoming tube drag as the effects of tube drag are isolated from disrupting the seal via decoupling. Thus in accordance with this aspect, the tension of the seal positioning and stabilizing structure may be reduced and patient comfort increased.

Still another aspect relates to providing patient interface systems in which the patient interface structure is connected to a swivel elbow assembly without the use of a rigid frame or shell.

Another aspect of the present technology is a conforming patient interface structure that reduces the number of, or does not include, rigid components. For example, in one form the patient interface does not include a rigid frame.

Another aspect of the present technology is a patient interface structure that in use flexibly wraps around an underside of a patient's nose and accommodates different alar angles.

Another aspect of the present technology is a patient interface structure that accommodates movement of an air delivery tube whilst maintaining an effective seal.

Another aspect of the present technology is a stabilizing structure that directs a seal effecting force to a region close to the sealing surface, e.g. the base of the nose. A force close to the sealing surface reduces a bending arm.

According to yet another aspect of the technology, a front portion of a seal positioning and stabilizing structure is molded from a flexible polymer, for example silicone. Preferably, the seal positioning and stabilizing structure does not include hard plastic stabilizers.

According to a sample embodiment, a patient interface system for delivery of a supply of air at positive pressure to the entrance of a patient's airways for treatment of sleep disordered breathing comprises an air delivery tube connected to a flexible portion of a plenum; a vent structure having sufficient rigidity to support its own weight under gravity and/or not to block or fold under tube movement or tube drag; a patient interface structure, the patient interface structure comprising a seal forming structure arranged on a top portion of the plenum; and a seal positioning and stabilizing structure connected to a flexible portion of the plenum, wherein the seal-forming structure is substantially decoupled from a tube drag force.

According to another sample embodiment, a nasal pillow for delivery of a supply of air at positive pressure to the entrance of a patient's airways for treatment of sleep disordered breathing comprises a stalk; a frusto-conical portion connected to the stalk at a base portion of the frusto-conical portion, the frusto-conical portion comprising a spring structure at base of the frusto-conical portion configured to engage the top lip of the patient and rotate the stalk away from the patient's top lip.

According to yet another sample embodiment, a patient interface structure for delivery of a supply of air at positive pressure to the entrance of a patient's airways for treatment of sleep disordered breathing comprises a flexible base portion; a seal-forming structure connected to base portion; and lateral connectors connected to the flexible base portion substantially in a same plane as a base of the seal-forming structure, wherein the flexible base portion comprises a flexible sidewalled plenum comprising an orifice adapted to receive the supply of air, the orifice having an axis substantially parallel to an axis of the seal-forming structure.

According to a further sample embodiment, a decoupling assembly for decoupling forces applied by a tube on a patient interface structure configured to deliver of a supply of air at positive pressure to the entrance of a patient's airways for treatment of sleep disordered breathing, the patient interface structure comprising a flexible base portion connected to a seal-forming structure, the patient interface structure being held in engagement with the patient in use by a seal positioning and stabilizing structure connected to the flexible base portion, the decoupling assembly comprising the flexible base portion, the seal-forming structure, and at least one of a portion of the seal positioning and stabilizing structure, a swivel elbow, a ball and socket, a swivel sealing ring, and the tube.

According to a still further sample embodiment, a seal positioning and stabilizing structure for a patient interface structure for delivery of a supply of air at positive pressure to the entrance of a patient's airways for treatment of sleep disordered breathing comprises a flexible molded strap comprising a stiffened portion.

In another aspect of the disclosure, a patient interface adapted to be connected to an air delivery tube comprises an under-the-nose gas delivery unit and a plurality of components operatively coupled to the gas delivery unit, said components including headgear, a plenum, frame, or base, and an elbow; and a decoupling system to decouple (or alternatively means for decoupling) at least a portion of a drag (or other dynamic force) from the air delivery tube which would otherwise be applied to the gas delivery unit. The gas delivery unit may be in the form of nasal prongs which are inserted into the nares to form a seal within the wearer's nasal passages, nozzles that seal against the lower, exterior surface of the nares, or nasal cannulae (which are partly inserted into the nasal passages but do not necessarily form a seal therewith). The nozzles may include stalks, heads or other structure to help contribute to decoupling of drag or other dynamic forces. The plurality of components may also include a sealing ring which may contribute to decoupling of tube drag force. The decoupling system (or means for decoupling) may include two or more (or all) of said components (as well as the gas delivery unit itself, e.g, various portions of nozzles) working in concert with one another to decouple the force from the gas delivery unit.

Other aspects, features, and advantages will become apparent from the following detailed description when taken in conjunction with the accompanying drawings, which are a part of this disclosure and which illustrate, by way of example, other aspects and principles.

BRIEF DESCRIPTION OF THE DRAWINGS

The accompanying drawings facilitate an understanding of the various embodiments, wherein:

FIG. 5b schematically illustrates a flexible elbow according to a sample embodiment;

FIGS. 5c and 5d schematically illustrate an elbow configuration according to a sample embodiment;

FIG. 7d schematically illustrates a patient interface structure according to a sample embodiment;

FIG. 8a schematically illustrates a patient interface structure including nasal pillows in accordance with a sample embodiment;

FIG. 8b schematically illustrates a connector of a patient interface structure according to a sample embodiment;

FIGS. 16a-16g schematically illustrate left and right main straps of a main strap loop of a seal positioning and stabilizing structure according to a sample embodiment;

FIGS. 22a and 22b schematically illustrate a sample embodiment of a seal positioning and stabilizing structure strap connector;

FIGS. 23a-23c schematically illustrate a seal positioning and stabilizing structure strap connector according to another sample embodiment;

FIGS. 24a-24l schematically illustrate a seal positioning and stabilizing structure comprising connectors according to another sample embodiment;

FIGS. 25a-25f schematically illustrate seal positioning and stabilizing structure connectors according to other sample embodiments;

FIGS. 28a and 28b schematically illustrate a nasal pillow according to another sample embodiment;

FIGS. 29a and 29b schematically illustrate a nasal pillow according to another sample embodiment;

FIGS. 30a and 30b schematically illustrate a nasal pillow according to another sample embodiment;

FIGS. 31a and 31b schematically illustrate a nasal pillow according to another sample embodiment;

FIGS. 33a and 33b schematically illustrate a nasal pillow according to another sample embodiment;

FIG. 34 schematically illustrates nasal pillows according to another sample embodiment;

FIG. 35 schematically illustrates a nasal pillow according to another sample embodiment;

FIGS. 46a and 46b schematically illustrate straps of seal positioning and stabilizing structures according to sample embodiments.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise," "comprised" and "comprises" where they appear.

The term "air" will be taken to include breathable gases, for example air with supplemental oxygen. It is also acknowledged that blowers or flow generators described herein may be designed to pump fluids other than air. The term "rigid" will be taken to mean not readily deforming to finger pressure, and/or the tensions or loads typically encountered when setting up and maintaining a patient interface in sealing relationship with an entrance to a patient's airways. The term "semi-rigid" means being sufficiently rigid to not substantially distort under the effects of tube drag.

Patient Interface Systems

Introduction

Figure 3A:
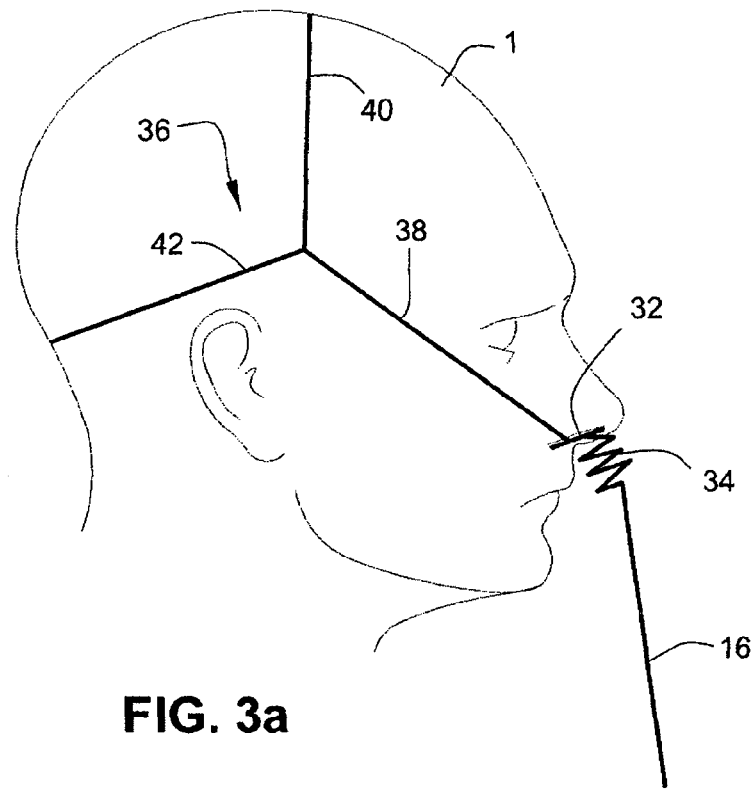
FIG. 3a schematically depicts a patient interface system according to a sample embodiment.

FIG. 3a schematically illustrates an aspect of the present technology whereby headgear tension is directed close to the base of the nose and potentially disruptive effects of tube drag are isolated or decoupled from the seal. See also FIG. 4. By way of contrast, refer to FIG. 1 where headgear structure attempts to stabilize a frame at a point spaced from the sealing surface (the base of the nose) and whereby the tube is directly coupled to the headgear via the rigid frame. Referring to FIG. 3a, a patient interface system according to a sample embodiment may comprise a patient interface structure 32 configured to sealingly engage the airways of the patient 1. The patient interface structure 32 may comprise a seal, for example, nasal pillows or nasal prongs, to sealingly engage the patient's airways. As used herein, the term "nasal pillow" refers to a nozzle-like structure that is configured to be inserted at least partly into the nasal passageway of the patient and form a seal against an outer surface of the patient's nare.

Nasal pillows in accordance with the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement- both displacement and angular- of the frusto-cone and the structure to which the nasal pillow is connected. For example, the frusto-cone may be axially displaced towards the structure to which the stalk is connected.

A related pillow in accordance with the present technology is described in WO 2006/130903 A1, the contents of which are hereby incorporated by reference, for example in paragraphs [00254] and [00255] and FIG. 66c. The term "nasal prong" refers to a nozzle-like structure that is configured to be inserted into the patient's nasal passageway and form a seal with the interior of the patient's nasal passageway. It should also be appreciated that the patient interface structure 32 may comprise a nasal patient interface structure or a full face patient interface structure, i.e. a structure configured to cover part of, or all of, the patient's nose and/or mouth and seal against the patient's face. The patient interface structure may be formed of, for example, silicone, foam, or gel.

The patient interface structure 32 may be connected to an air delivery hose or tube 16 by a decoupling arrangement 34. The decoupling arrangement 34 may include, for example, a flexible portion of the patient interface structure 32, a swivel elbow including, e.g., a ball and socket connection, and/or a swivel seal ring. The air delivery hose may be a retractable hose, as disclosed, for example, in U.S. application Ser. No. 12/211,896, filed Sep. 17, 2008, the entire contents of which are incorporated herein by reference.

The patient interface system may also comprise a seal positioning and stabilizing structure 36 that is configured to position and stabilize the patient interface structure 32 in sealing engagement with the patient's airways. The seal positioning and stabilizing structure 36 may be flexible. As shown in FIG. 3a, the seal positioning and stabilizing structure is connected to the patient interface structure 32. The seal positioning and stabilizing structure 36 may include a side straps, or members, 38 configured to extend along each side of the patient's face, only one being shown in FIG. 3a, a top strap 40 configured to extend across the top of the patient's head, and a rear strap 42 configured to extend around the back of the patient's head.

In use, each side strap 38 of the seal positioning and stabilizing structure 36 may be attached to the patient interface structure 32. For example, a connector may be provided on each side of the patient interface structure 32, one on each side of the nose of the patient 1. It should be appreciated that multiple connectors may be provided to the patient interface structure and in any arrangement, for example two connectors on each side of the nose of the patient. The pair of connectors form a connection between the patient interface structure 36 and the seal positioning and stabilizing structure 36 as described in more detail herein. The connection is close to the entrance to the nares of the patient 1. In this way, the straps 38, 40, 42 of the seal positioning and stabilizing structure 36 hold the seal in position against the face of the patient more directly than in prior art arrangements, such as the prior art arrangement shown in FIG. 1. In the prior art arrangement of FIG. 1, the connection of the seal positioning and stabilizing structure strap to the frame is displaced from the entrance to the patient's nares and the patient interface structure is held against the face of the patient in an indirect manner.

In the arrangement shown in FIG. 3a, the decoupling arrangement 34 is provided between the connection of the straps 38 of the seal positioning and stabilizing structure 36 and the connection with the air delivery tube 16 so that tube drag does not directly impact the seal formed between the patient interface structure 32 and the patient's airways.

Figure 1:
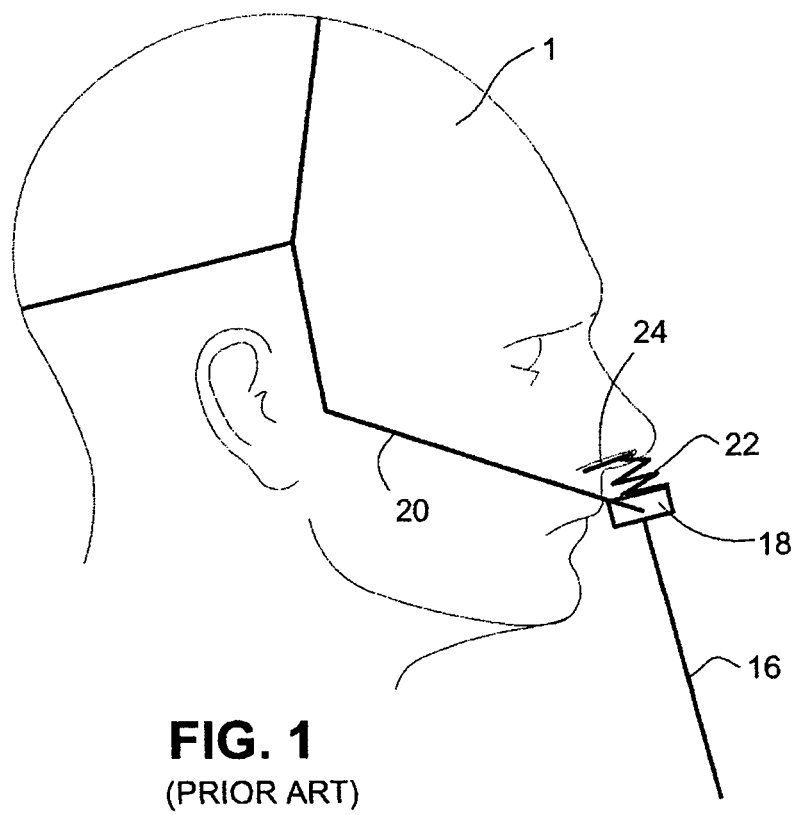
FIG. 1 schematically depicts a patient interface system according to the prior art.

In a typical prior art arrangement, for example the one shown in FIG. 1, the tension of the headgear is often set at a level both to form a seal and to overcome tube drag that may occur. However, according to the sample embodiment shown in FIG. 3a, the tube drag is to some extent decoupled from the seal formed between the patient interface structure 32 and the patient's airways and the tension provided by the seal positioning and stabilizing structure need only be set at a level necessary for sealing. Hence, the tension may be set with a lesser regard for overcoming tube drag. The decreased tension provides increased patient comfort.

As shown in FIG. 3a, the flexible seal positioning and stabilizing structure 36 may be configured so that the force vectors provided by the straps 38, 40, 42 of the seal positioning and stabilizing structure 36 maintain the patient interface structure 32 in sealing engagement with the nares of the patient 1. It should be appreciated, however, that other seal positioning and stabilizing structures may be utilized, as described in more detail herein. For example, straps may be routed around and engaged with the ears of the patient. According to another sample embodiment, the straps may be eliminated and a nasal clip may be used to hold the seal of the patient interface structure 32 in position.

The seal positioning and stabilizing structure 36 may be formed of a foam and fabric laminated material, such as BREATHOPRENE®. Alternatively, the seal positioning and stabilizing structure 36 may be made from silicone or other polymers. One of the benefits of using silicone or BREATHOPRENE® is there is no difference in temperature of patient's skin when using either silicone or BREATHOPRENE® headgear. However, silicone can discolor over time (typically oxidizes to yellow). Therefore, it may be desirable to add a tint, such as light blue, to the silicone to reduce the visual impact of discoloration. Sharp corners of the headgear may also be rounded to reduce incidences of irritation to the patient's skin.

The silicone could be polished or matte on both sides or matte on one side and polished on the other—preferably matte on both sides, or matte on the skin contacting side and polished on the outer side. Matte surface finish gives the perception of comfort.

The decoupling arrangement 34 acts as a flexible connection and links the patient interface structure 32 to the air delivery tube 16. According to the sample embodiment shown in FIG. 3a, only the seal of the patient interface structure 32 is held in a set location. There is no shell or frame that needs to be held in a set location. The decoupling arrangement 34 is free to move with the air delivery tube 16, thereby reducing tube drag and increasing the stability of the seal formed between the patient interface structure 32 and the airways of the patient 1.

Use of the seal positioning and stabilizing structure 36 also permits rotation of the plane of the patient interface structure 32 with respect to the seal positioning and stabilizing structure 36 to accommodate different naso-labial angles and different positions of the mask in use. For example, the connectors provided on the patient interface structure 32 may include a plurality of connection points to allow the relative position of the patient interface structure 32 with respect to the seal positioning and stabilizing structure 36 to be changed or adjusted. The axis about which rotation may be provided may be defined as being parallel to a line drawn through both eyes of the patient, and being located below the nose of the patient.

Figure 3B:
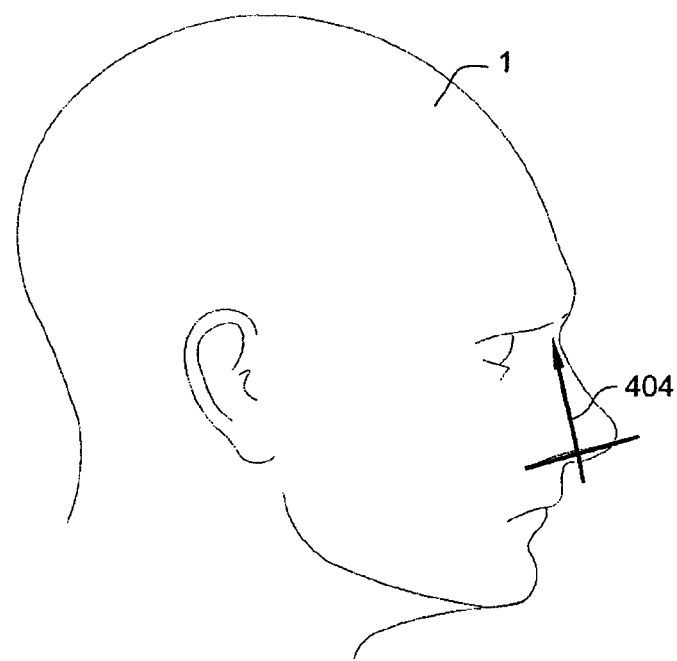
FIG. 3b schematically illustrates a vector provided by sample embodiments.

As shown in FIG. 3b, a desirable vector 404 will produce force normal to the nares. The entire vector 404 pulls the seal, e.g. the pillows, against the nares.

The vectors of the seal positioning and stabilizing structure 36 of the sample embodiments are configured to force the seal, e.g. the pillows, up against the patient's nose. The vectors may be modified by the direction of the straps 38, 40, 42.

For example, the straps 38 may extend higher on the face (i.e. closer to the eyes than the ears of the patient's cheek) to increase force in the vertical axis thereby increasing the force up and against the user's nose.

The shape of the straps 38, 40, 42 may also be configured to provide a desirable vector: According to sample embodiments, an arrangement without a frame requires orientation of the pillows using the seal positioning and stabilizing structure alone. The width of the straps may be varied to force the seal to tilt in the direction indicated by the vector 404. The width of the straps may be gradually increased from the cheek region to the nasal region to stabilize the patient interface structure 32.

Altering the thickness of the straps changes the rigidity and thus force distribution along the straps.

Figure 44A:
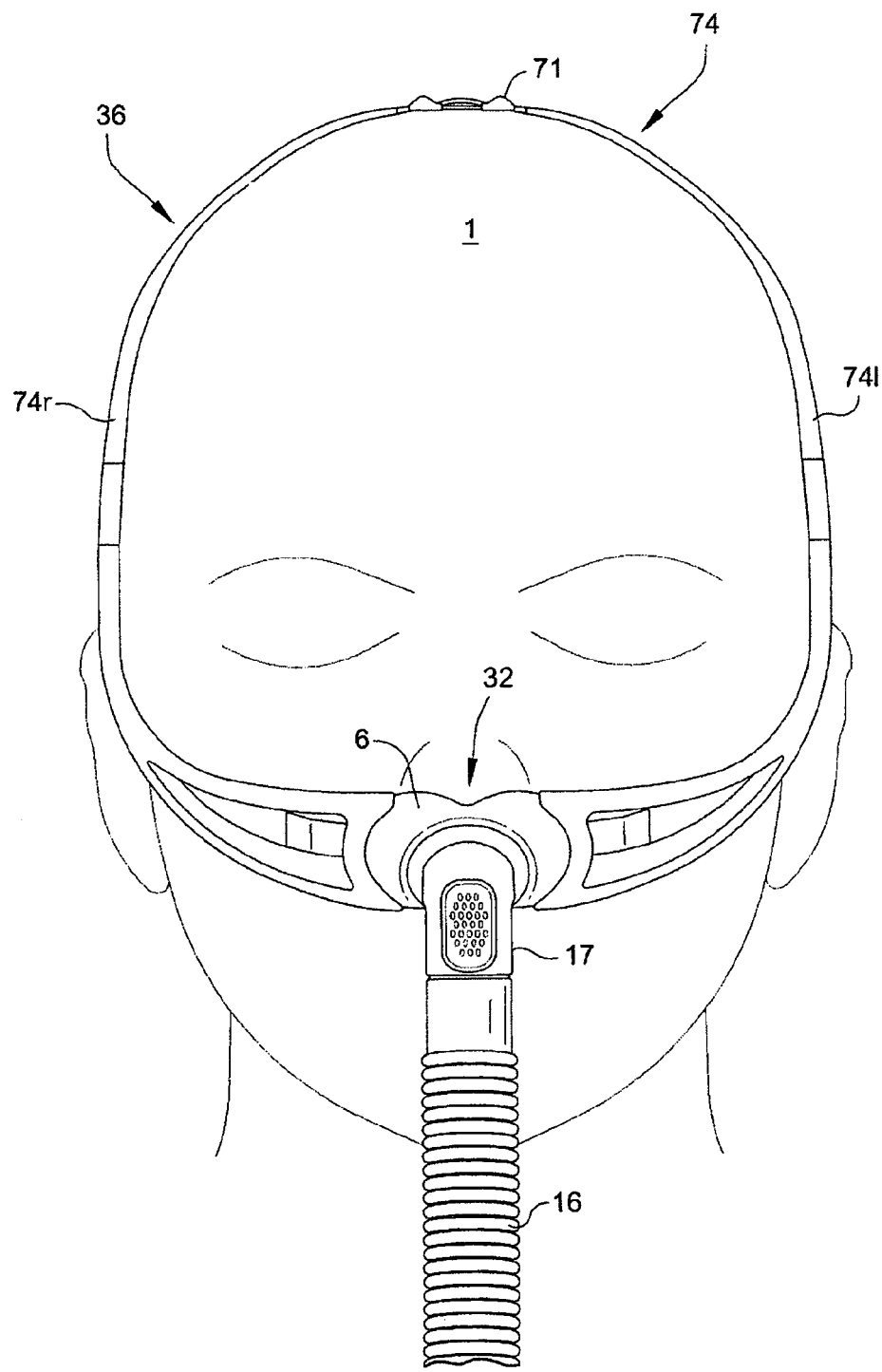
FIGS. 44a and 44b schematically illustrate a patient interface system according to a sample embodiment.
Figure 44B:
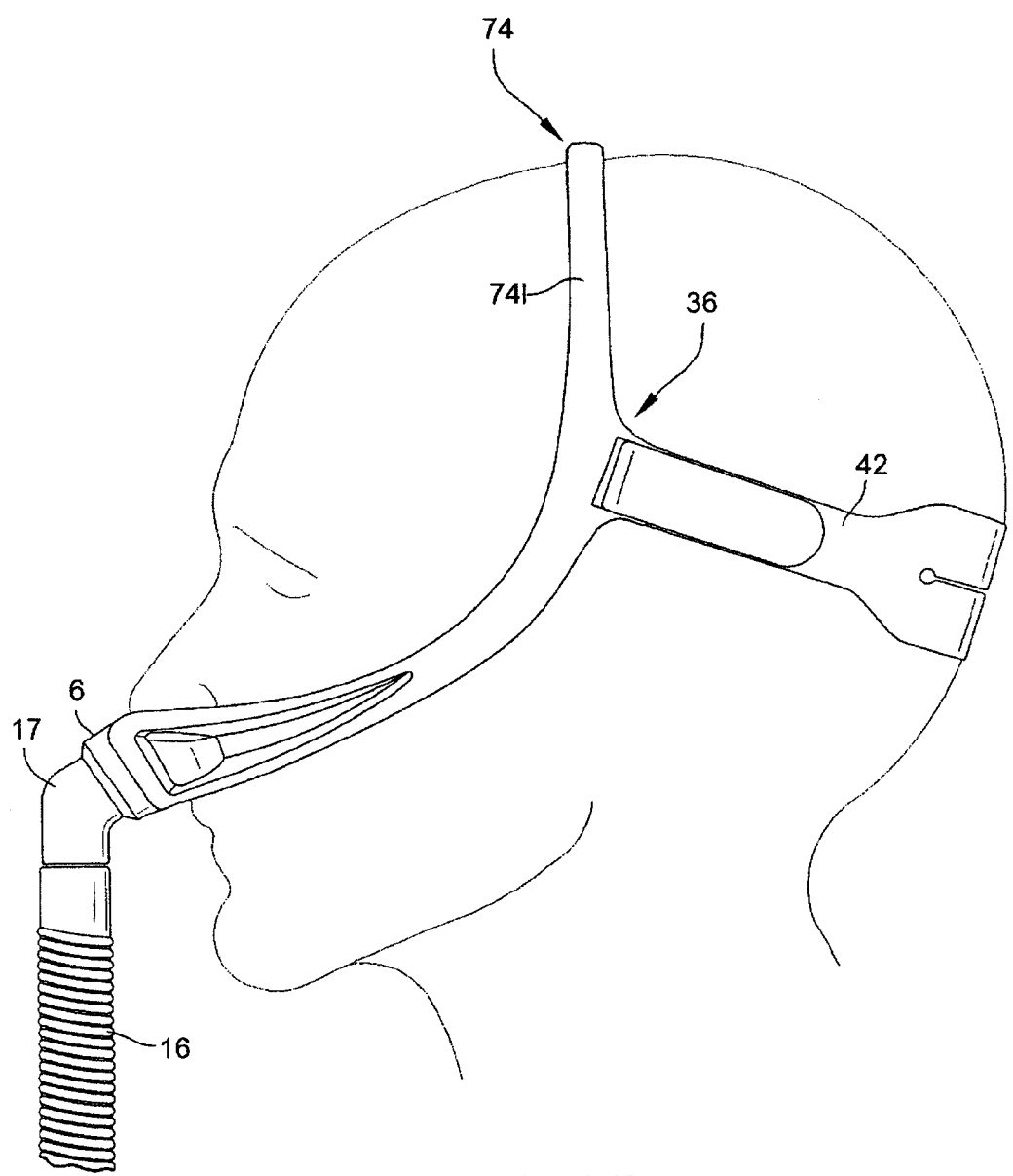

Referring to FIGS. 44a and 44b, a patient interface system according to a sample embodiment includes a patient interface structure 32 including a flexible base 6. A seal is supported by the flexible base 6. The patient interface structure 32 is configured to be held in sealing engagement with the entrance to the patient's airways. The patient interface structure 32 is held in sealing engagement with the patient's face by a seal positioning and stabilizing structure 36 that includes a main strap loop 74 and a rear strap 42. The main strap loop 74 includes a right main strap 74r and a left main strap 74l that are configured to be connected at respective first ends to the patient interface structure 32. The right and left main straps 74r, 74l are configured to be connected to each other at respective second ends, for example by a connector 71, for example a buckle. A rear strap 42 of the seal positioning and stabilizing structure 36 extends around the back of the patient's head at a position above the patient's ears and is connected at respective ends to the right and left main straps 74r, 74l at positions between the first and second ends of the straps 74r, 74l.

Figure 47A:
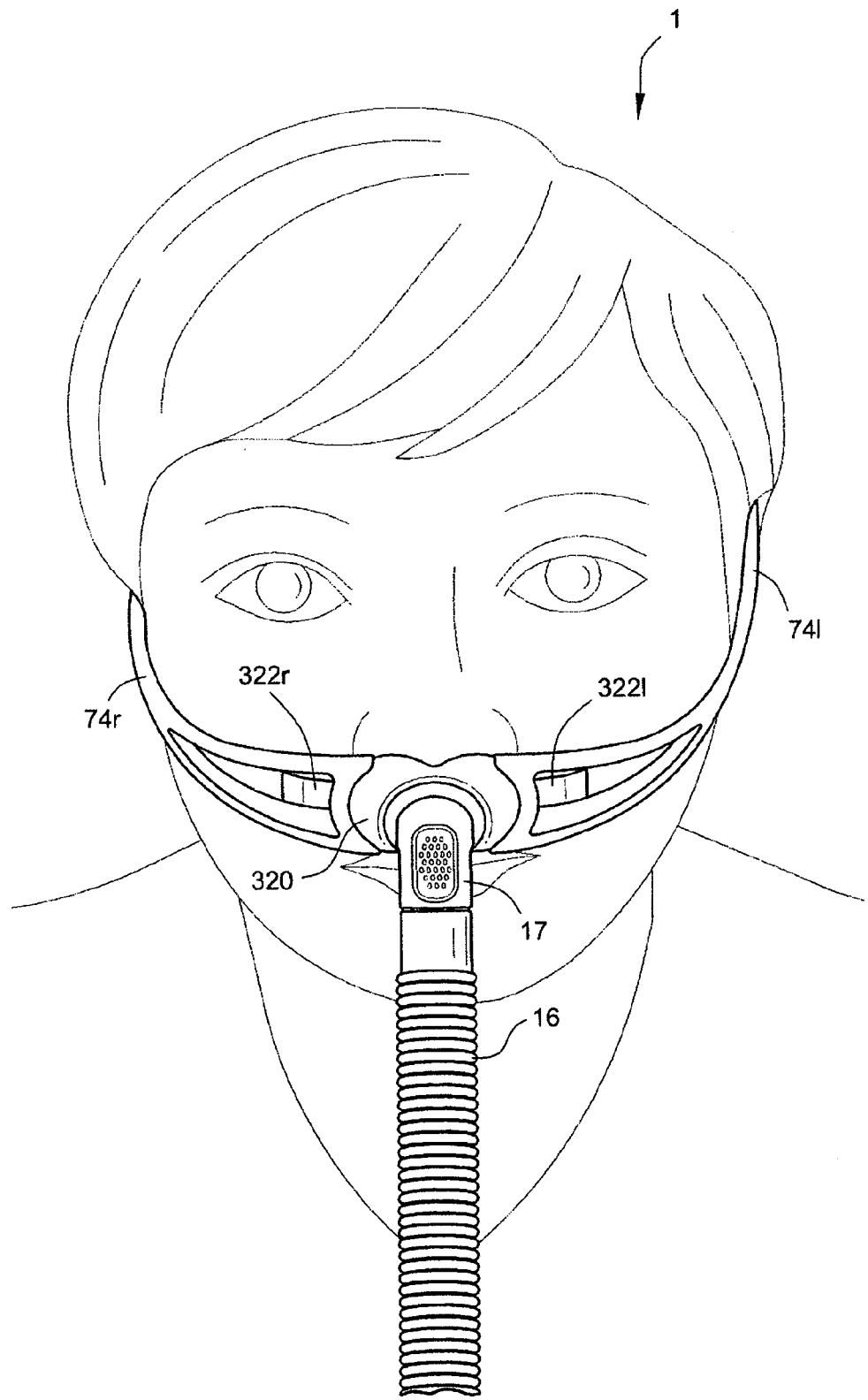
FIGS. 47a and 47b schematically illustrate a patient interface system according to a sample embodiment.
Figure 47B:
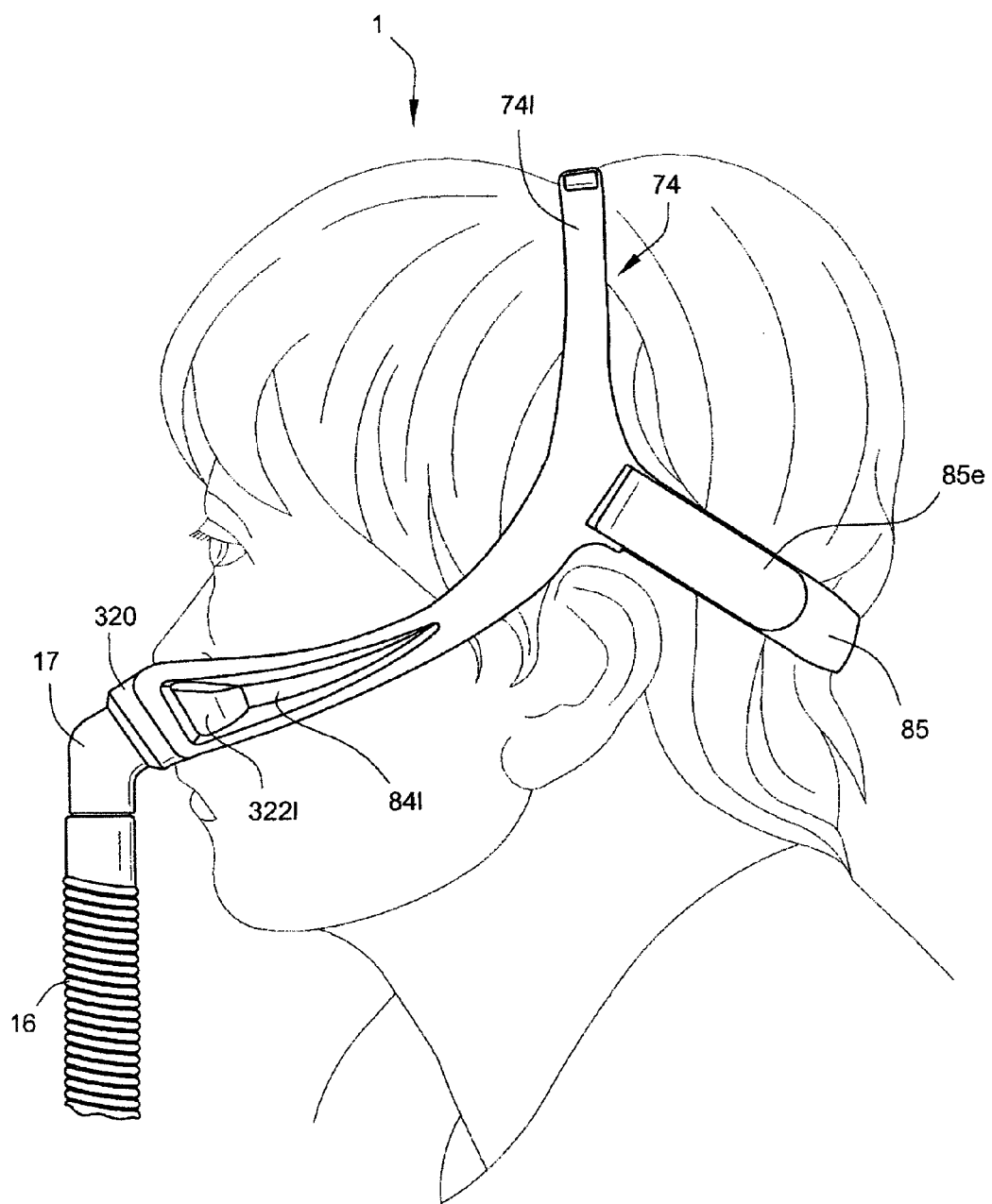

Referring to FIGS. 47a and 47b, a patient interface system according to another sample embodiment includes a patient interface structure 320 including a flexible base. A seal is supported by the flexible base. The patient interface structure 320 is configured to be held in sealing engagement with the entrance to the patient's airways. The patient interface structure 320 is held in sealing engagement with the patient's face by a seal positioning and stabilizing structure that includes a main strap loop 74 and a rear strap 85 having adjustable ends 85e. The main strap loop 74 includes a right main strap 74r and a left main strap 74l that are configured to be connected at respective first ends to the patient interface structure 320. The right and left main straps 74r, 74l may be connected to each other at respective second ends, for example by a connector, for example a buckle. The rear strap 85 of the seal positioning and stabilizing structure extends around the back of the patient's head at a position above the patient's ears and is connected at respective ends to the right and left main straps 74r, 74l at positions between the first and second ends of the straps 74r, 74l.

The right and left main straps 74r, 74l may be formed, for example, from silicone. The silicone may be, for example, translucent or transparent. The patient interface system is therefore less obtrusive and presents a visually more appealing appearance (e.g. to a patient's bed partner).

The "take off angle" of the straps 74r, 74l from a connection point provides a more direct angle to a base of the patient's temple and are generally higher up on the patient's face. The patient interface structure also conforms, or wraps around, the region of the patient's mouth and provides less interference with the area around the mouth. The seal positioning and stabilizing structure also covers less of an extent of the patient's face.

Figure 4:
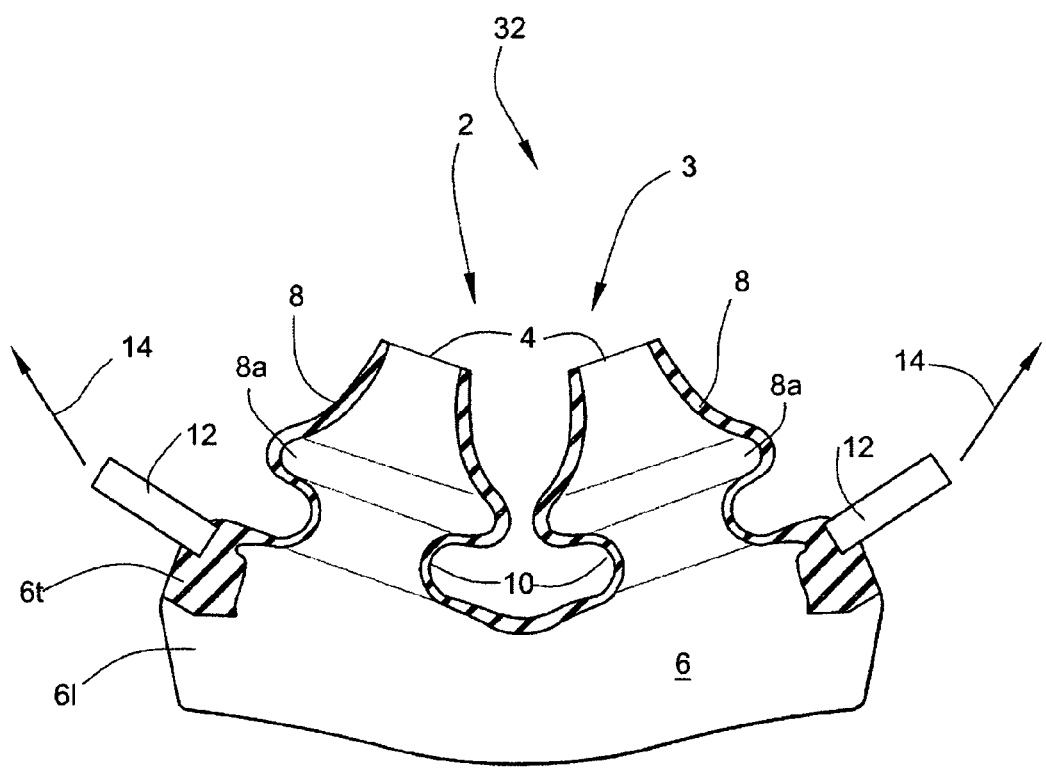
FIG. 4 schematically illustrates a patient interface structure according to a sample embodiment.

Patient Interface Structure
Patient Interface Structure Including Nozzle Assembly Seal Referring to FIG. 4, a patient interface structure 32 according to a sample embodiment includes a seal 2 configured to sealingly engage the patient's airways. The seal 2 may comprise a nozzle assembly 3 that may comprise a pair of nasal pillows 4 connected to a base portion 6. The pillows 4 each include a conical portion 8 at least part of which is adapted to form a seal with a nare of the patient 1. As discussed above, a portion of each pillow 4 is configured to be inserted into the patient's nasal passageway, but not to form a seal inside the nasal passageway. The conical portion 8 of the pillow 4 includes a sealing surface, or zone, 8a that is configured to engage the nare of the patient and form a seal. The sealing surface, or zone, 8a may be as disclosed, for example in FIG. 21 of WO 2004/073778 A1, which is incorporated herein by reference. Each nasal pillow 4 also includes a stalk, or neck portion, 10 which connects the nasal pillow 4 to a flexible base 6. The stalk, or neck portion, 10 may have a length of between about 3 mm to about 6 mm.

The flexible base 6 is able to wrap around the underside of the nose in use when under tension, and can accommodate different facial geometries. The flexible base 6 includes a pair of connectors 12 configured for connection to a seal positioning and stabilizing structure. The seal positioning and stabilizing structure connectors 12 are arranged at a top portion 6t of the flexible base 6, generally in the same plane as the base of the stalks of the nasal pillows 4. As used herein, the term "top portion" refers to the portion of the flexible base that is adjacent to the seal of the patient interface structure. When viewed from the side (for example in FIGS. 17g and 17h) an axis through the stalks of the pillows is generally parallel to a normal to the aperture 324 wherethough a supply of air is delivered. This arrangement facilitates a generally narrower patient interface structure than for example the ResMed SWIFT® I (see for example FIG. 76A of WO 2004/073778 A1), or the Innomed NASAL AIRE™ I where air is fed from the side leading to a wider overall mask structure, and hence a patient interface structure in accordance with the present technology is more amenable to side-sleeping by a patient. Other patient interface structures, such as in the Fisher & Paykel OPUS™ and OPUS™ 360, include air delivery at an obtuse angle with respect to the angle of the axis of the nasal pillow when viewed from a corresponding orientation to FIGS. 17g and 17h. This approach may lead to a greater bulk of structure.

Tension 14 is applied to patient interface structure 32 by the seal positioning and stabilizing structure to hold the nasal pillows 4 of the seal 2 in sealing engagement with the nares of the patient 1. A lower portion 6l of the flexible base 6 forms part of a decoupling arrangement. For example, the lower portion 6l of the flexible base 6 may comprise a gusset, such as the gusset disclosed in WO 01/97893 A1, which is incorporated herein by reference. As used herein, the term "lower portion" refers to the portion of the flexible base that is configured to be connected to an air delivery tube or hose, or to a frame or shell. The lower portion 6l may define a plenum with flexible side walls. The plenum is flexible, but not so limp or floppy that it cannot support its own weight. In other words, the plenum is capable of holding its shape before pressurization by the flow of breathable gas. In this sense, the plenum may be described as semi-rigid.

The plenum may have flexible bellows-like structure on left- and right-hand sides, and narrowed portions adjacent the top lip and underside of nose to avoid contact therewith in use. See for example FIG. 17a where the end of line 329 is located in a flexible bellows-like region 339 and the end of arrow 320 is adjacent a narrowed region 321, as also shown in FIG. 18r. See also FIG. 17d where T4 indicates a thickness suitable to provide the flexibility illustrated in FIGS. 42a-42c and FIGS. 43a-43c. The flexibility of the plenum is facilitated by manufacture in a material such as silicone with a Shore A durometer in the range of about 20 to about 60, more preferably about 30 to about 50, most preferably about 40. A harder silicone may use thinner walls, a softer silicone may use thicker walls. A rounded bellows-like structure also facilitates flexibility independent of the material it is constructed from. Another plenum may be molded from polyurethane foam. Prior patient interfaces such as the Fisher & Paykel INFINITY™ 481, OPUS™, OPUS™ 360, and the Respironics OPTILIFE™ include a range of rigid materials such as polycarbonate. Other masks such as the AIRSEP™ Ultimate mask include rigid headgear connectors.

The patient interface structure 32 may be formed in one piece, for example by molding a material such as silicone. In one form of the sample embodiment, the range of movement provided by the flexibility of the pillows 4 with respect to the top portion 6t of the flexible base 6 may be relatively small compared with the range of movement provided by the lower part 6l of the flexible base 6 acting as part of the decoupling arrangement.

In use, a strap of the seal positioning and stabilizing structure is attached to each seal positioning and stabilizing structure connector 12, one on each side of the nose of the patient, for example as shown in FIG. 3, establishing a connection. The connection is close to the plane of the entrance to the nares of the patient. In this way, the straps of the seal positioning and stabilizing structure 36 more directly hold the nasal pillows 4 in position than in prior art arrangements, such as shown in FIG. 1, where the connection is displaced from the plane of the entrance to the nares of the patient. Other prior art patient interfaces such as the Fisher & Paykel INFINITY™ 481, OPUS™, OPUS™ 360, and the Respironics OPTILIFE™ place the point of connection at some distance from the nares. The lower portion 6l of the flexible base 6 acts as part of a decoupling arrangement between the plane of connection with the straps of the seal positioning and stabilizing structure 36 and the connection with the air delivery tube 16 so that tube drag does not directly impact the seal formed between the nasal pillows 4 and the nares of the patient.

Figure 8C:
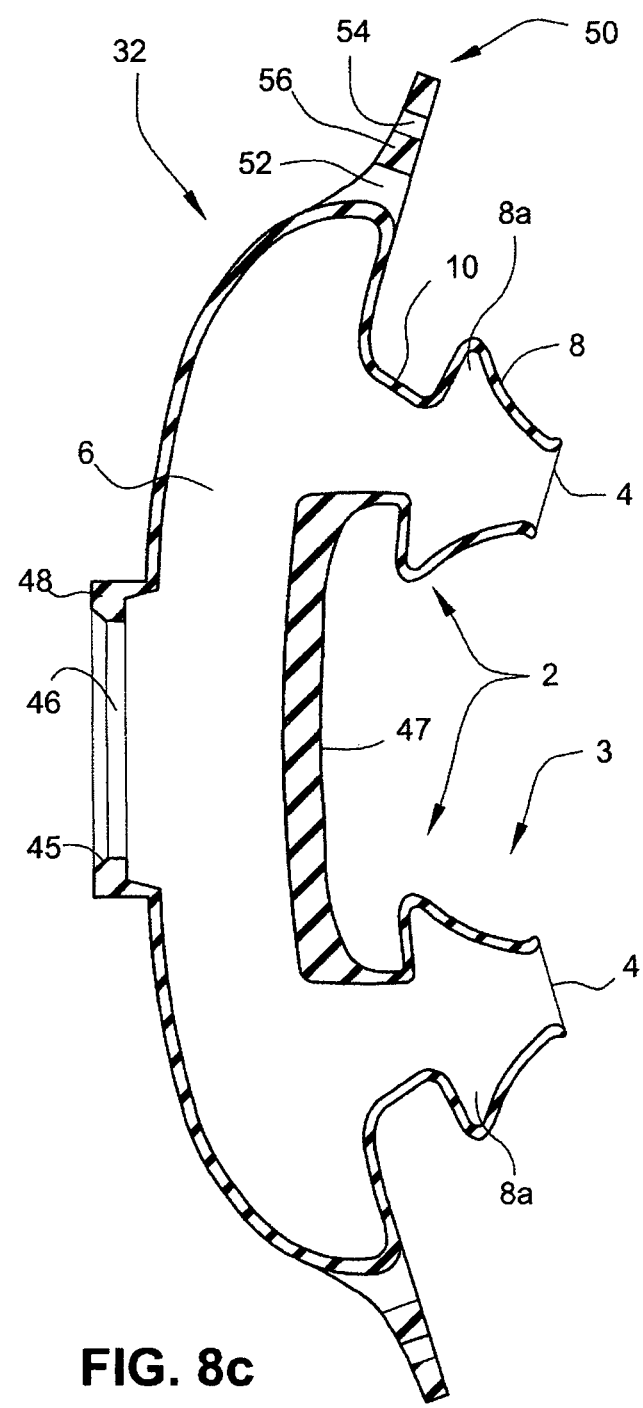
FIG. 8c schematically illustrates a patient interface structure including nasal pillows in accordance with another sample embodiment.
Figure 8D:
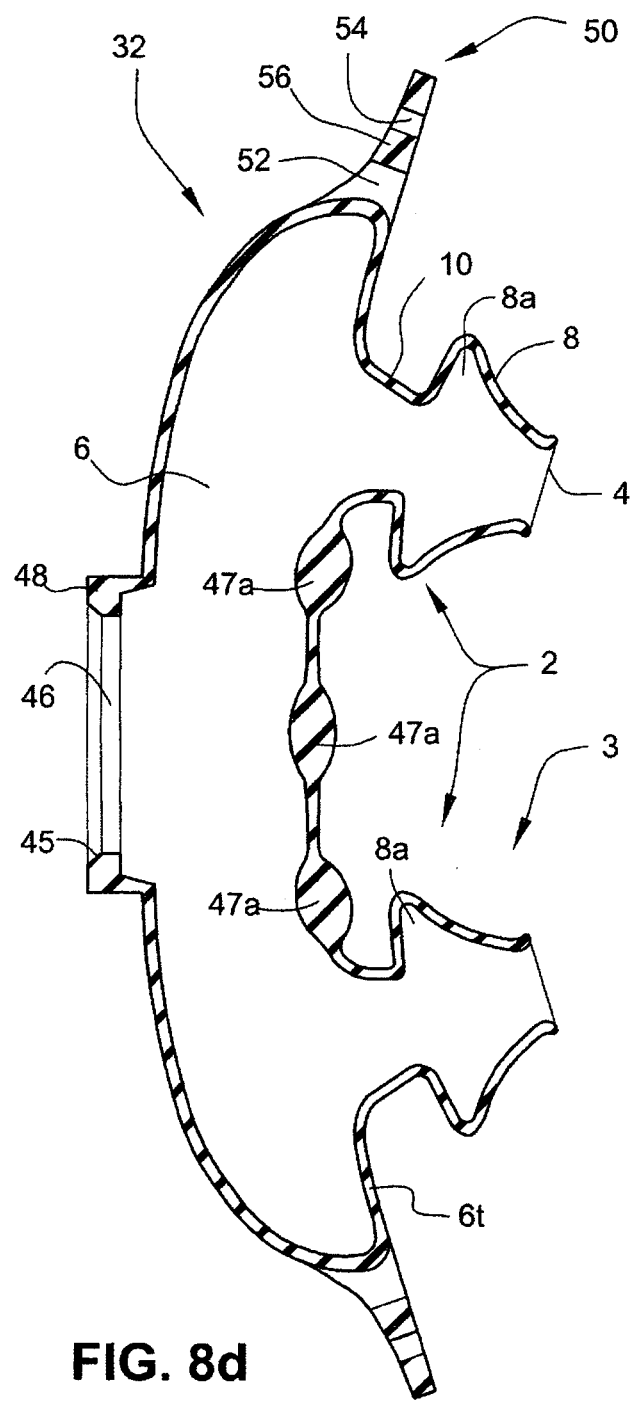
FIG. 8d schematically illustrates a patient interface structure including nasal pillows in accordance with another sample embodiment.
Figure 8E:
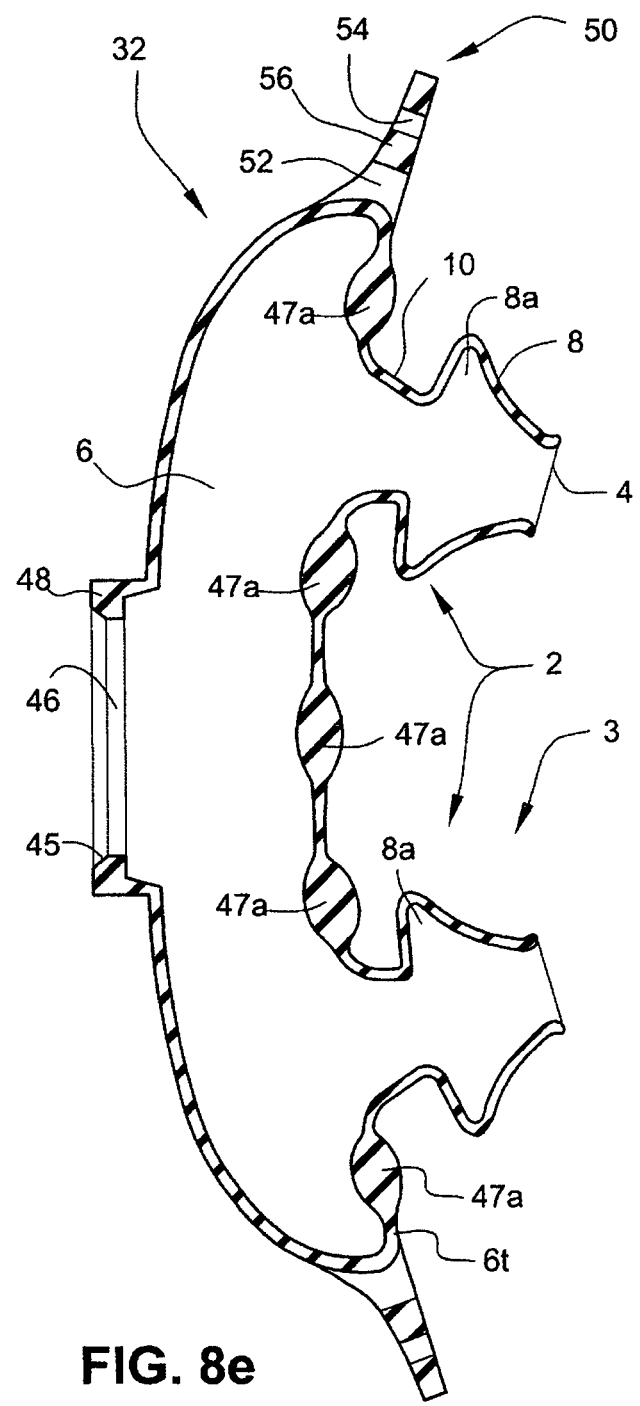
FIG. 8e schematically illustrates a patient interface structure including nasal pillows in accordance with another sample embodiment.
Figure 8F:
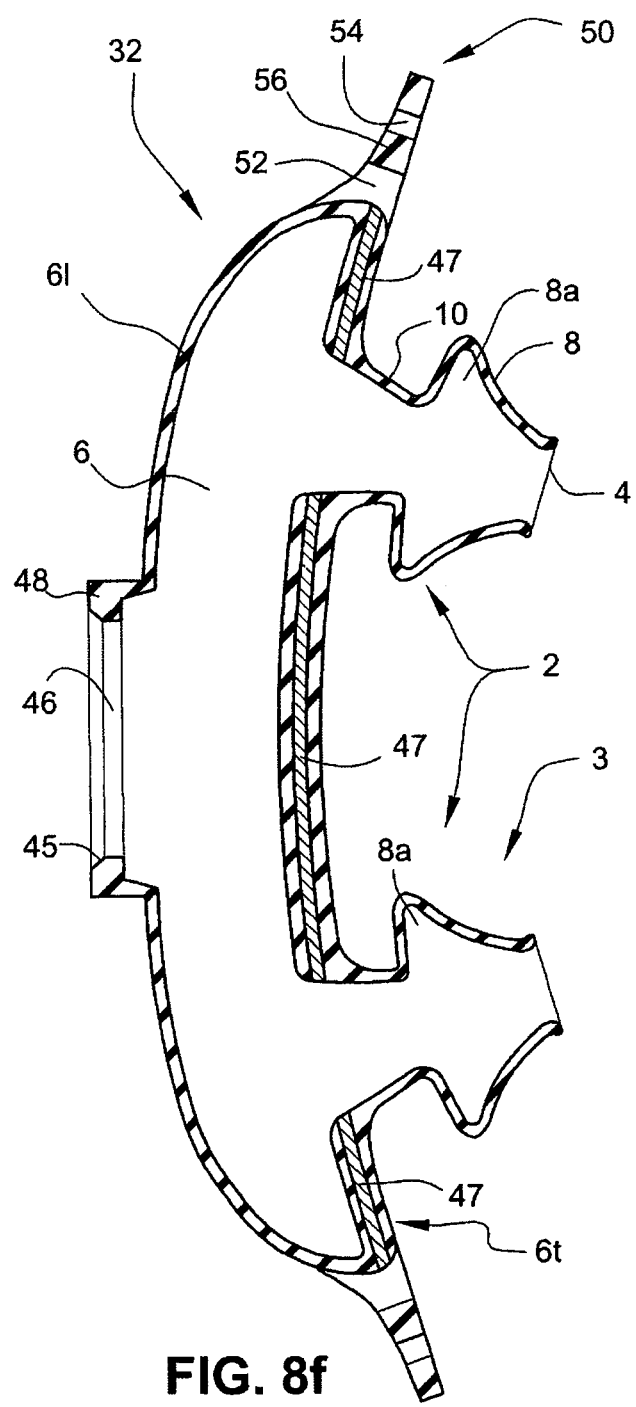
FIG. 8f schematically illustrates a patient interface structure including nasal pillows in accordance with another sample embodiment.
Figure 8G:
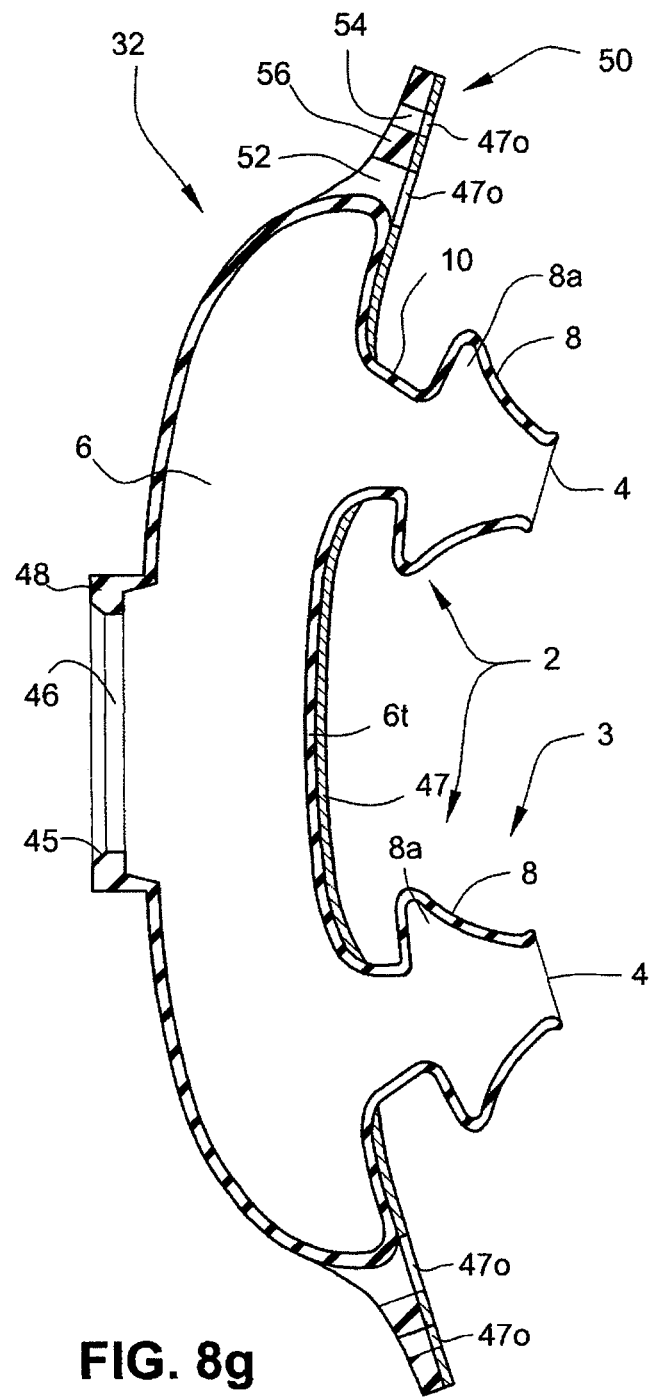
FIG. 8g schematically illustrates a patient interface structure including nasal pillows in accordance with another sample embodiment.
Figure 8H:
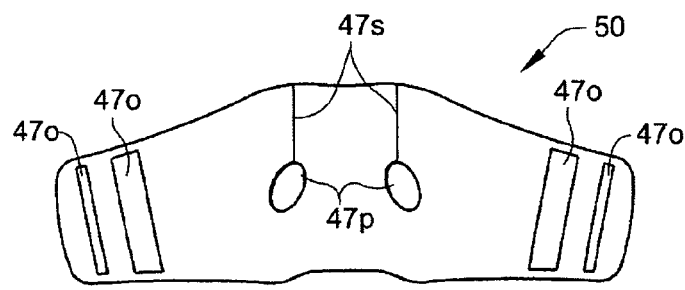
FIG. 8h schematically illustrates a linking element of the patient interface structure of FIG. 8f.
Figure 8I:
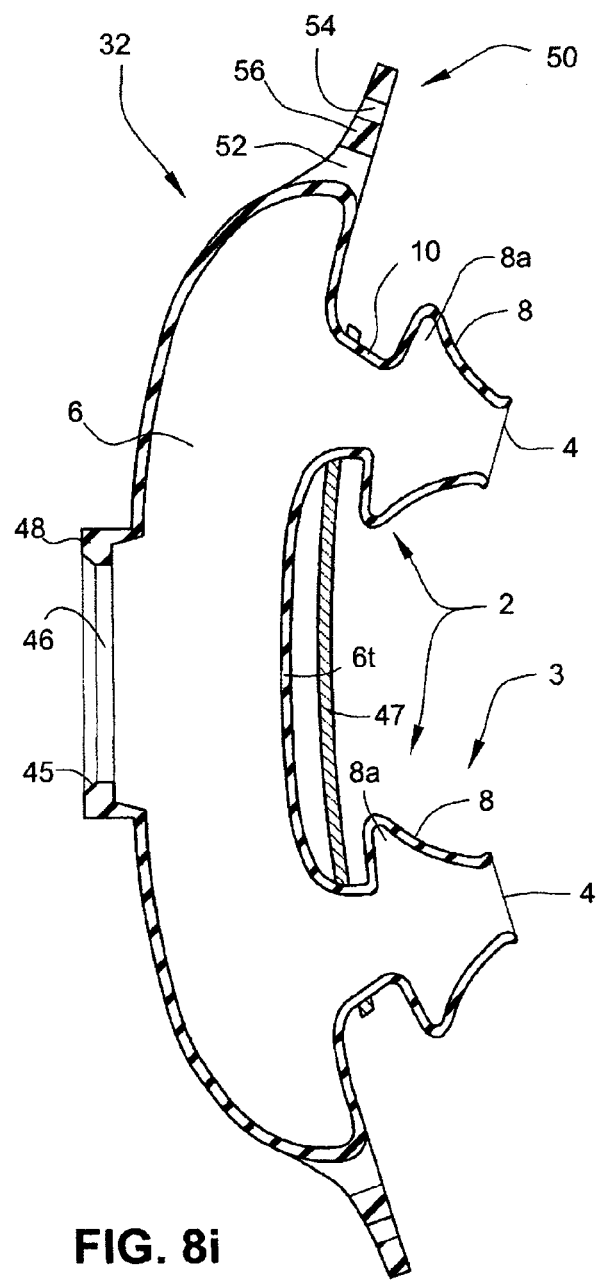
FIG. 8i schematically illustrates a patient interface structure including nasal pillows in accordance with another sample embodiment.
Figure 8J:
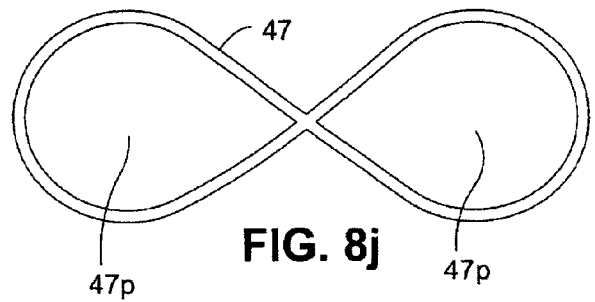
FIG. 8j schematically illustrates the linking element of the patient interface structure of FIG. 8i.
Figure 8K:
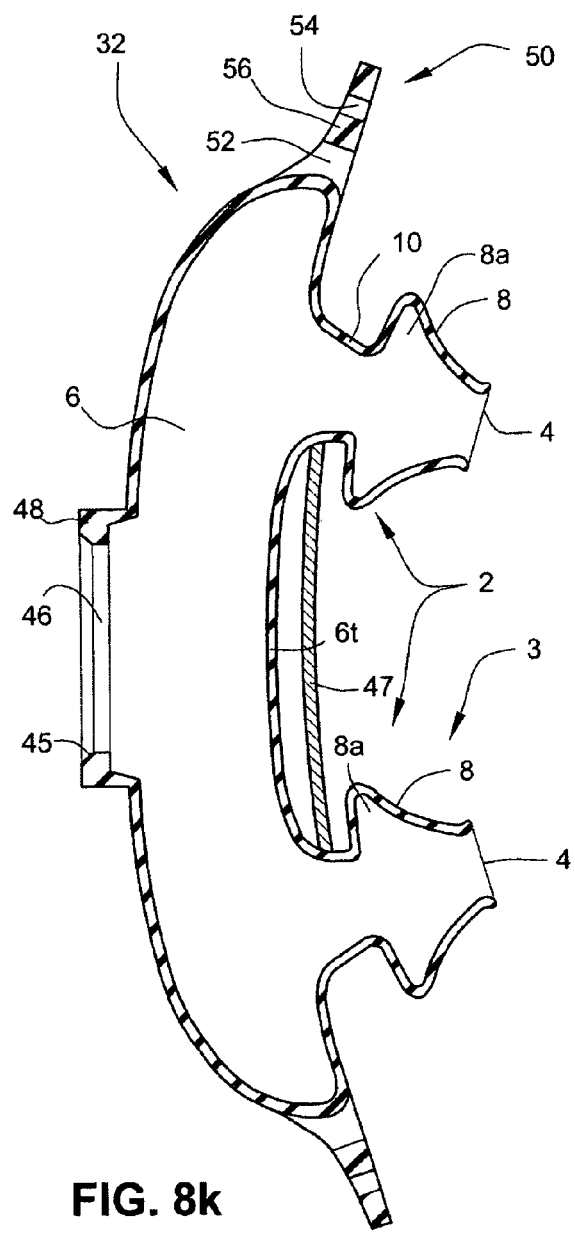
FIG. 8k schematically illustrates a patient interface structure including nasal pillows in accordance with another sample embodiment.
Figure 8L:
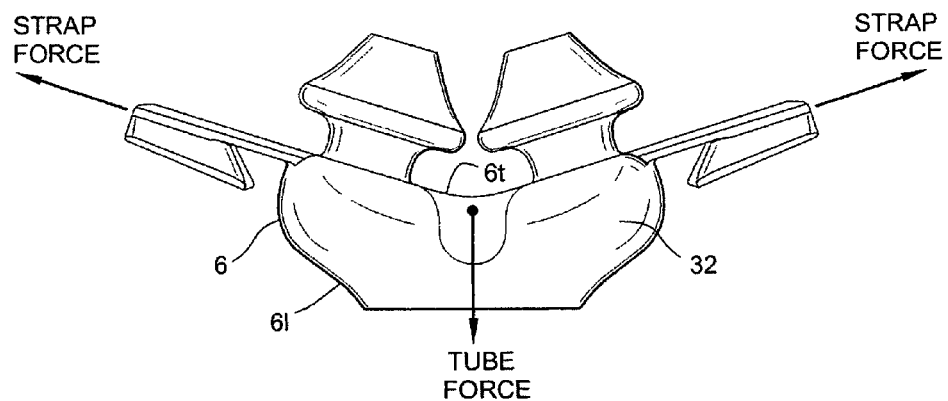
FIGS. 8l and 8m schematically illustrate a comparison between sample embodiments.
Figure 8M:
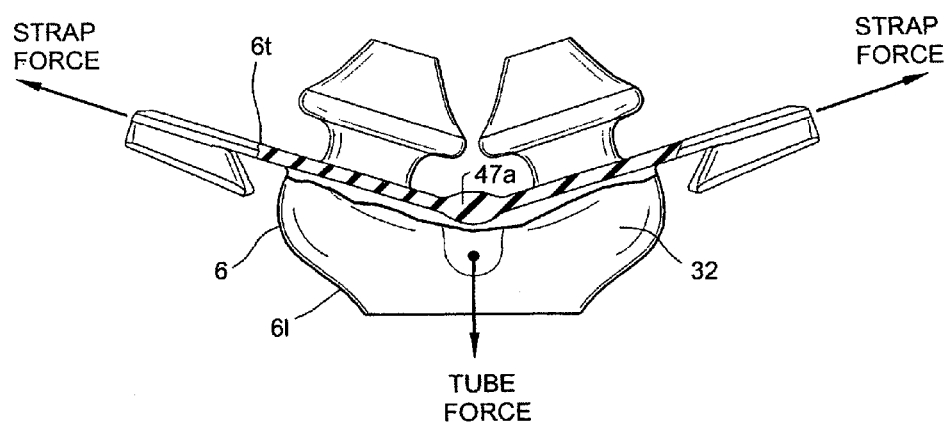
Figure 8N:
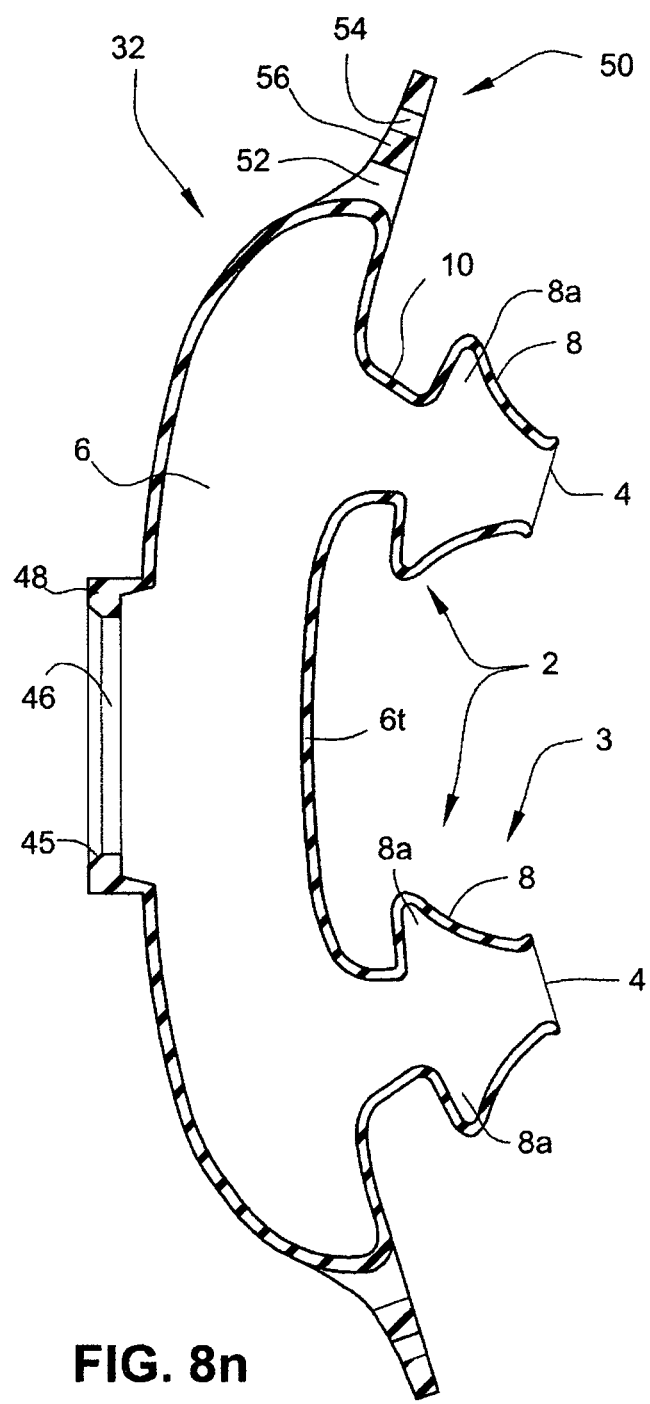
FIG. 8n schematically illustrates a patient interface structure including nasal pillows in accordance with another sample embodiment.

Referring to FIGS. 8b and 8n, a patient interface structure 32 according to another sample embodiment may comprise a seal 2 comprising a nozzle assembly 3 having a pair of nasal pillows 4. The flexible base 6 may include integrally formed connectors 50. The patient interface structure 32 may be coupled to a decoupling arrangement, e.g. a swivel ring, to decouple tube drag forces as will be described in more detail.

Each nasal pillow 4 may include a conical portion 8 and a neck portion 10. Each conical portion 8 may comprise a sealing zone 8a configured to form a seal against the patient's nare. The nasal pillows 4 may be formed with the patient interface structure 32 or may be removably attached to the patient interface structure 32, for example as described in WO 2005/063328, the entire contents of which are incorporated by reference. The patient interface structure 32 may further comprise an aperture 46 for introduction of a flow of breathable gas into the patient interface structure 32. The aperture 46 may be formed in a lower portion 6l of flexible base 6 and be surrounded by a flange 48 that is configured for engagement with an air delivery tube, or a swivel elbow assembly, or a ball and socket joint. It should also be appreciated that the flange 48 of the patient interface structure 32 may be configured for connection to a frame or shell.

The patient interface structure 32 may be formed of a flexible material, such as silicone. The patient interface structure 32 may be formed of one piece, including the nasal pillows 4, the flange 48, and a pair of connectors 50 provided at each end of the patient interface structure 32. As shown in FIG. 8b, each connector 50 may comprise a first slot 52 and a second slot 54 for receipt of an end of a strap of the seal positioning and stabilizing structure. The first slot 52 and a second slot 54 are separated by a crosspiece 56 which may engage the end of the strap to retain the end of the strap in contact with the connector 50. The patient interface structure, including the connectors 50, is flexible and forces applied by the seal positioning and stabilizing structure, for example by side straps, stretch the connector 50 to increase the force that the crosspiece 56 exerts on the seal positioning and stabilizing structure strap.

The patient interface structure 32, including the connectors 50, may be integrally formed, for example by molding. The patient interface structure 32 may be formed so as to have varying densities and/or hardnesses. For example, the nasal pillows 4 and/or the flexible base 6 may be formed of a first density and/or hardness and the connectors 50 may be formed of a second density and/or hardness. The second density and/or hardness may be higher than the first density and/or hardness. This permits the patient interface structure 32 to be formed so as to have a softer feeling in those areas that engage the patient's face (e.g. the nozzle assembly of the seal) and a harder, or more rigid, feeling in the area connected to the seal positioning and stabilizing structure. The hardness, e.g. durometer, of the patient interface structure may be different from the hardness of the seal positioning and stabilizing structure discussed below. For example, the durometer of the connectors and/or flexible base of the patient interface structure may be different from the straps and/or the connectors of the straps of the seal positioning and stabilizing structure.

Patient Interface Structure Including Nasal Prongs as Seal

Figure 5A:
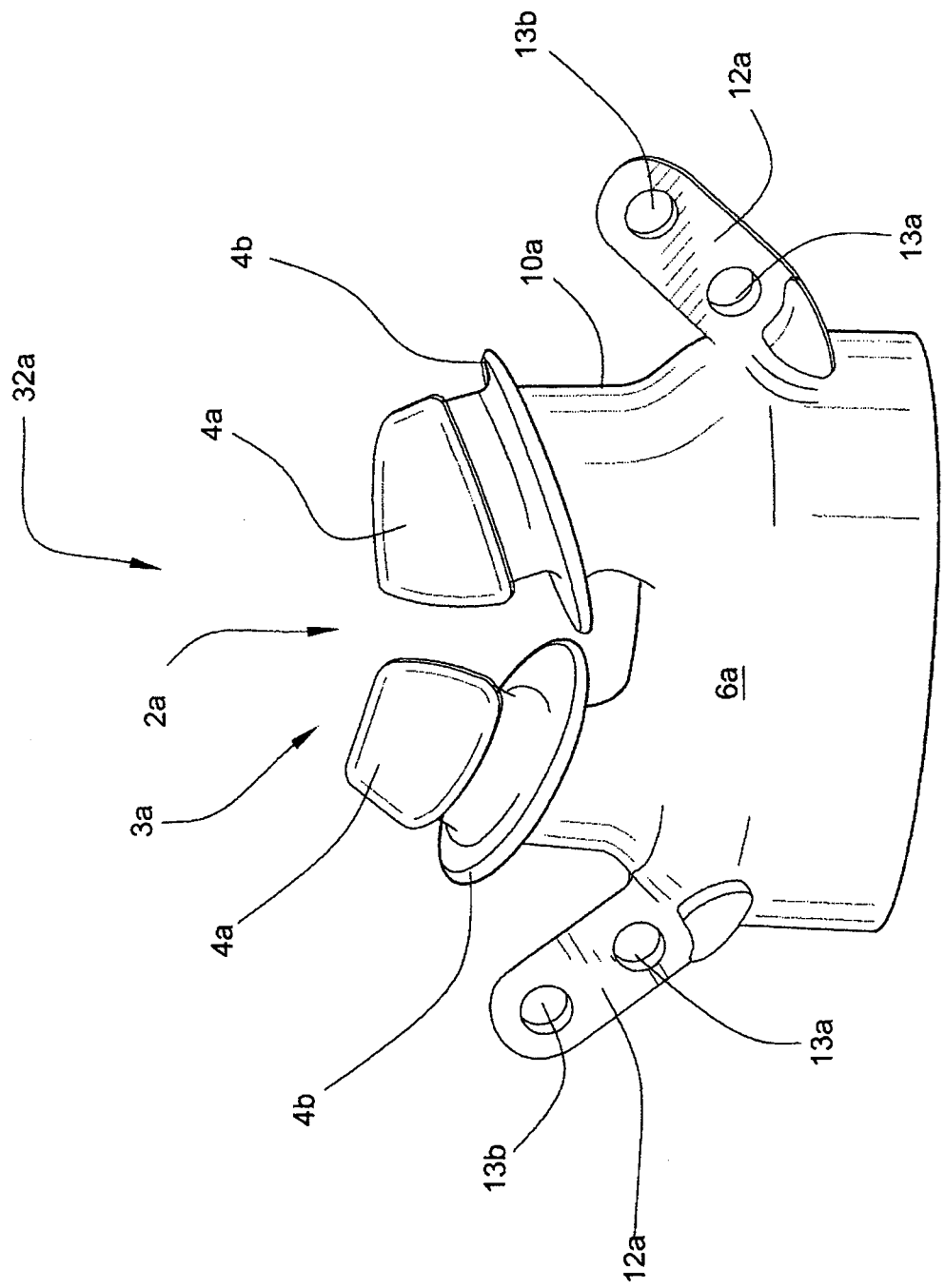
FIG. 5a schematically illustrates a patient interface system according to another sample embodiment.
Figure 6:
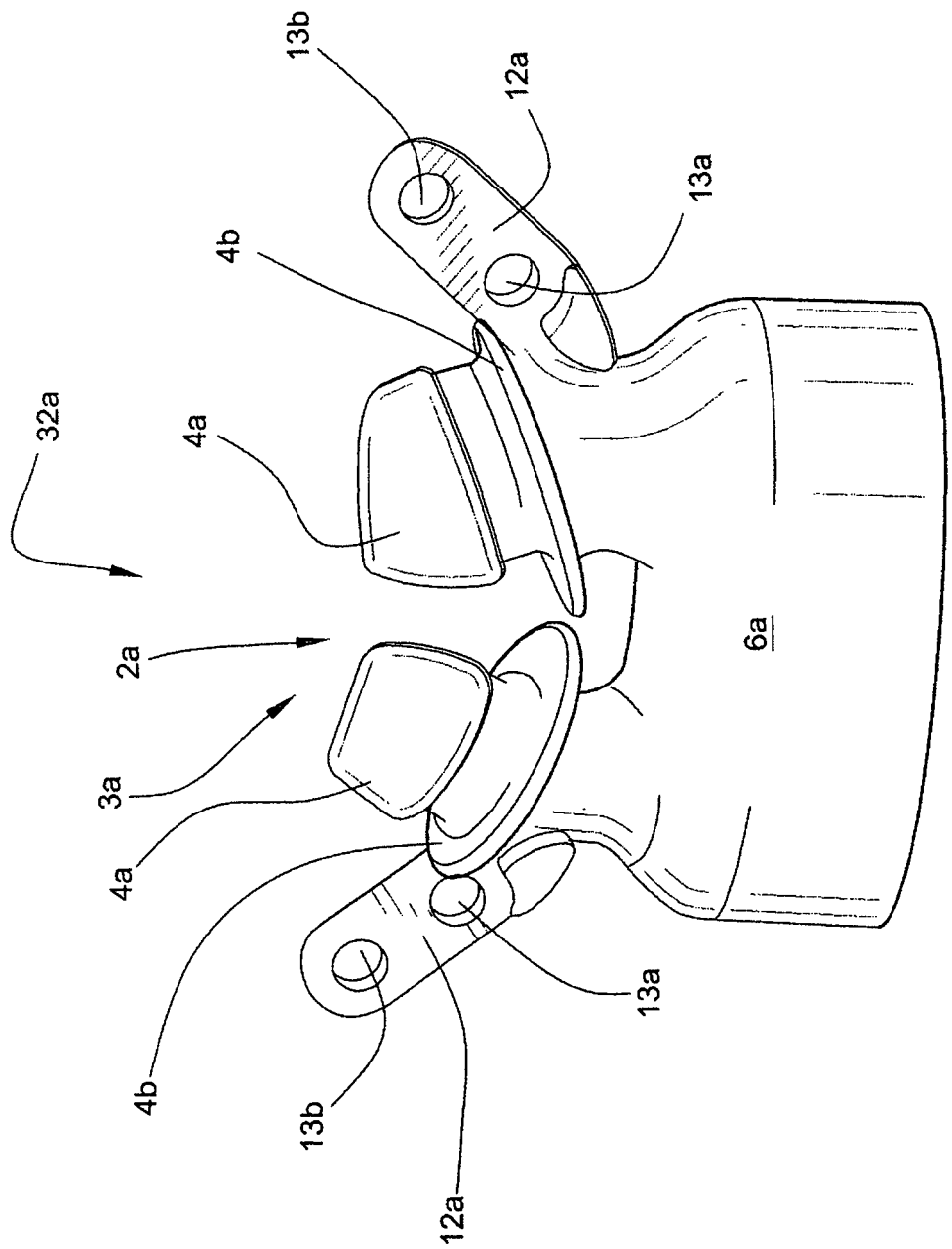
FIG. 6 schematically illustrates a patient interface system according to another sample embodiment.

FIGS. 5a and 6 illustrate an aspect of the present technology whereby the point of connection of the seal positioning and stabilizing structure is moved closer to the base of the seal, for example close to the base of nasal pillows or prongs. Referring to FIG. 5a, a patient interface system according to a sample embodiment includes a patient interface structure 32a comprising a seal 2a including a nozzle assembly 3a. The nozzle assembly 3a comprises a pair of nasal prongs 4a. Each nasal prong 4a includes a stalk, or neck portion, 10a that connects the nasal prong 4a to a flexible base 6a of the patient interface structure 32a. Flaps 4b are provided between the nasal prongs 4a and the stalks 10a. The nasal prongs 4a form a seal with the nasal passageways of the patient when the nozzle assembly 2a is held by a seal positioning and stabilizing structure in engagement with the face of the patient.

A pair of seal positioning and stabilizing structure connectors 12a are provided on a flexible base 6a of the patient interface structure 32a. Connectors 12a are provided on the flexible base 6a for the connection of straps of a seal positioning and stabilizing structure with the patient interface structure 32a.

The connectors 12a may include a plurality of connection points 13a, 13b to allow the relative position of the patient interface structure 32a with respect to the seal positioning and stabilizing structure 36 to be changed or adjusted.

Referring again to FIG. 2, a patient interface system may include the patient interface structure of FIG. 5a and a mask shell or frame as shown in FIG. 2 that is modified to not include the connectors on the frame and includes a vent having a plurality of vent holes. The mask frame may be connected to an air delivery tube by a swivel elbow. The ends of the swivel elbow may include ball and socket type connections to the frame and the air delivery tube so that the swivel elbow acts as a decoupling element or joint. The delivery tube may receive a flow of pressurized breathable gas by being connected through a coupling element to a flow generator or blower. It should be appreciated that the mask frame of FIG. 2 may be formed of a flexible material, instead of a rigid material as in the prior art shown in FIG. 2, and the connectors 12 may be provided on the flexible frame.

In another sample embodiment, the elbow may be flexible. In such a form, it may be desirable to locate the vent holes elsewhere on the mask system. Alternatively, a solid vent insert may be placed in the flexible elbow. In another form, reinforcement may be provided to the flexible elbow to maintain its structural integrity and prevent the tube from occluding.

Figure 2:
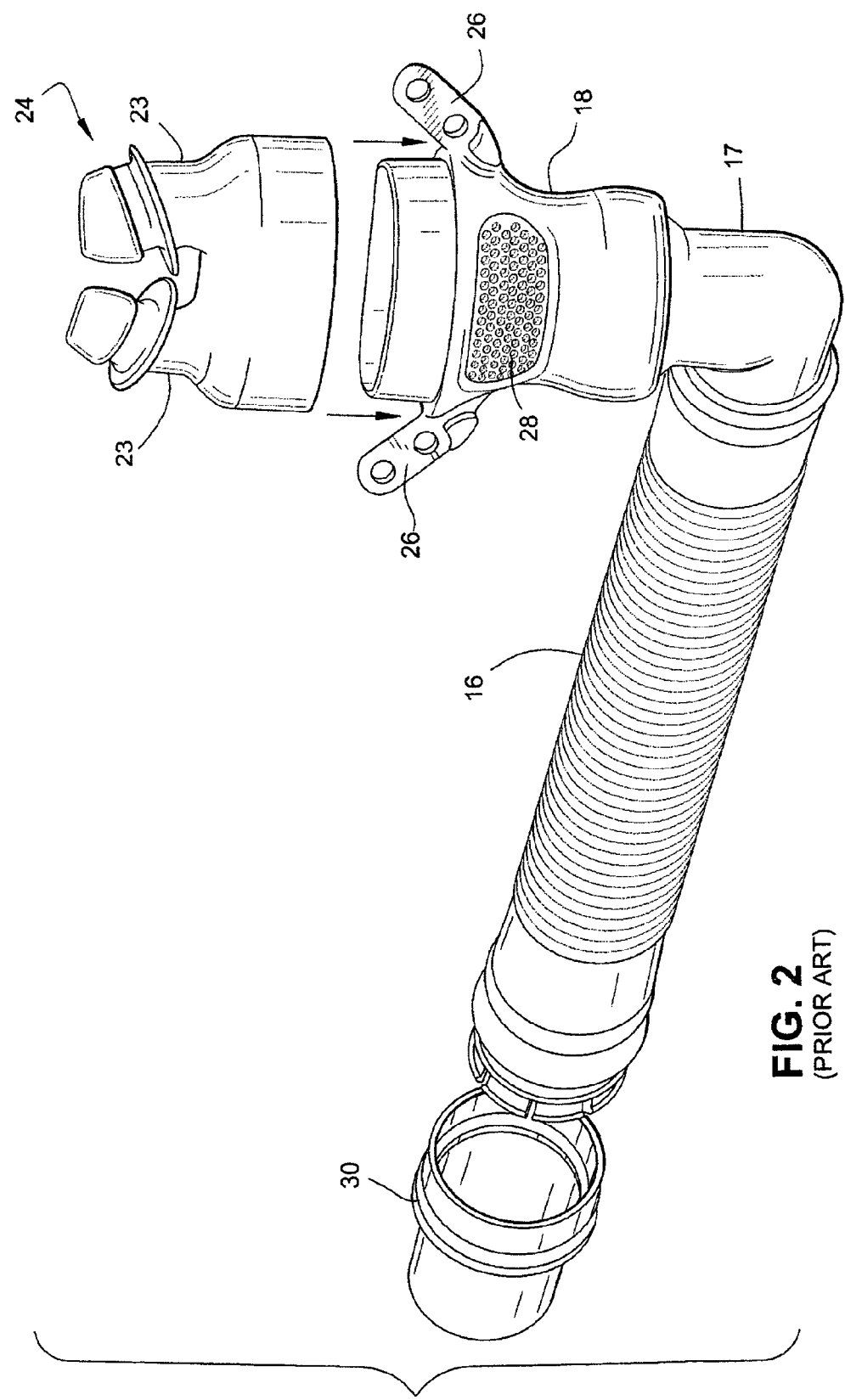
FIG. 2 schematically illustrates a patient interface system according to the prior art.

Patient Interface Structure Including Nasal Prongs Seal and Connectors on Nasal Prongs Referring to FIG. 6, in another sample embodiment, the seal positioning and stabilizing structure connectors 12a are provided at a point just below the flaps 4b of the nasal prongs 4a. The seal positioning and stabilizing structure connectors 12a are connected to the neck, or base, portions 10a of the nasal prongs 4a. According to this embodiment, the plane of connection formed by the seal positioning and stabilizing structure connectors 12a is closer to the plane of the entrance to the nares of the patient than the embodiment shown in FIG. 5a. The patient interface structure of FIG. 6 may also be used with a mask frame such as shown in FIG. 2 that is modified to not include connectors on the frame. It should also be appreciated that the patient interface structure of FIG. 6 may be used with a mask frame such as shown in FIG. 2 that is modified to be formed of flexible material.

3.2.4.1 Patient Interface Structure Including Linking Element—First Embodiment Referring to FIGS. 8a and 8b, a patient interface structure according 32 according to another sample embodiment may comprise a seal 2 comprising a nozzle assembly 3 having nasal pillows 4. The patient interface structure 32 may include an optional linking portion or element 47 configured to link tension forces applied by the seal positioning and stabilizing structure from one side of the patient interface structure 32 to the other side in order to isolate forces applied by the seal positioning and stabilizing structure at the top portion 6t of the flexible base 6, and thereby isolate tube drag forces at the lower portion 6l of the flexible base 6 of the patient interface structure 32. By isolating forces in such a way, the sealing zones 8a of the nasal pillows 4 of the seal 2 are stabilized against the patient's nares in use. In some forms of the technology, there may be no physical linking element. The line of force defined by the linking element is preferably close to the base of the nose when used in an under-the-nose type mask such as nasal pillows or nasal prongs.

As shown in FIG. 8a, the linking element 47 may take the form of a stiffened and/or reinforced top portion 6t when compared to the lower portion 6l of the flexible base 6. The lower portion 6l may include, or take the form of, a gusset, for example as disclosed in WO 01/97893. The gusset may also be configured similarly to an accordion, having multiple ridges to increase its springiness and flexibility, for example as disclosed in WO 2006/074515, the entire contents of which are incorporated herein by reference.

The gusset may also be reinforced to control where and how it collapses, i.e. so that it can move laterally and axially but cannot compress vertically. Reinforcement may include supporting ribs, thickened sections or regions, or a rigid or semi-rigid skeleton with a flexible material surrounding it.

Stiffening and/or reinforcing may be achieved by a thickening of the material used in the patient interface structure 32, for example increasing the thickness of the silicone by up to about 10 mm at the top portion 6t when compared to the lower portion 6l of the flexible base 6. Such stiffening and/or reinforcing may also be achieved through the use of a higher hardness material positioned at the top portion 6t, for example silicone of a durometer between about 50-80 on the Shore A hardness scale. Additionally, or alternatively, metal inserts, for example a wire(s) or mesh(es), may be used in the linking element 47. Stiffening and/or reinforcing may also be achieved by a gel insert. The gel insert may also increase patient comfort, for example at the septum. Furthermore, stiffening and/or reinforcing may also be achieved by a foam insert. The foam insert may increase patient comfort, for example at the septum, and act as a secondary seal should a leak form at the primary seal. The linking element 47 may also be formed of a co-molded, generally inextensible material, for example nylon, TPE, metal, or alloy. The linking element 47 may also be in the form of a beaded, thickened portion, as described in more detail below. Desirably, stiffening and/or reinforcing the top portion 6t, for example to form the linking element 47, will result in the lower portion 6l being more extensible so that forces applied by the seal positioning and stabilizing structure are more isolated from the lower portion 6l. This allows the lower portion 6l of the flexible base 6, for example the gusset, to flex more easily while ensuring that the nasal pillows 4 are held in sealing contact with the nares of the patient.

In another form, the linking element 47 may be configured in such a way that it is stiff along its length, e.g. from connector 50 to connector 50, but elastic through its height, i.e. in the general direction of the nasal pillows 4. This enables the neck portions 10 of the nasal pillows 4 to flex more readily while maintaining the primary function of the linking element 47, i.e. isolating the forces applied by the seal positioning and stabilizing structure.

In a variant, the linking element 47 may be formed from a material that can be molded to the patient's face, for example the plastic material used to form mouth guards. This would provide the benefit of isolating forces and increasing the comfort of the patient interface system due to its unique fit.

Patient Interface Structure Including Linking Element—Second Embodiment

As shown in the sample embodiment of the patient interface structure shown in FIG. 8a, the linking element 47 may extend across the entire top portion 6t of the flexible base 6, from connector 50 to connector 50, and including the entire width. See, for example, W1 in FIG. 17a. According to another sample embodiment of the patient interface structure 32 shown in FIG. 8c, the linking element 47 may extend over a section, or sections, of the top portion 6t of the flexible base 6, for example only the section of the top portion 6t between the nasal pillows 4. The linking element 47 may cover a fraction of the width of the top portion 6t, for example half the width. The tension linking element 47 may cover a section, or sections, of the top portion 6t as long as it is sufficient to isolate the forces as described above.

Patient Interface Structure Including Linking Element—Third Embodiment

Referring to FIG. 8d, the linking element may be formed as a series of ridges 47a. The number of ridges 47a may be determined in order to sufficiently isolate forces as described above. As shown in FIG. 8d, the ridges 47a may be provided to the top portion 6t only between the nasal pillows 4. The ridges 47a may be thicker than the top portion 6t. The ridges 47a may be generally circular or rectangular or any other shape. The ridges 47a may extend upwards and/or downwards from the top portion 6t. The ridges 47a may also be formed from a material of higher hardness than that used to form top portion 6t, for example higher durometer silicone, or metal. The ridges 47a may be formed in one piece with the patient interface structure 32, or may be retrofitted to the patient interface structure 32. For example, the linking element, e.g. the ridges 47a, may be adhesively attached to the patient interface structure 32. The ridges 47a may also be independent of one another, or the ridges 47a may be joined together. In the case of the linking elements comprising inserts, the inserts may be separately provided, or connected together. The ridges 47a may also be formed of individual shapes, sizes, thicknesses, materials, and/or hardnesses.

Patient Interface Structure Including Linking Element—Fourth Embodiment

Referring to FIG. 8e, the ridges 47a may be provided to the top portion 6t along the entire length of the flexible base 6, i.e. from connector 50 to connector 50.

Patient Interface Structure Including Linking Element—Fifth Embodiment

Referring to FIG. 8f, the linking element 47 may be formed in the top portion 6t of the flexible base 6 of the patient interface structure 32. For example, the patient interface structure 32 may be molded around the linking element 47 so that the linking element 47 is embedded within the top portion 6t of the flexible base portion 6 of the patient interface structure 32. The linking element 47 may be formed, for example, of metal or plastic material. The linking element may also be in the form of, for example, a wire or a mesh.

Patient Interface Structure Including Linking Element—Sixth Embodiment

Referring to FIGS. 8g and 8h, according to another sample embodiment, the linking element 47 may be provided along the top portion 6t of the flexible base 6. The linking element 47 may include slots or openings 47o that correspond with the first and second slots 52, 54 of the connector 50 to accept the straps of the seal positioning and stabilizing structure that connect to the patient interface structure 32. As shown in FIG. 8h, the linking element 47 may have an outline that matches the top portion 6t of the flexible base 6 of the patient interface structure 32 and comprise openings 47p that are configured to receive the stalks or neck portions 10 of the pillows 4. The linking element 47 may also include slits 47s that allow the portions of the linking element 47 around the openings 47p to be displaced with respect to one another to insert the linking element 47 over the pillows 4 and onto the top portion 6t of the flexible base 6.

The element 47 may be formed of, for example, metal or plastic. For example, the linking element 47 may be a thin metal sheet that is stamped into the configuration shown in FIG. 8h. It should also be appreciated that the connectors 50 of the patient interface structure 32 may be eliminated and the straps of the seal positioning and stabilizing structure connected directly to the linking element 47 without any direct connection to the patient interface structure 32.

Patient Interface Structure Including Linking Element—Seventh Embodiment

Referring to FIGS. 8i and 8j, a linking element 47 may extend around the neck portions 10 of the pillows 4. As shown in FIG. 8j, the linking element 47 may have a figure eight configuration and include openings 47p that are configured to receive the neck portions 10 of the pillows 4. The linking element 47 may be formed from, for example, metal or plastic. For example, the linking element 47 may be formed from a wire.

Patient Interface Structure Including Linking Element—Eighth Embodiment

Referring to FIG. 8k, according to another sample embodiment, the linking element 47 may comprise a bridging portion between the stalks or neck portions 10 of the nasal pillows 4. The linking element 47 may be integrally formed, e.g. by molding, with the patient interface structure 32. The linking element 47 may also be formed of a different material than the material used to form the patient interface structure 32. For example, the linking element 47 may be formed of a higher durometer material than the patient interface structure material. The linking element 47 may be formed to be more rigid than the top portion 6t of the flexible base 6 of the patient interface structure 32.

Nasal Pillow Seals—Offset

Figure 27A:
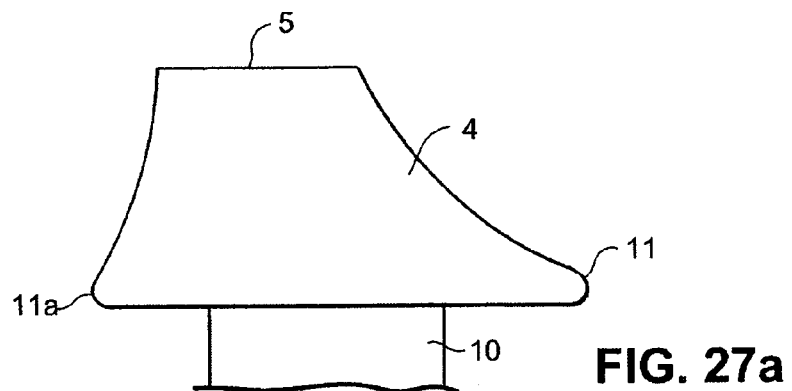
FIGS. 27a and 27b schematically illustrate a nasal pillow according to another sample embodiment.
Figure 27B:
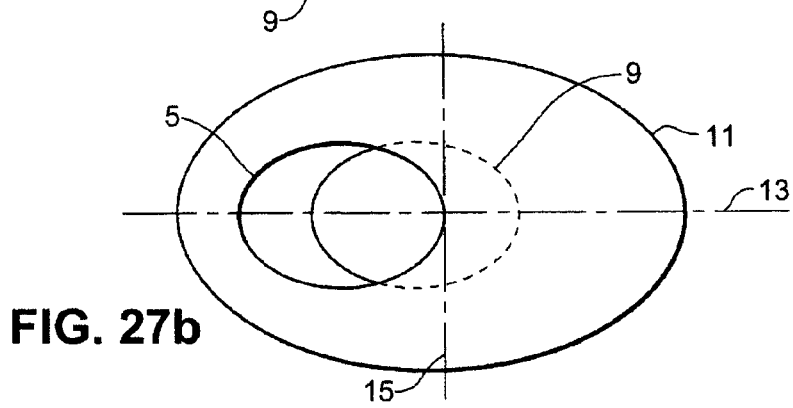

Referring to FIGS. 27a and 27b, each nasal pillow 4 may comprise a pillow orifice 5 for delivering breathable gas to the nares of the patient. Each pillow 4 is inserted into a nare of the patient and is sealed at a sealing surface 11. As shown in FIG. 27b, the pillow orifice 5 is offset from a neck orifice 9 of the stalk or neck portion 10 along a major axis 13 of the elliptically shaped nasal pillow 4 by shifting the pillow orifice 5 along the major axis 13. The portion 11a of the sealing surface 11 that is in contact with the upper lip of the patient is thus reduced, which may increase patient comfort. Although the pillow orifice 5 is shown shifted from the neck orifice 9 along the major axis 13, it should be appreciated that the pillow orifice 5 may be shifted along the major axis 13 and/or the minor axis 15.

Nasal Pillows Seal Including Dual Walls

Figure 17A:
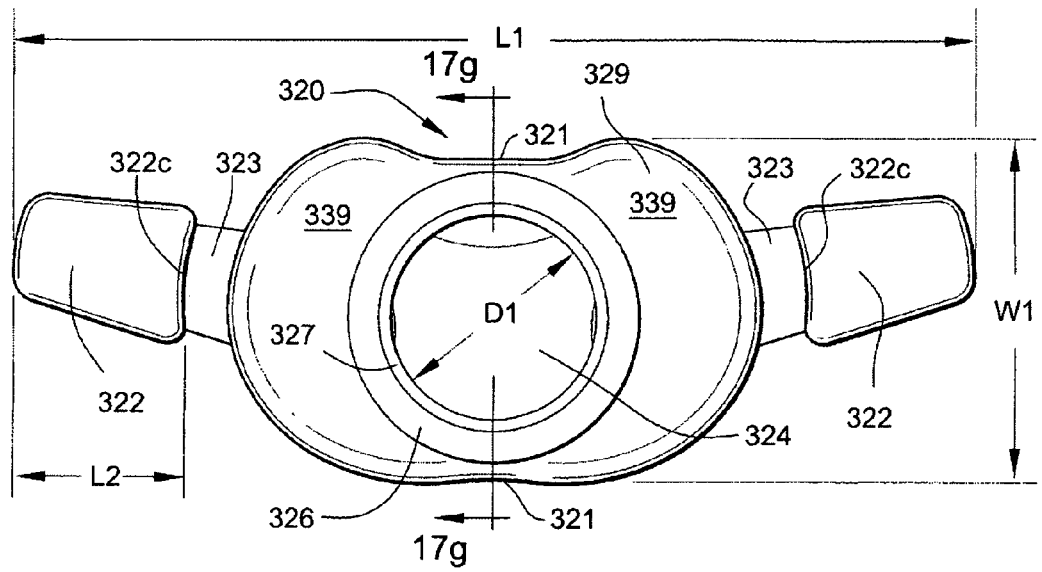
FIGS. 17a-17g schematically illustrate a sample embodiment of a patient interface structure according to sample embodiments.
Figure 17B:
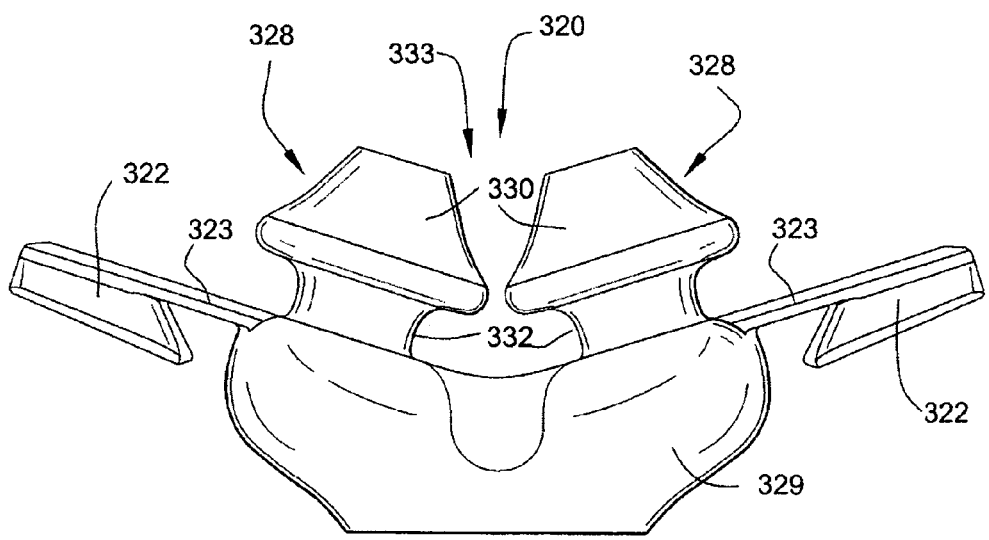
Figure 17C:
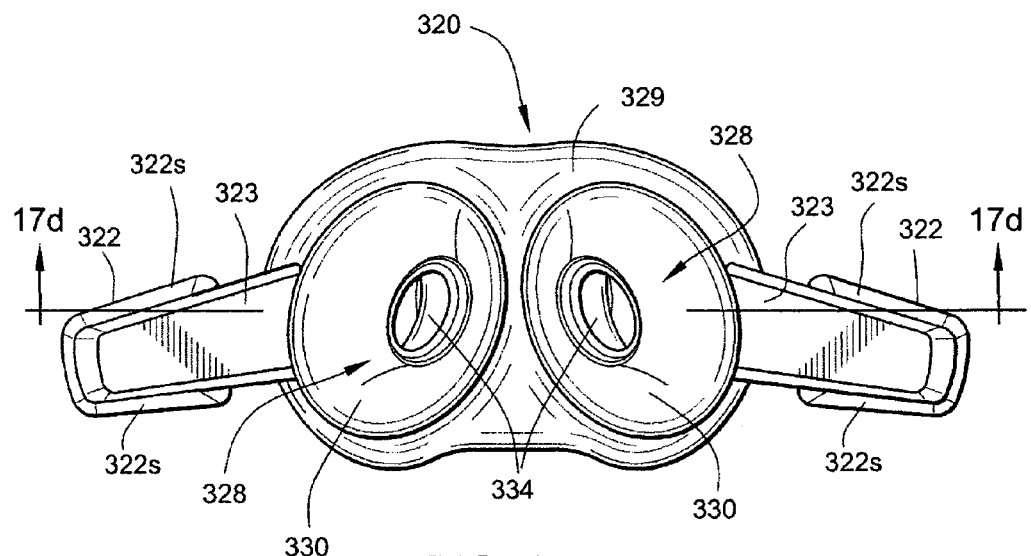
Figure 17D:
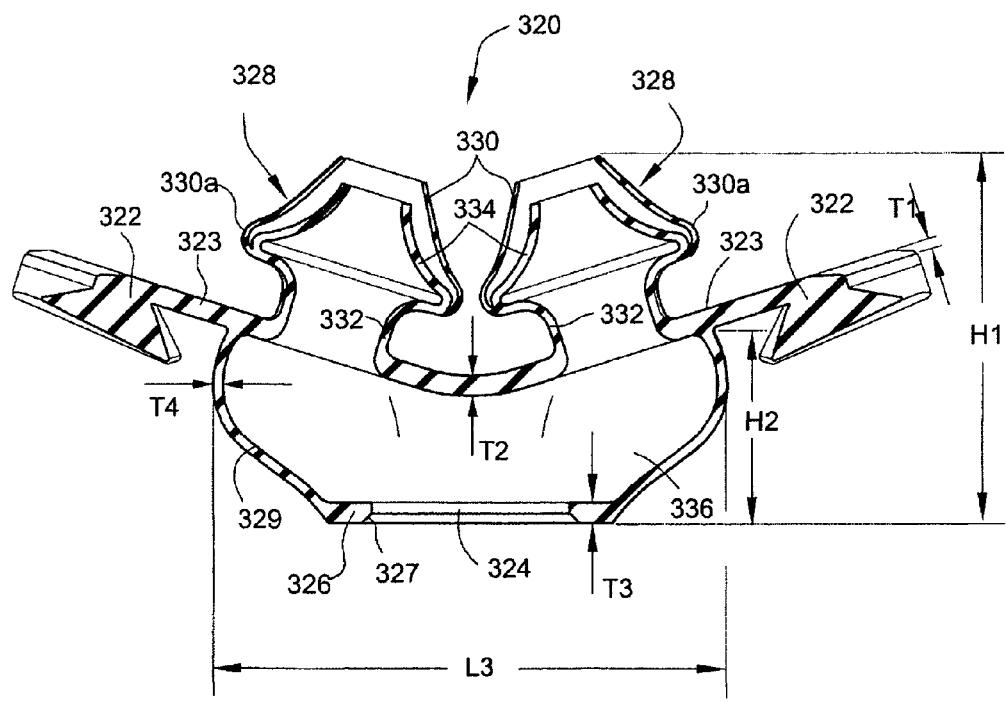

Referring to FIGS. 17a-17f, a patient interface structure 320 includes connectors 322 on each side and connected to a flexible base 329 of the patient interface structure 320 by extensions 323. It should be appreciated that the connectors 322 may be connected by the extensions 323 to respective neck portions 332 of a pair of nozzles 328 in a manner similar to that discussed above with respect to FIG. 6. The connectors 322 may be linear with the upper surface of the flexible base 329 (as shown in FIGS. 17b and 17d). Alternatively, the connectors 322 may be tilted or angled to alter the position of the patient interface structure 320 when connected to the seal positioning and stabilizing structure.

Figure 17E:
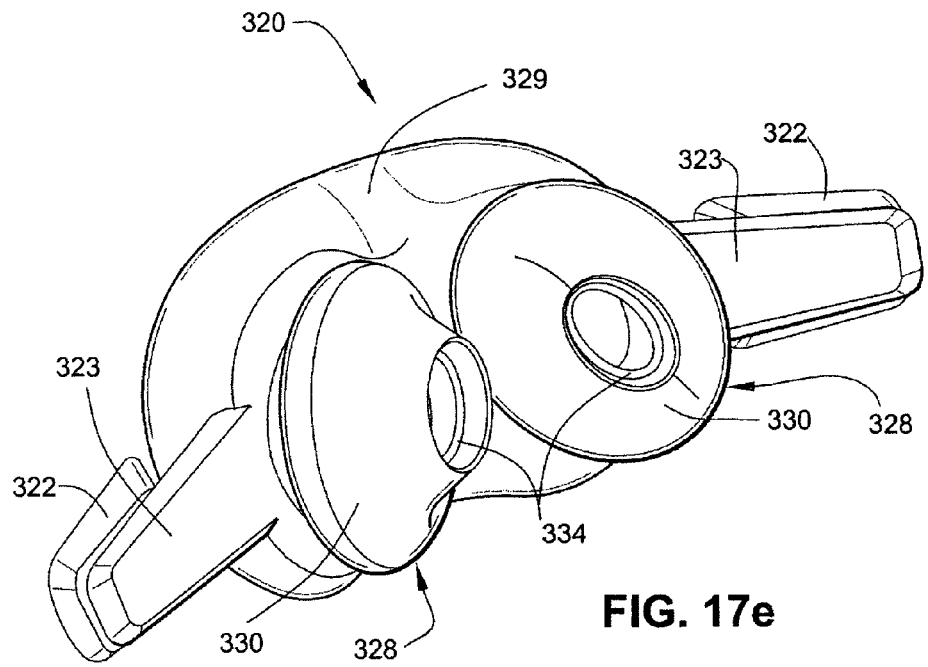

The patient interface structure 320 comprises a seal 333 comprising a nozzle assembly comprising the pair of nozzles taking the form of nasal pillows 328. As shown in FIGS. 17b and 17d, the pillows 328 each comprise a neck portion 332 that is connected to the flexible base 329 that defines a nasal breathing cavity 336. As also shown in FIGS. 17d and 17e, each nasal pillow 328 comprises an inner conical portion 334 and an outer conical portion 330. Such pillows are disclosed, for example, U.S. Patent Application Publications 2007/0144525 A1 and 2006/0283461 A1, the entire contents of each being incorporated herein by reference. It should also be appreciated that the nasal pillows may be as described in, for example, U.S. Pat. No. 7,318,437, the entire contents of which are incorporated herein by reference. The outer conical portion 330 comprises a sealing surface, or zone, 330a that is configured to seal against the patient's nare. As shown in FIG. 17d, the inner conical portion 334 and the outer conical portion 330 may have different thicknesses.

Figure 17F:
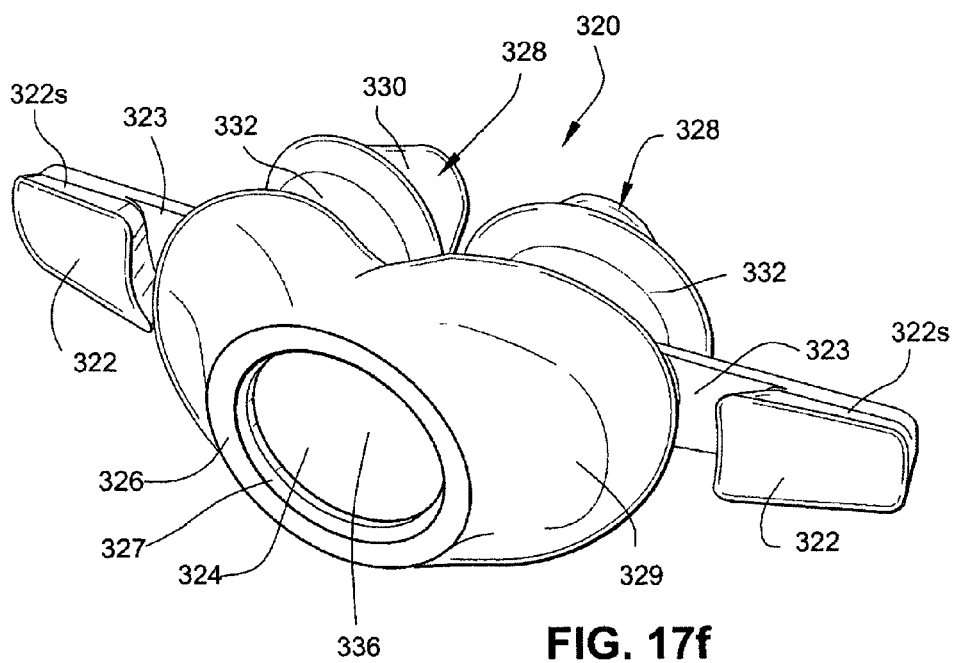
Figure 17G:
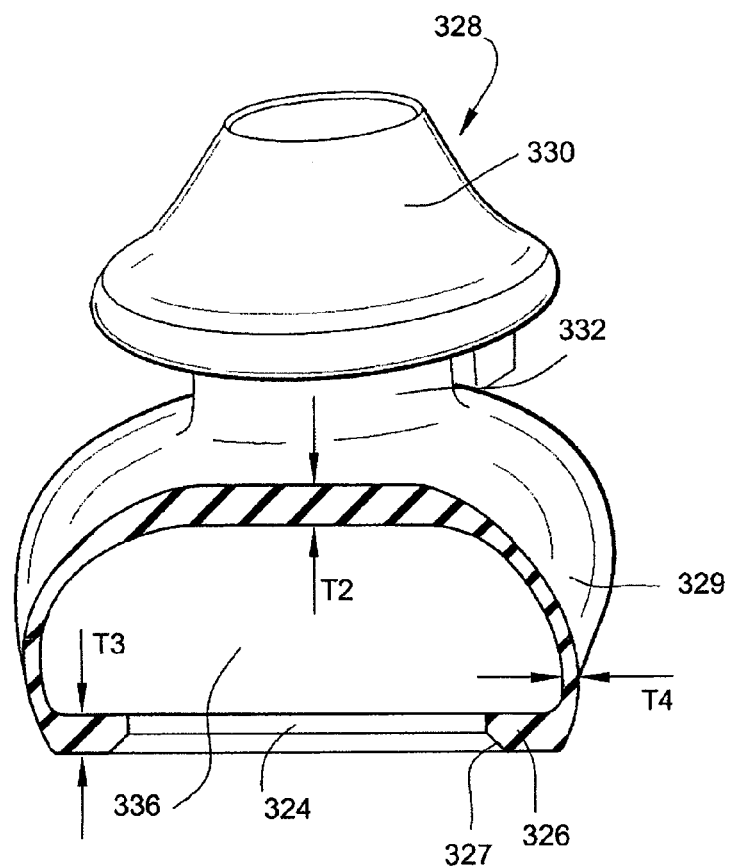

Referring to FIGS. 17d, 17f and 17g, the flexible base 329 includes an aperture 324 for the introduction of the flow of breathable gas. The flexible base 329 further comprises a flange 326 that extends radially inwardly and defines the aperture 324. The flange 326 may comprise a chamfer 327 for insertion of a swivel sealing ring as discussed in more detail below. The flexible base 329 of the patient interface structure 320 may thus be connected to a frame, a swivel elbow, or a tube or conduit as also described in more detail below.

It should also be appreciated that the flexible base 329 may include a linking element(s), similar to the one disclosed and discussed with respect to FIGS. 8a-8g, for example in between the neck portions 332 of the nasal pillows 328.

Referring to FIG. 17a, the aperture 324 may have a diameter D1 of about 17 mm-20 mm, for example about 18.5 mm. The patient interface structure 320 may have a width W1 of about 25 mm-35 mm, for example about 30.5 mm. The patient interface structure 320 may have a length L1 of about 80 mm-90 mm, for example about 84.5 mm. The seal positioning and stabilizing structure connector 322 may have a length of about 12 mm-18 mm, for example about 15.5 mm.

Referring to FIG. 17d, the flexible base 329 may have a length L3 of about 45 mm-50 mm, for example about 47.5 mm. The patient interface structure 320 may be a height H1 of about 30 mm-37 mm, for example about 33 mm. The base portion 329 may have a height H2 of about 15 mm-23 mm, for example about 19 mm.

Referring to FIGS. 17d and 17g, the extensions 323 may have a thickness T1 of about 1.5 mm-2.0 mm, for example about 1.8 mm. The flexible base 329 may have a thickness T2 between the nasal pillows 328 of about 1.5 mm-2.5 mm, for example about 2.0 mm. It should be appreciated that the thickness T2 may be greater, for example in the case where a linking element is formed in one piece with the patient interface structure 320 between the nasal pillows 328. The flange 326 may have a thickness T3 of about 1.5 mm-2.5 mm, for example about 2.0 mm. The flexible base 329 may have a thickness T4 of about 0.6 mm-1.0 mm, for example about 0.8 mm.

The stalks 32 may have a length of about, for example, 3 mm to about 6 mm.

Nasal Pillows Seal Including Dual Walls—Equal Displacement and Non-Concentric

Referring to FIGS. 28a and 28b, the pillows 328 may comprise the outer conical portion 330 and the inner conical portion 334. A portion 360a of a sealing zone 360 of the outer conical portion 330 that is in contact with the upper lip of the patient is displaced an equal distance 362 from the stalk or neck portion 332 of the pillow 328 as a portion 360b of the sealing zone 360 that is in sealing engagement with the nares of the patient. The sealing zone 360 and the pillow orifice 354 are non-concentric with the stalk 332 of the pillow 328.

Nasal Pillows Seal Including Dual Walls—Unequal Displacement and Concentric

Referring to FIGS. 29a and 29b, the portion 360a of the sealing zone 360 that engages the upper lip of the patient is displaced a distance 364 that is not equal to the distance 366 that the portion 360b is displaced from the stalk 332. The pillow orifice 354 and the sealing zone 360 are concentric with the stalk 332.

Nasal Pillows Seal Including Dual Walls—Unequal Displacement and Concentric with Supporting Rib Referring to FIGS. 30a and 30b, the portion 360a is displaced an unequal amount from the stalk 332 than the sealing zone portion 360b. The sealing zone 360 and the pillow orifice 354 are concentric with the stalk 332. A supporting rib 368 may be provided under the portion 360b of the sealing zone 360 to maintain the pillow sealing zone in an upright position so that it may seal at the nares.

Nasal Pillows Seal Including Dual Walls—Concentric and Angled

As shown in FIGS. 31a and 31b, the inner conical portion 334 and the outer conical portion 330 are tilted at an angle 370 with respect to the stalk 332 of the pillow 328. The angle tilts the pillow towards the face of the patient and may be, for example, −30° to 45°, as another example 15°. The portion 360a configured to engage the upper lip of the patient has a larger radius than the sealing zone portion 360b to provide for greater patient comfort. The pillow orifice 354 and the sealing zone 360 are eccentric with respect to the stalk 332.

Nasal Pillows Seal Including Dual Walls—Symmetrical, Concentric and Angled

Referring to FIGS. 32a-32f, the orifice of the inner conical surface 1100, the outer 1000 walls and stalk 1200 of the nasal pillow 1150 are concentric with respect to a center line CL. The radius of the portion 1600 on the opposite side to portion 1500 is smaller than the radius of the portion 1500 that is adjacent to the upper lip of the patient. The larger radius of portion 1500 has a thickened region 1550 that assists in avoiding contact between the nasal pillow and the top lip, pushing the structure away therefrom. Avoiding contact with the top lip can improve comfort for some patients. An advantage of this is that the need to provide a separate manual pillows rotation mechanism may be reduced since the pillow may automatically move away from the top lip, adjusting to the naso-labial angle of the patient. This may in part be assisted by flexure of the patient interface structure connectors 84 of the seal positioning and stabilizing structure.

Figure 32A:
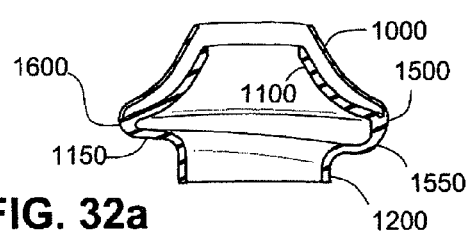
FIGS. 32a-32f schematically illustrate a nasal pillow according to another sample embodiment.
Figure 32B:
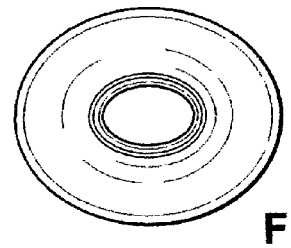
Figure 32C:
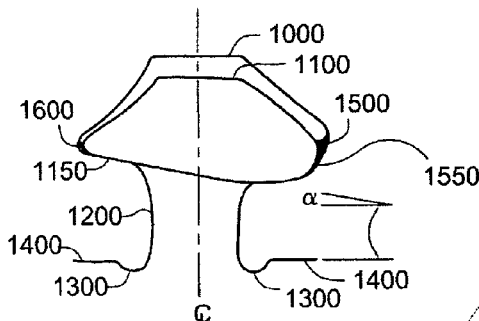
Figure 32D:
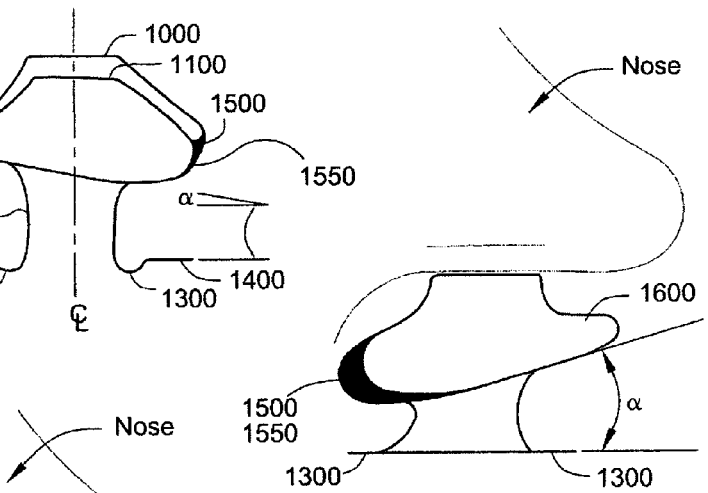
Figure 32E:
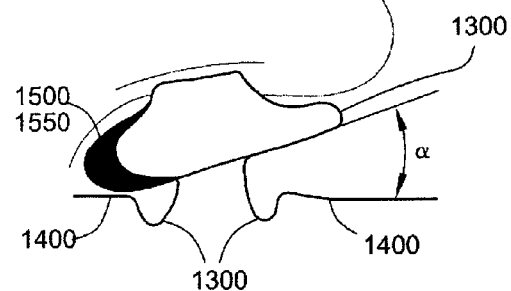
Figure 32F:
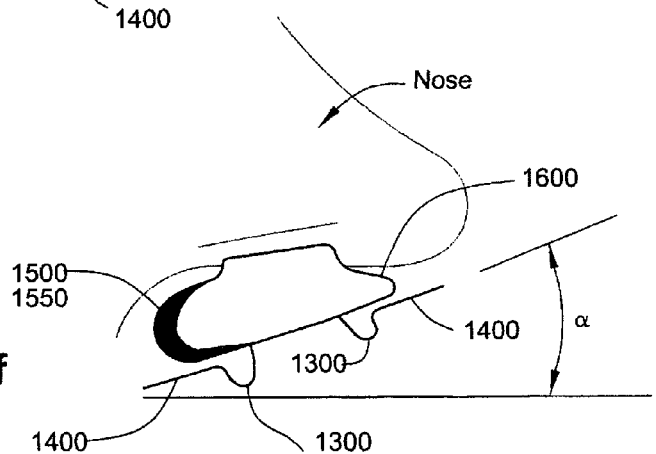

The base of the pillow 1150 is angled with respect to the top of a linking element 1400. The angle $\alpha$ allows the linking element 1400 to tilt. Referring to FIG. 32d, to engage the pillows 1150 with and entrance to the patient's airways, the pillows are placed at the entry to the nares. As shown in FIG. 32e, as the seal positioning and stabilizing structure is adjusted, strap tension begins to pull the pillows into the nares. Continued insertion of the pillows into the nares causes the stalk 1200 to collapse into the linking element 1400 via trampoline 1300, moving the linking element 1400 into contact with base of pillows 1150.

The thickened region 1550 results in a relatively stiffer spring structure than the thinner portion 1600 that may rotate the patient interface structure away from the top lip. Since the base of the pillow 1150 is angled a with respect to the linking element 1400, the linking element 1400 aligns with the base of the pillow 1150 so that they are flush or in constant contact along the whole surface of the base of the pillows 1150. This means that the linking element 1400 and adjacent trampoline 1300 rotates upwards, i.e. rotates by $\alpha°$ towards the top of the patient's nose. The linking element 1400 and the trampoline 1300 are thereby angled away from the bottom of the pillows or upper lip of the patient. This improves the comfort and stability of the patient interface system.

The rotation of the trampoline 1300 and the linking element 1400 away from the patient's upper lip could similarly be achieved by skewing the shape of the trampoline 1300 and/or linking element 1400 (e.g. by altering the dimensions of the flexible base of the patient interface structure), change the trampoline properties so that it is stiffer in some regions compared to other regions to force the stalk to collapse in a certain way (e.g. stiffer towards the bottom of the pillows/upper lip side) or changing the properties of the stalk to cause it to collapse more in one direction than another (e.g. stiffer towards the bottom of the pillows/upper lip side).

Nasal Pillows Seal Including Dual Walls—Offset Inner and Outer Conical Portions Referring to FIGS. 33a and 33b, the nasal pillows 328 may comprise elliptical inner and outer conical portions 334, 330, respectively. As shown in FIGS. 33a and 33b, the orifices 354, 355 of the inner and outer conical portions 334, 330, respectively, may be offset along a major axis of the ellipses. The radius of the portion 360a of the sealing zone 360 configured to engage the upper lip of the patient is larger than the radius of the portion 360b configured to seal the nare of the patient.

Nasal Pillows Seal—Truncated

Referring to FIG. 34, the pillows 328 may be provided with cut outs, or truncated portions, 350 for improved upper lip comfort of the patient. As shown in FIG. 35, according to one variant, the pillow orifice 354, the sealing zone 360, and the stalk 332 are concentric. The upper lip contacting side of the pillow 328 includes a truncated portion 350 to prevent interference and discomfort.

Figure 36:
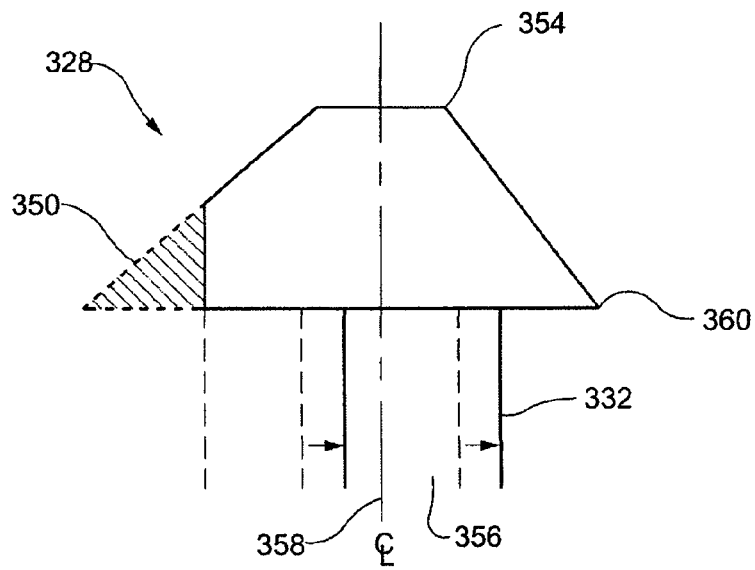
FIG. 36 schematically illustrates a nasal pillow according to another sample embodiment.
Figure 37:
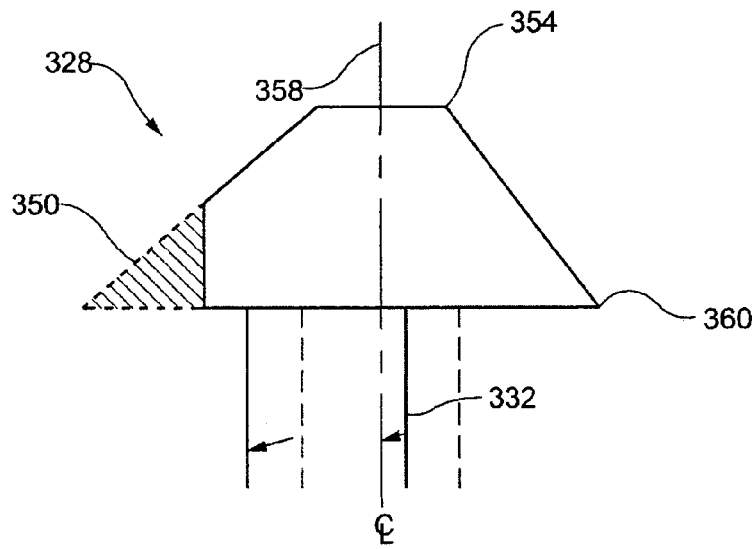
FIG. 37 schematically illustrates a nasal pillow according to yet another sample embodiment.

As shown in another variant illustrated in FIG. 36, the pillow orifice 354 and the sealing zone 360 are concentric along the centerline 358. The stalk 332 is not concentric with the centerline 358 so that the stalk orifice 356 is offset from the pillow orifice 354. As shown in FIG. 36, the stalk 332 may be offset in a direction away from the truncated portion 350. In a further variant shown in FIG. 37, the stalk 332 may be offset in a direction towards the truncated portion 350.

Nasal Pillows Seal—Coincident Sealing Surface and Stalk

Figure 38A:
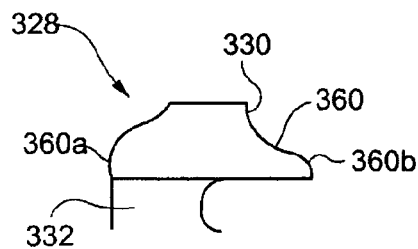
FIGS. 38a and 38b schematically illustrates a nasal pillow according to another sample embodiment.
Figure 38B:
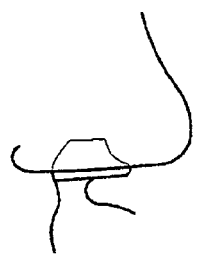
Figure 39A:
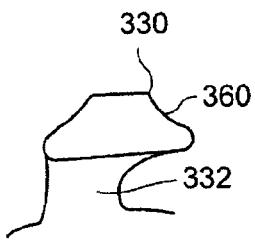
FIGS. 39a-39h schematically illustrate nasal pillows according to other sample embodiments.
Figure 39B:
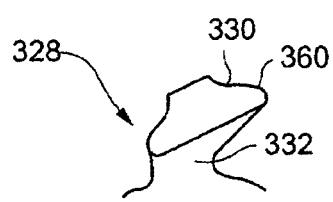
Figure 39C:
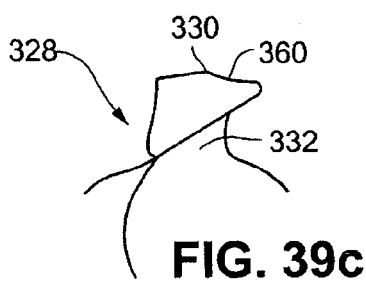
Figure 39D:
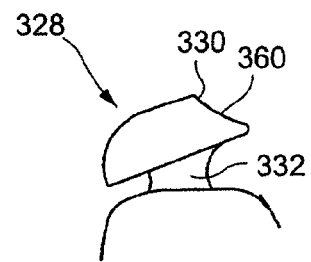
Figure 39E:
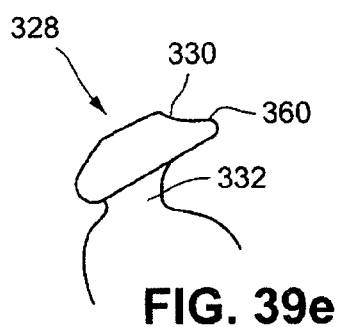
Figure 39F:
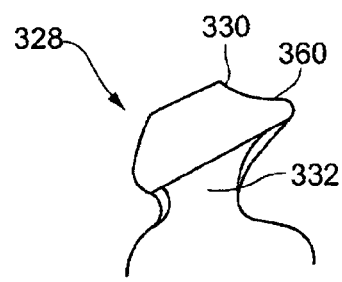
Figure 39G:
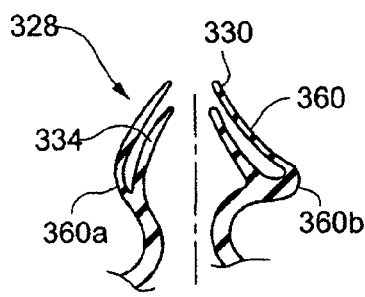
Figure 39H:
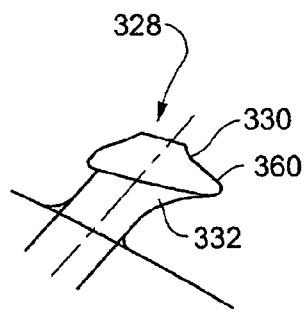

As shown in FIGS. 38a and 38b, the stalk 332 may be provided at a position coincident with the portion 360b of the sealing zone 360 that is configured to engage the patient's upper lip.

Nasal Pillows Seal—Bent Stalk and/or Sealing Surface

Referring to FIGS. 39a-39h, the outer conical portion 330 of the pillow 328 may be provided at an angle with respect to the stalk 332 and/or the stalk may be angled and/or have a variable cross section.

Nasal Pillows Seal—Rose Bud

Figure 40:
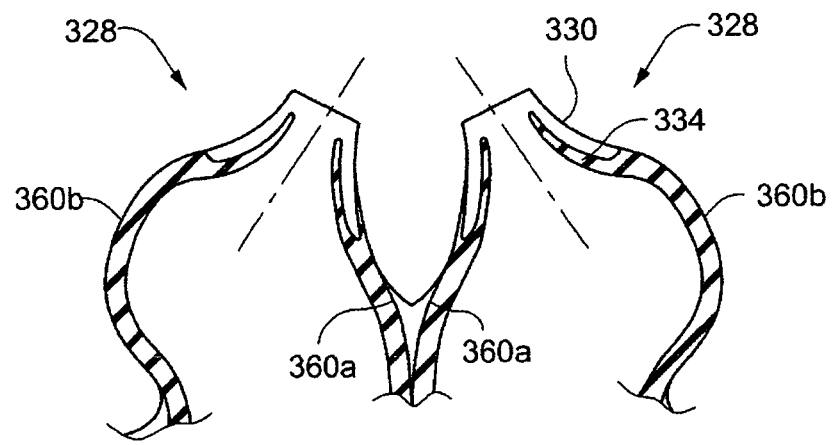
FIG. 40 schematically illustrates a nasal pillow configuration according to another sample embodiment.

As shown in FIG. 40, the nasal pillows 328 may be conjoined. The portions 360a of the sealing zones configured to contact the patient's upper lip may have a shallow radius and the portions 360b configured to engage the nares may have a large radius at the outer edges of the sealing zones to increase the fit range of the pillows. The pillows 328 may have a generally rose bud shaped configuration, as shown in the drawings.

Nasal Pillows Seal—Olive

Figure 41:
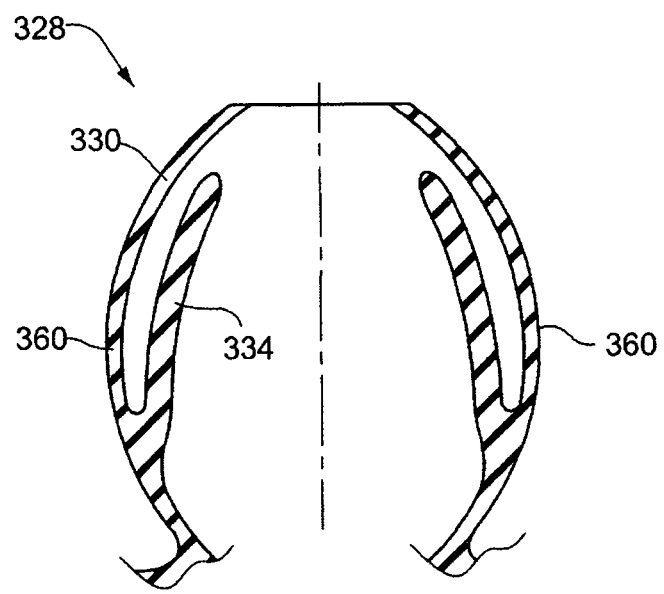
FIG. 41 schematically illustrate a nasal pillow according to another sample embodiment.

Referring to FIG. 41, the sealing zone of the pillow may have a large radii on either side, or both sides. The pillow may act as a nasal dilator. As shown in the drawings, the pillows 328 may have a generally olive shaped configuration.

Patient Interface Structure Including Foam Seal

Referring to FIGS. 45a-45e, a patient interface system according to another sample embodiment includes a patient interface structure 32 that includes a flexible base 6. A seal 2 is provided on the flexible base 6. The seal 2 may be formed of foam. A swivel elbow 17 is connected to the flexible base 6 for delivery of a flow of breathable gas from a hose or tube or conduit (not shown) connected to the swivel elbow 17 into a nasal breathing cavity defined by the flexible base 6 and the seal 2.

The patient interface structure 32 is held in sealing engagement with the patient's face by a seal positioning and stabilizing structure 36 that comprises side straps 38, a top strap 40 (FIG. 45c), and a rear strap (not shown). Although the side straps 38 are shown connected to the flexible base 6 in an integral fashion, it should be appreciated that the side straps 38 may be connected to the flexible base 6 in a manner that allows connecting and disconnecting the side straps 38 from the flexible base 6, for example as discussed in more detail herein. It should also be appreciated that one, or both, side straps 38 may be configured to be connectable and disconnectable from the flexible base 6.

Figure 45A:
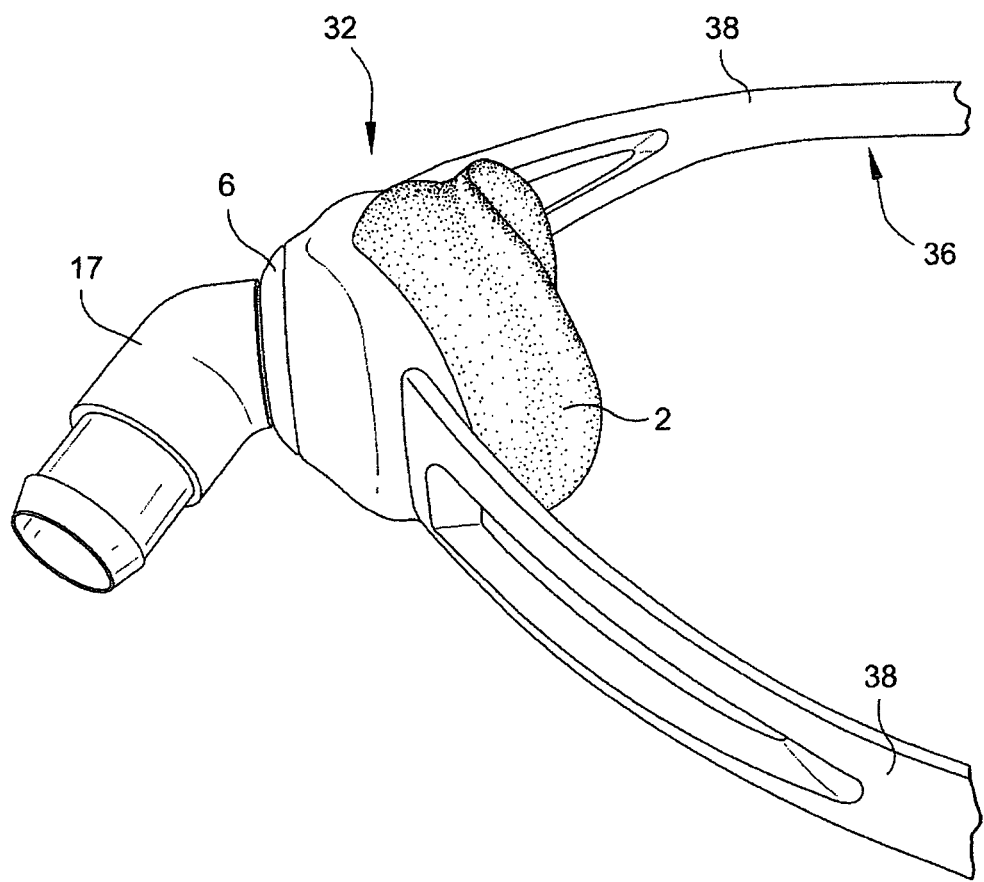
FIGS. 45a-45e schematically illustrate a patient interface system according to a sample embodiment.
Figure 45B:
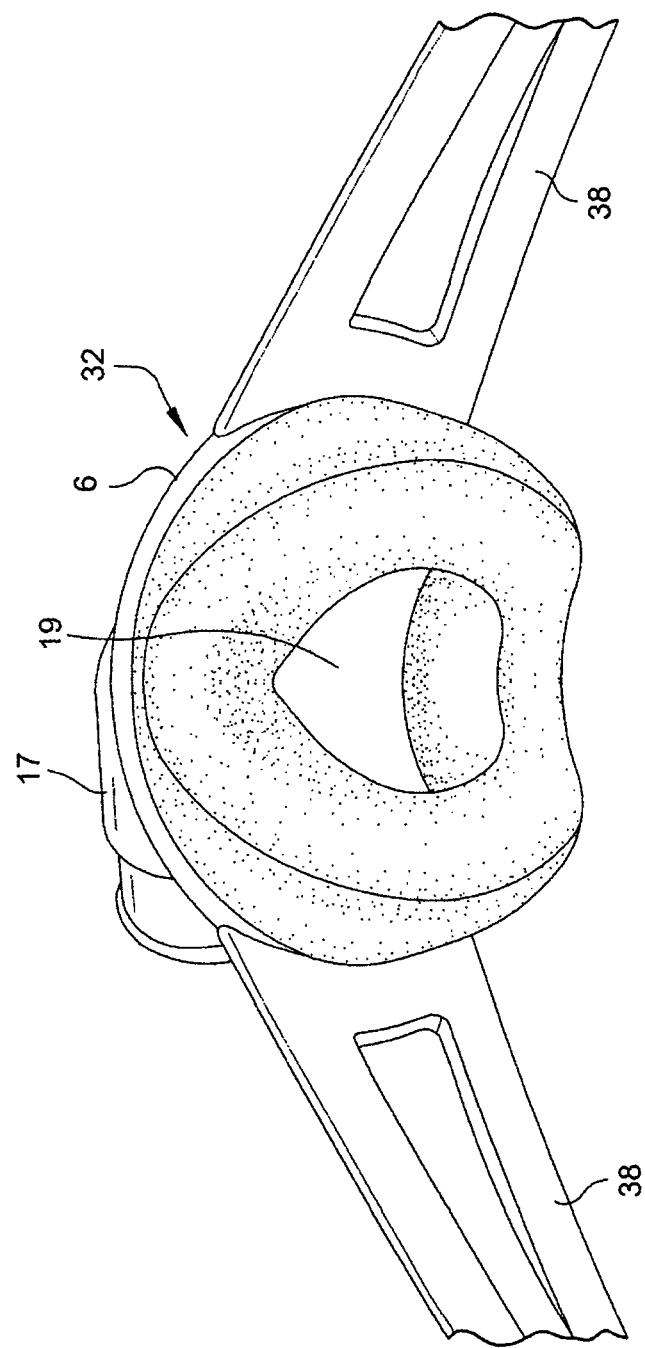
Figure 45C:
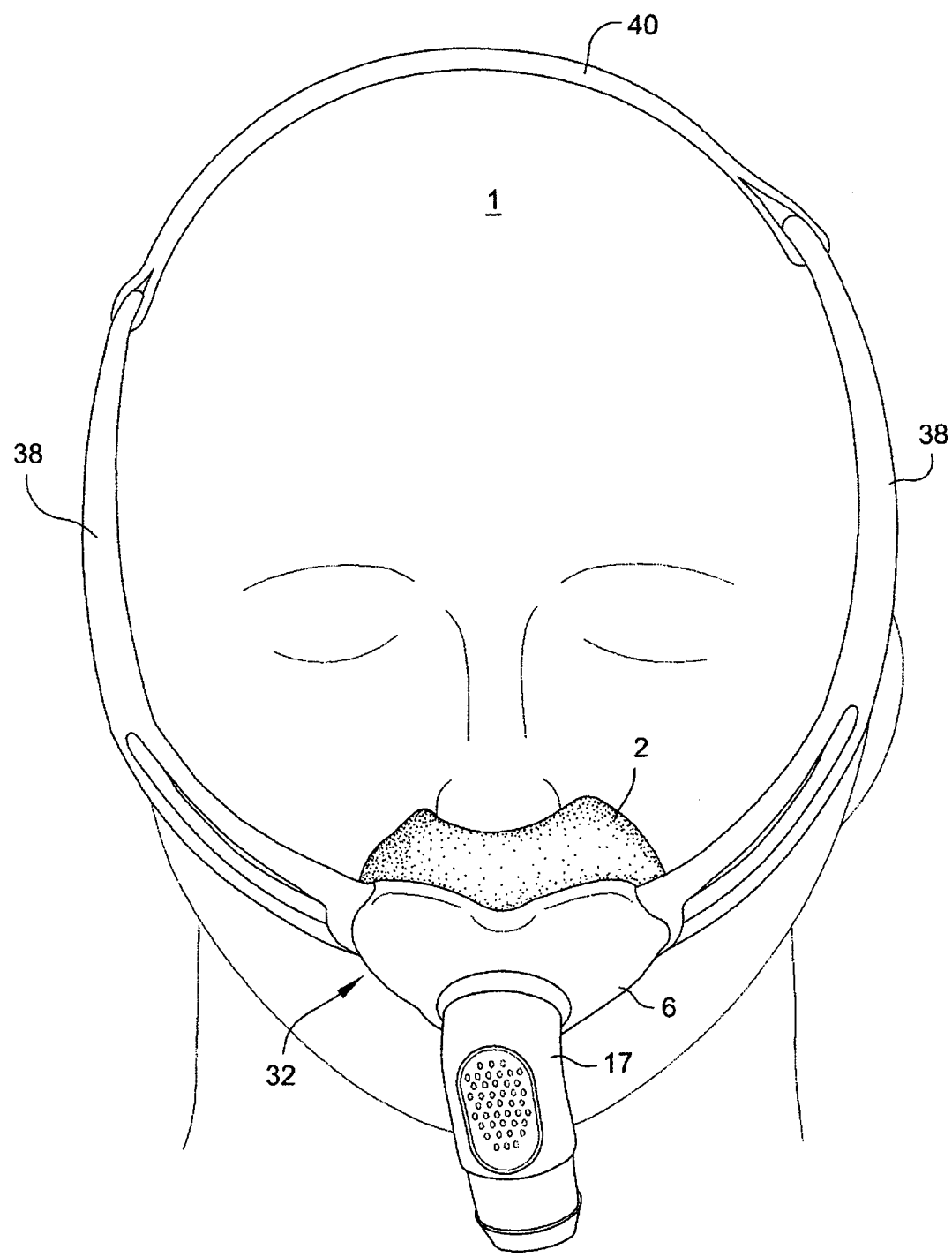
Figure 45D:
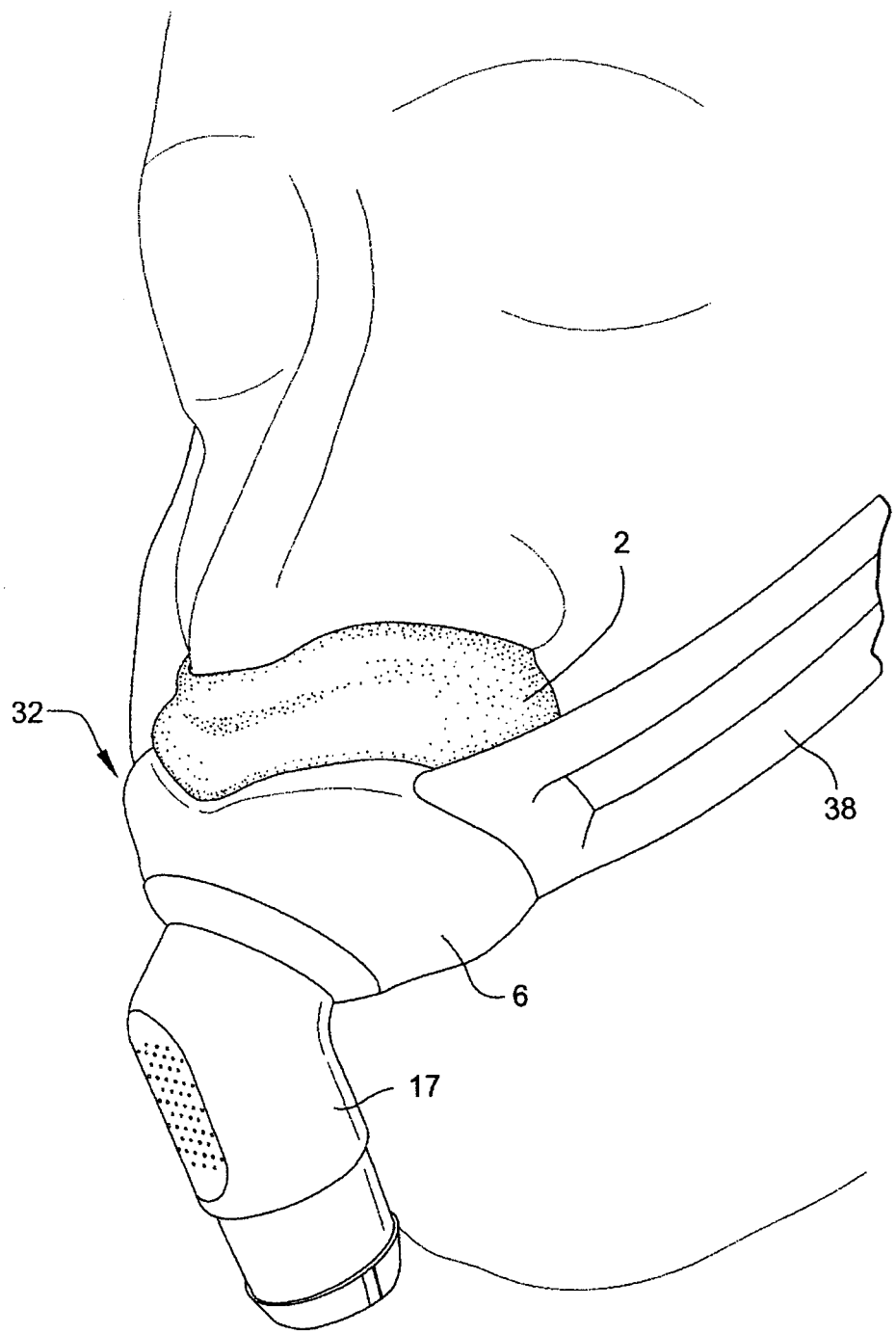
Figure 45E:
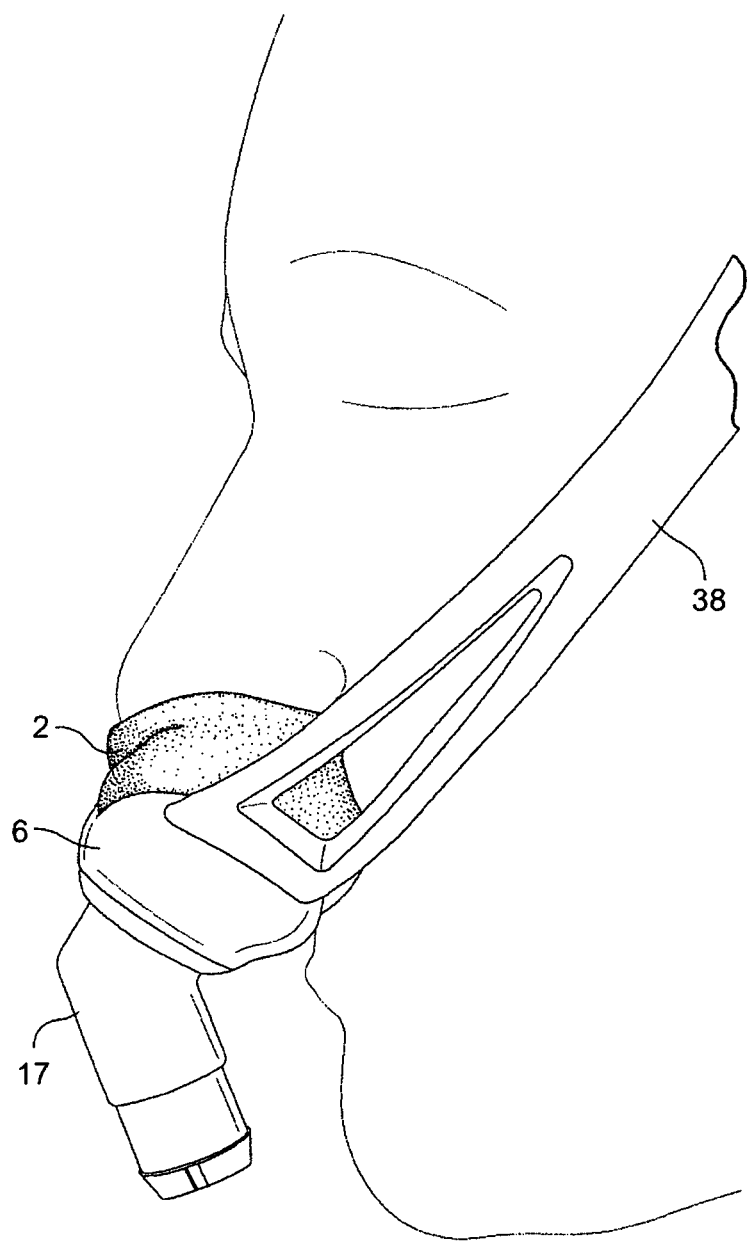

As shown in FIG. 45b, the seal 2 includes an aperture 19 that is configured to surround both nares of the patient. As shown in FIG. 45c, the flexible base 6 is conformable and in use wraps around the nose of the patient 1. As also shown in FIGS. 45c-45e, the seal 2 may be configured to seal in part above the tip of the patient's nose.

Seal Positioning and Stabilizing Structure

Seal Positioning and Stabilizing Structure—First Embodiment

Referring again to FIGS. 7a-7c, the seal positioning and stabilizing structure 36 may be formed, for example, from a flat silicone sheet. Typically, a headgear for a respiratory mask is formed from a foam and fabric laminate, such as BREATHOPRENE®. Such headgear is die cut and thus has squared edges. This can appear bulky on the face of the patient and can be uncomfortable due to its edges. In the sample embodiments disclosed herein, seal positioning and stabilizing structure made from silicone may be molded to have rounded edges. Such rounded edges improve comfort. In one form, the rounded edges may have a radius of greater than about 0.5 mm. As shown in FIG. 7b, the straps 38, 40, 42 of the seal positioning and stabilizing structure 36 may have the rounded edges 420 formed on the patient contacting (i.e. skin contacting) side 418 of the straps 38, 40, 42. The parting line 416 of the tool that forms the straps 38, 40, 42 may be further from the patient contacting side 418 to avoid flash near the patient's face that can cause irritation. As shown in FIG. 7c, the straps 38, 40, 42 may include a larger radius 422 on the patient contacting side 418 by providing portions 424 on the opposite side that are rolled back from the parting line 416.

Other polymers, e.g. TPE, may be used to form the seal positioning and stabilizing structure 36. The seal positioning and stabilizing structure 36 may include two side straps 38 (only one visible in FIG. 7a), a top strap 40, and a rear strap 42. Respective ends 38a of the side straps 38 are connected to connectors 12 (only one visible in FIG. 7a) provided on the flexible base 6 of the patient interface structure 32. The connectors 12 are located on sides of the flexible base 6 to which nasal pillows may be connected. The connection of the connectors 12 to the flexible base 6 enables the flexible base 6 to wrap around the base of the nose of the patient and be pulled back to retain the nasal pillows in a sealing relationship with the underside of the patient's nose.

Figure 7A:
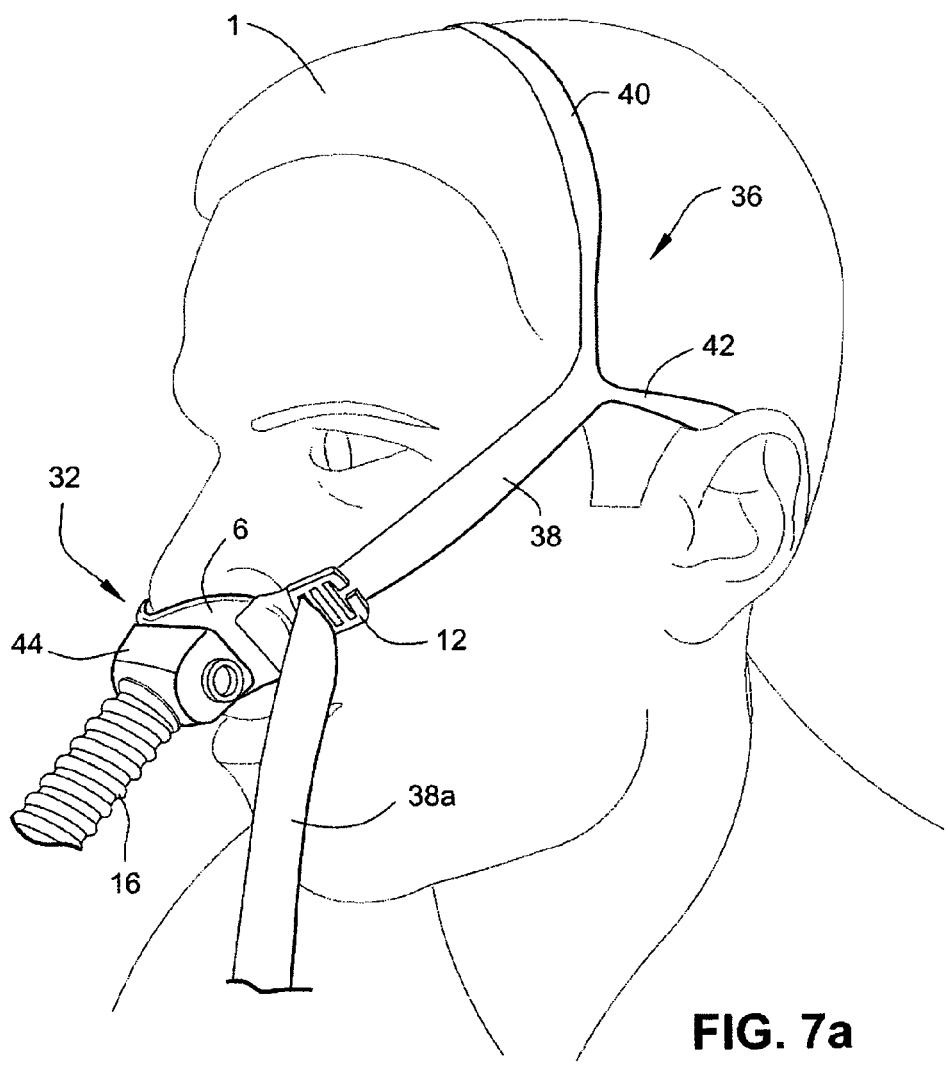
FIG. 7a schematically illustrates a patient interface system according to other sample embodiments.
Figure 7B:
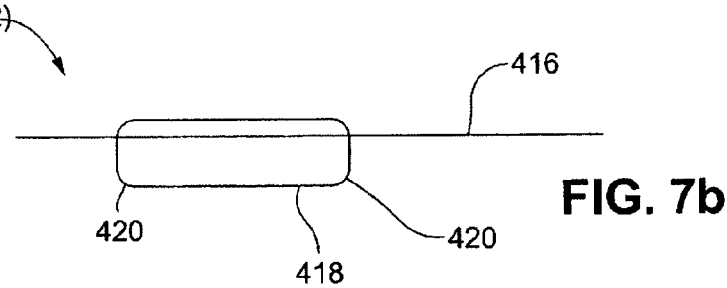
FIGS. 7b and 7c schematically illustrate straps according to sample embodiments.
Figure 7C:
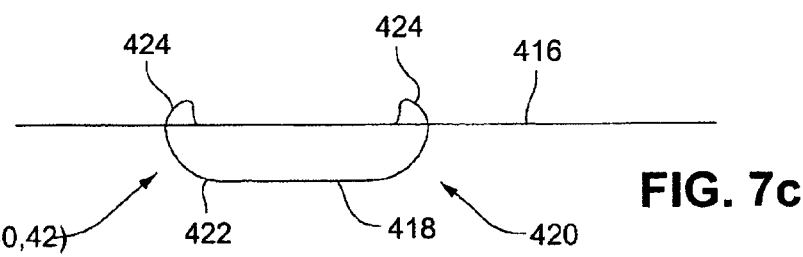

The respiratory mask system of FIG. 7a may be adjusted by adjusting the connection of the ends 38a of the side straps 38 with the connectors 12. For example, the connectors 12 may each include a slot, or slots, configured to accept the end 38a of the side strap 38. The sealing force provided by the seal positioning and stabilizing structure 36 may be adjusted by adjusting the ends 38a of the side straps 38. For example, to increase the sealing force applied by the seal positioning and stabilizing structure 36, the patient 1 may pull on the end(s) 38a of the side strap(s) 38. The sealing force may be decreased by shortening the end(s) 38a of the side strap(s) 38, e.g. by pulling the side strap(s) 38 back through the connector(s) 12. The patient interface structure 32 may be rotated with respect to the seal positioning and stabilizing structure 36 about an axis generally parallel to a line drawn through both eyes of the patient and below the patient's nose by the inherent flexibility of the straps. It should also be appreciated that inelastic straps may be used. It should be further appreciated that angular adjustment of the patient interface structure 32 with respect to the seal positioning and stabilizing structure 36 may be achieved by an adjustment buckle(s)/connector(s), such as those disclosed, for example, in U.S. Pat. No. 6,907,882, the entire contents of which are incorporated herein by reference.

Seal Positioning and Stabilizing Structure—Second Embodiment

Figure 10:
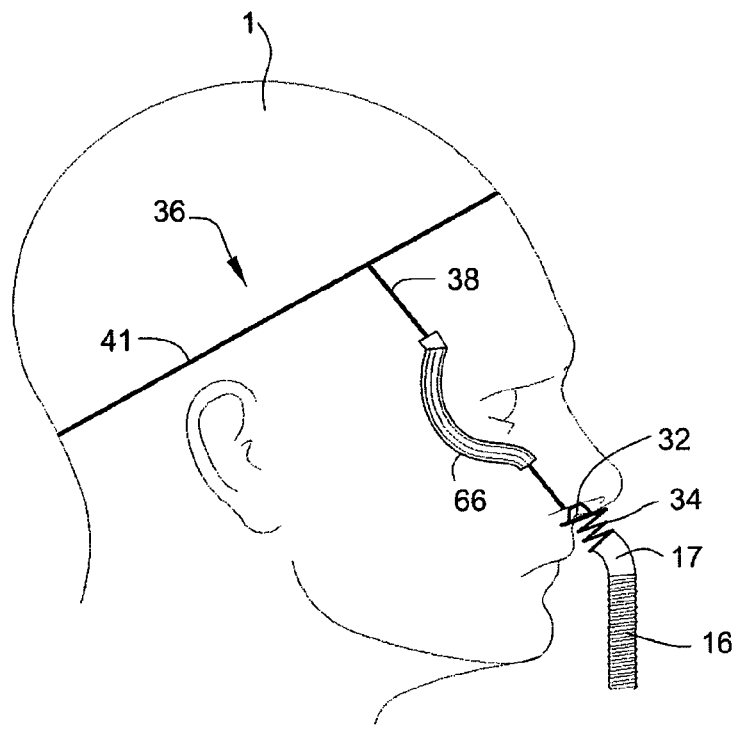
FIG. 10 schematically depicts a patient interface system according to a sample embodiment.

Referring to FIG. 10, in another sample embodiment, the seal positioning and stabilizing structure 36 may comprise a strap 41 configured to encircle the patient's head at a position above the patient's ears. A side seal positioning and stabilizing structure strap 38 (only one visible in FIG. 10) extends along each side of the face of the patient 1 and is connected to a respective side of the patient interface structure 32. The patient interface structure may be connected to a swivel elbow or joint 17 through a decoupling arrangement 34, although it should be appreciated that the patient interface structure may be connected to a rigid, or semi-rigid, frame or shell. The swivel elbow is connected to an air delivery tube 16 for the delivery of the flow of pressurized breathable gas.

A stiffening, or reinforcing, element 66 may be connected to each side strap 38. As shown in FIG. 10, in order to avoid impingement on the vision of the patient 1, the stiffening or reinforcing element 66 traverses the eye socket of the patient 1. The provision of the stiffening elements thus allows for the force vectors of the seal positioning and stabilizing structure to pass near the eyes of the patient without obscuring the patient's vision. Hence a tension force may be directed in a more ideal direction, orthogonal to the sealing surface, in this case the underside of the patient's nose.

The stiffening element 66 may be constructed from a material sufficiently stiff along the longitudinal length to resist bending under the seal positioning and stabilizing structure tension forces, but able to conform in an out of plane direction to lie flat on the patient's face. Suitable materials for the stiffening elements 66 include, for example, nylon, polypropylene, and silicone.

The stiffening elements 66 may be threaded through the side straps 38, or the stiffening elements 66 may be adhered or stitched in place on the side straps 38. Alternatively, the stiffening elements may be movable on the side straps 38 of the seal positioning and stabilizing structure 36, for example, by sliding along the side straps 38.

Seal Positioning and Stabilizing Structure—Third Embodiment

Figure 11:
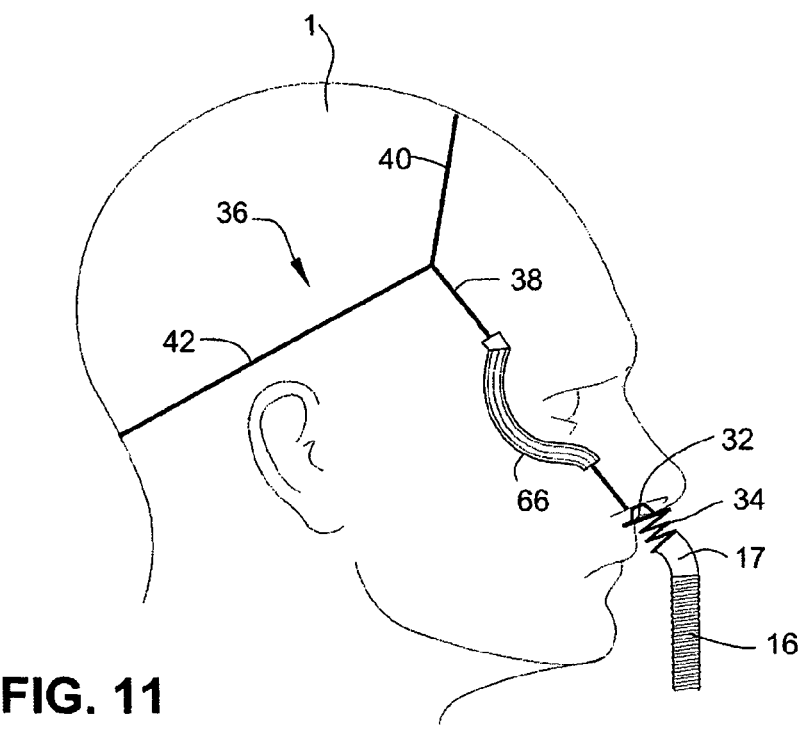
FIG. 11 schematically depicts a patient interface system according to a sample embodiment.

Referring to FIG. 11, in another sample embodiment, the top strap 40 may be configured to extend at an angle to the rear strap 42. This configuration produces force vectors that increase the sealing force applied by the seal positioning and stabilizing structure 36 without increasing the tension. A component of the force provided by the top strap 40 is directed upward, which increases the sealing forces applied to the patient interface structure 32. In other words, the sealing force component of the top strap 40 is added to the sealing force component of the side straps 38 to provide improved sealing without increasing tension.

Seal Positioning and Stabilizing Structure—Fourth Embodiment

Figure 12A:
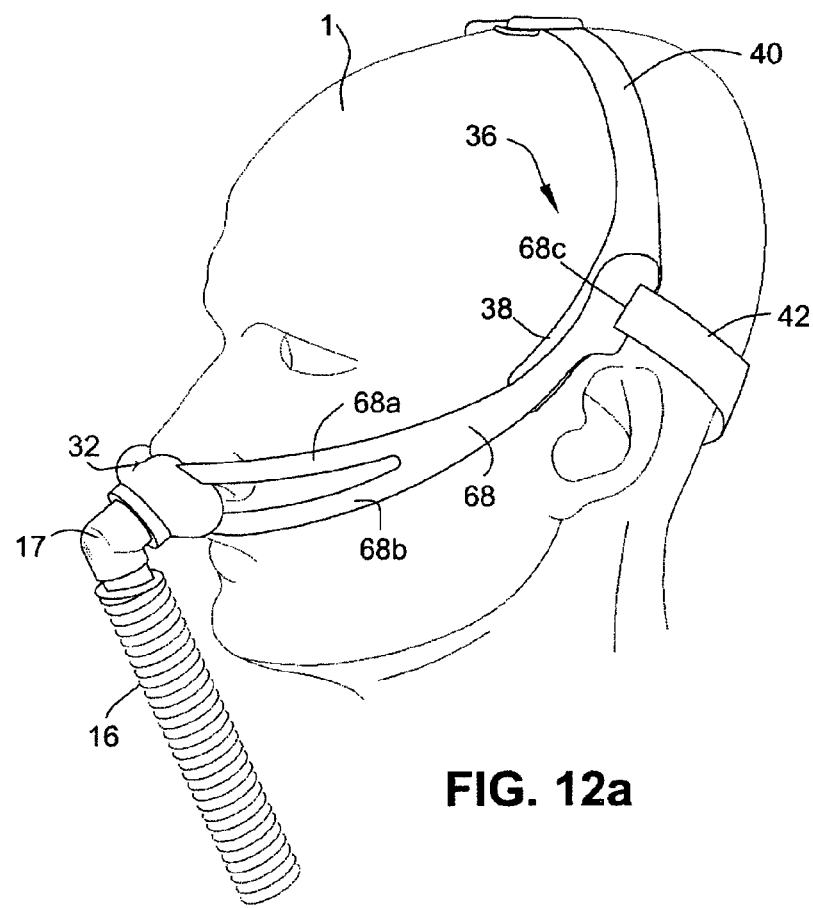
FIGS. 12a and 12b schematically illustrate a side view and a rear view, respectively, of a patient interface system according to another sample embodiment.
Figure 12B:
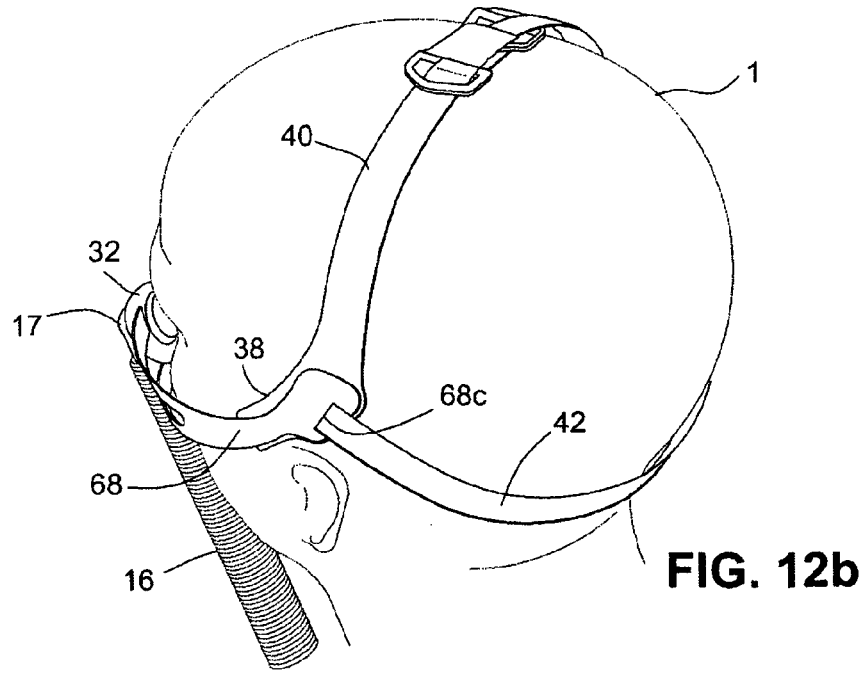

Referring to FIGS. 12*a* and 12*b*, a patient interface system according to another sample embodiment comprises a seal positioning and stabilizing structure 36 connected to a patient interface structure 32 by lateral side arms 68 provided on each side of the face of the patient 1. Each lateral side arm 68 may comprise a first side arm connector 68*a* connected to the patient interface structure and a second side arm connector 68*b*, with respect to the orientation shown in FIG. 12*a*, below the first side arm connector 68*a*, connected to the patient interface structure 32. The lateral side arm 68 may be connected to the rear strap 42 of the seal positioning and stabilizing structure 36 through a slot 68*c* provided in the lateral side arm 68 that receives the rear strap 42. As shown in FIGS. 12*a* and 12*b*, a side strap 38 of the seal positioning and stabilizing structure 36 may extend along a portion of the lateral side arm 68. It should be appreciated, however, that the side strap 38 may be eliminated and the lateral side arm 68 may extend from the junction of the top strap 40 and the rear strap 42. Each lateral side arm 68 may be configured to lie on the face of the patient from a point in the general region of the temple to near the base of the patient's nose.

The lateral side arms 68 may be formed of material similar to the stiffening elements described above with reference to FIGS. 10 and 11. Alternatively, the lateral side arms 68 may be formed from a soft flexible material, for example a laminate of compressed foam and fabric material, such as BREATHOPRENE®. The lateral side arms 68 may be constructed to be sufficiently stiff along the longitudinal length to avoid bending under the seal positioning and stabilizing structure tension forces, but able to conform in an out of plane direction to lie flat on the patient's face.

The first and second side arm connectors 68*a*, 68*b* are connected to the patient interface structure 32 at two points and are sufficiently wide at the connections to improve control over the rotational stability of the seal, but permit rotation of the patient interface 32 to present the seal, e.g. nasal pillows, at a right angle to the sealing surface.

Seal Positioning and Stabilizing Structure—Fifth Embodiment

Figure 13A:
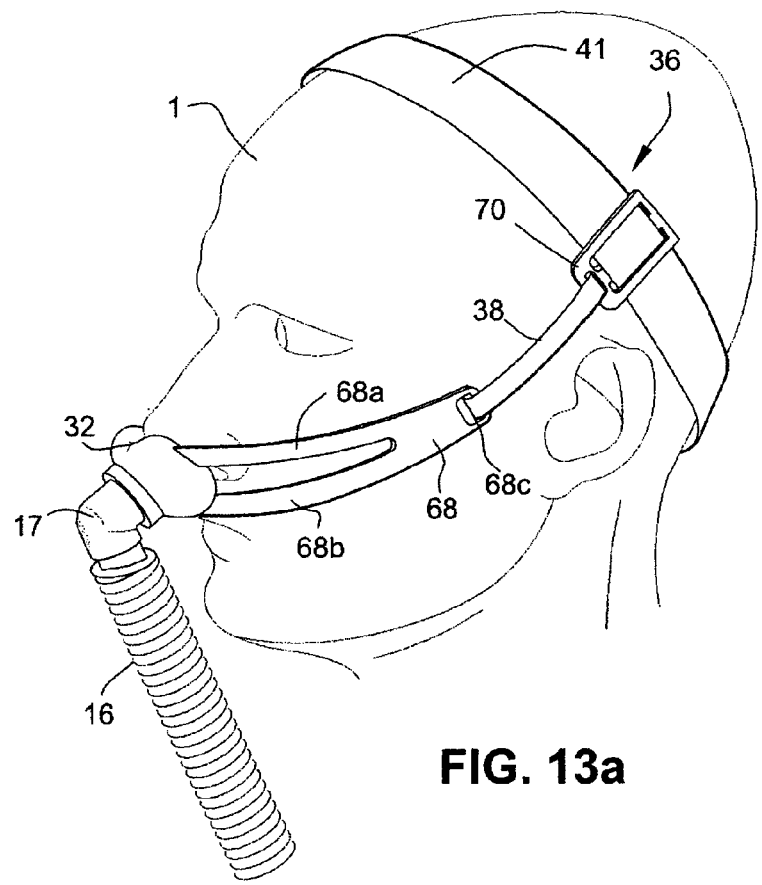
FIGS. 13a and 13b schematically illustrate a side view and a rear view, respectively, of a patient interface system according to another sample embodiment.
Figure 13B:
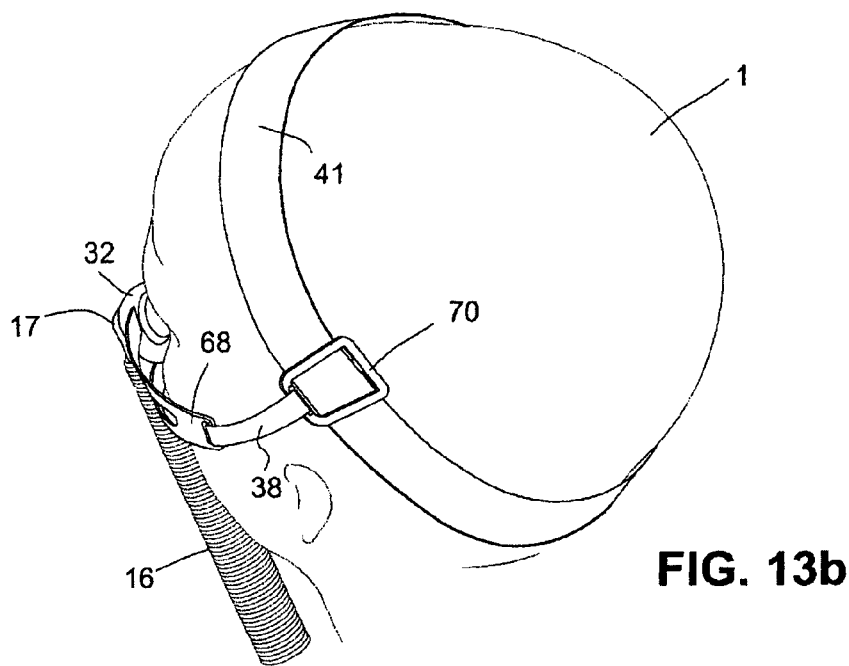

Referring to FIGS. 13*a* and 13*b*, the lateral side arms 68 may be connected to the side straps 38 through slots 68*c*. The side straps 38 may be connected to the strap 41 by a strap connector 70. The side strap 38 is connected at one end to the strap connector 70 and at the opposite end to the lateral side arm 68 through the slot 68*c*. The strap connector 70 may be moved along the strap 41 to allow the patient to adjust the position of the lateral side arms 68. The patient may thus adjust the position of the lateral side arm 68 to effect a good seal between the patient interface structure 32 and the nares of the patient, and the patient interface system may be adjustable to fit patients of a variety of sizes.

Seal Positioning and Stabilizing Structure—Sixth Embodiment

Figure 14A:
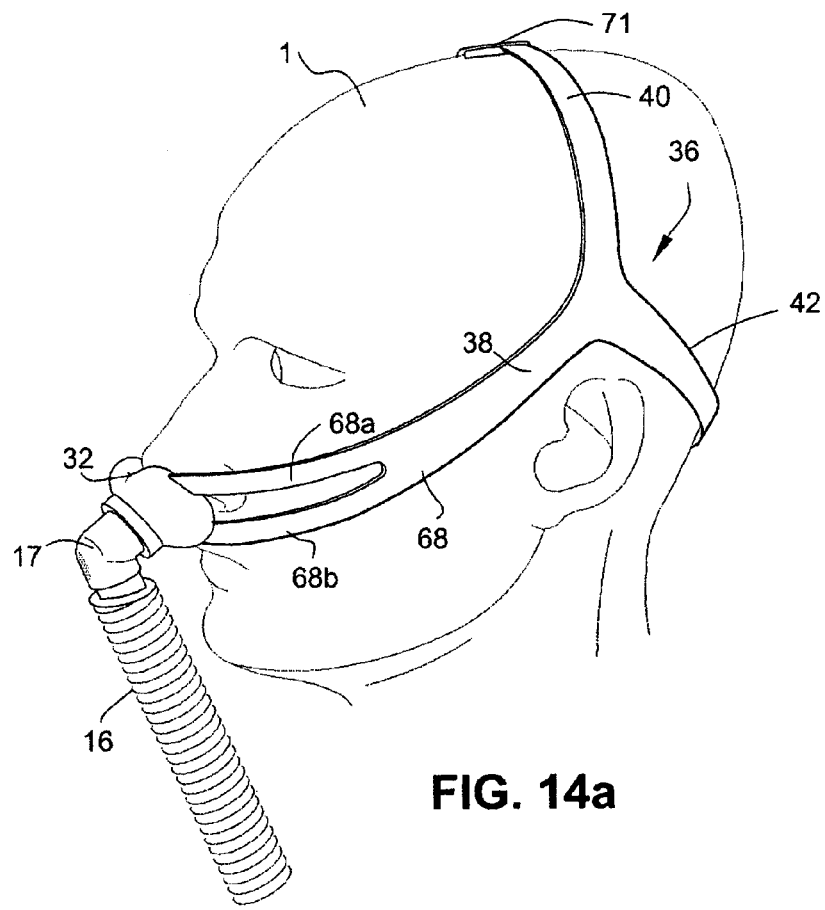
FIGS. 14a and 14b schematically illustrate a side view and rear view, respectively, of a patient interface system according to another sample embodiment.
Figure 14B:
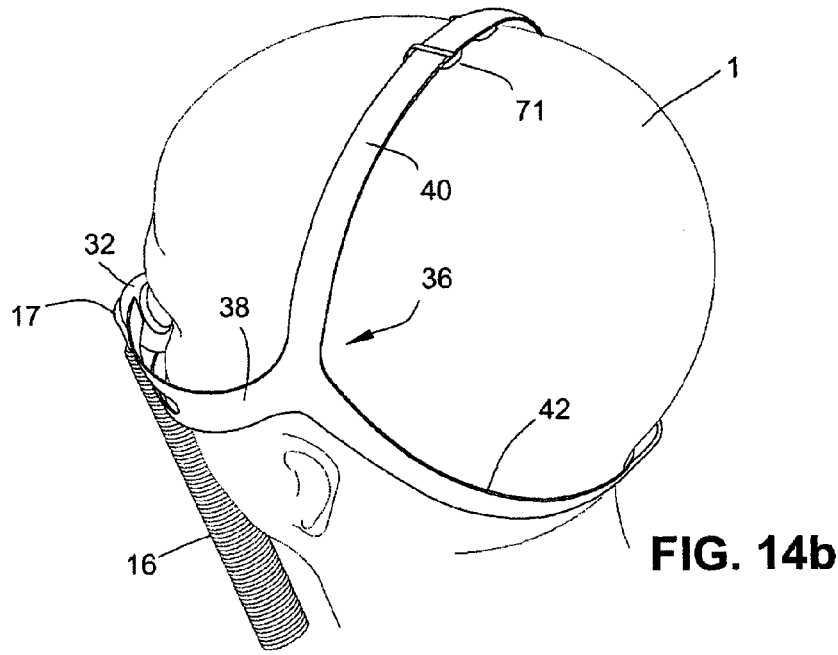

Referring to FIGS. 14*a* and 14*b*, according to another sample embodiment, the seal positioning and stabilizing structure 36 may be formed of a single piece, including the top strap 40, the rear strap 42, the side strap 38 and the lateral side arms 68. A buckle 71 may be provided on the top strap 40 to adjust the fit of the seal positioning and stabilizing structure 36 to the patient. It should be appreciated that the buckle may be provided additionally or alternatively to the rear strap 42. The single piece seal positioning and stabilizing structure 36 may be connected to the patient interface structure 32 by connectors such as hook and loop fasteners. Alternatively, the single piece seal positioning and stabilizing structure 36 may be a complete circular component that can wrap around the patient interface structure 32 at, for example, the base of the patient interface structure 32 between the patient interface structure 32 and the elbow 17, or at the top of the patient interface structure 32 between the flexible base of the patient interface structure 32 and the seal (e.g. nozzle arrangement). In another sample embodiment, the entire patient interface system, including the patient interface structure 32 and the seal positioning and stabilizing structure 36 may be formed as a single component. Additionally, the elbow 17 may also be formed with the patient interface structure 32 and the seal positioning and stabilizing structure 36.

As shown in FIGS. 14a and 14b, and FIGS. 12a-13b, the lateral side portions 68 may divide into first and second side arm connectors 68a, 68b to form a triangular cut out proximal to the patient interface structure 32, as shown in the figures. The lengths of the first and second side arm connectors 68a, 68b affect the angle at which the patient interface structure 32 is positioned. For example, if the first side arm connector 68a is longer than the second side arm connector 68b, the patient interface structure 32 is likely to rotate away from the patient's nares. Conversely, if the second side arm connector 68b is longer than the first side arm connector 68a, the patient interface structure 32 is likely to rotate towards the patient's nares. In another sample embodiment, the length of the first side arm connector 68a may be adjustable, thereby rotating the patient interface structure 32, by an adjustment mechanism, such as a buckle. Similarly, adjustment may be provided to the second side arm connector 68b to alter its length and thus rotate the patient interface structure, for example by an adjustment mechanism such as a buckle. Adjustment may also be provided to both the first side arm connector 68a and the second side arm connector 68b to allow greater adjustment of the patient interface structure 32.

Seal Positioning and Stabilizing Structure—Seventh Embodiment

Figure 15A:
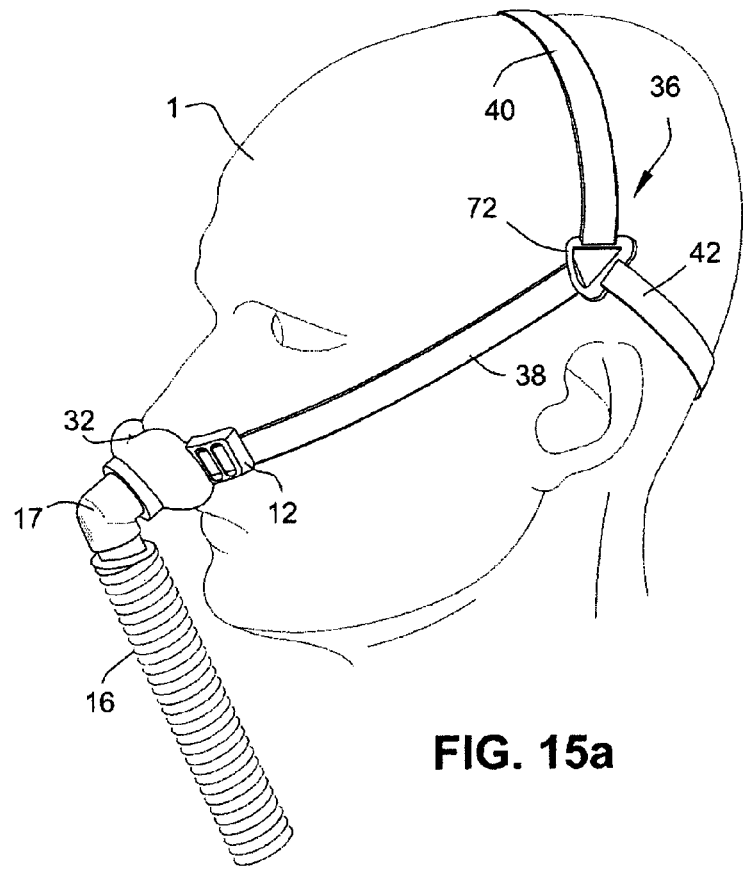
FIGS. 15a and 15b schematically illustrate a side view and rear view, respectively, of a patient interface system according to another sample embodiment.
Figure 15B:
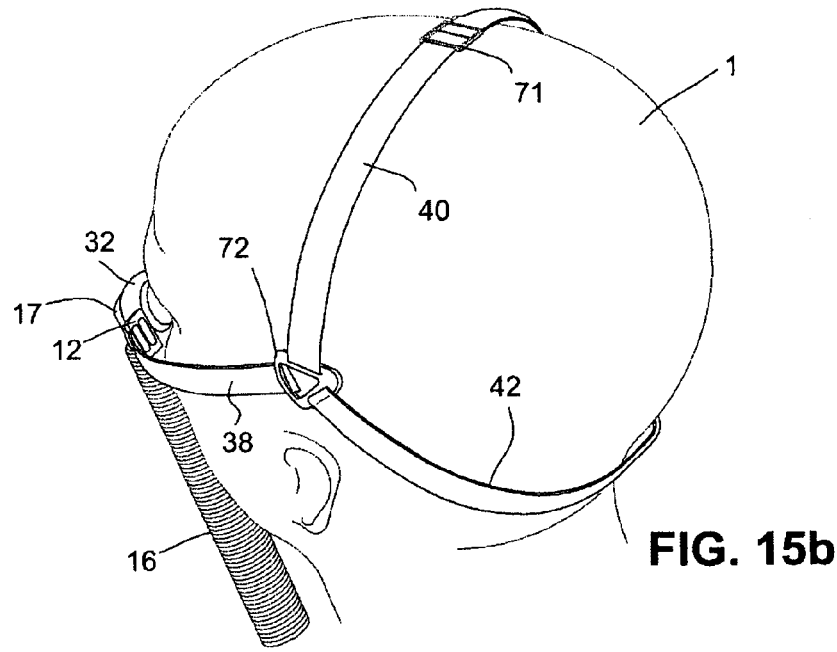

Referring to FIGS. 15a and 15b, according to another sample embodiment, the side strap 38, the top strap 40, and the rear strap 42 of the seal positioning and stabilizing structure 36 are connected by a connector 72. The side strap 38 may be connected to the patient interface structure 32 by a seal positioning and stabilizing structure connector 12 which is provided on the patient interface structure 32. The patient interface structure 32 may be connected directly to an air delivery tube 16 by a swivel elbow 17. The connector 72 allows the position of each of the straps 38, 40, 42 to be adjusted to allow the patient to effect a seal between the patient interface structure 32 and the airways of the patient and allows the seal positioning and stabilizing structure 36 to be sized and fitted to a variety of patients.

Seal Positioning and Stabilizing Structure—Eighth Embodiment

Figure 24A:
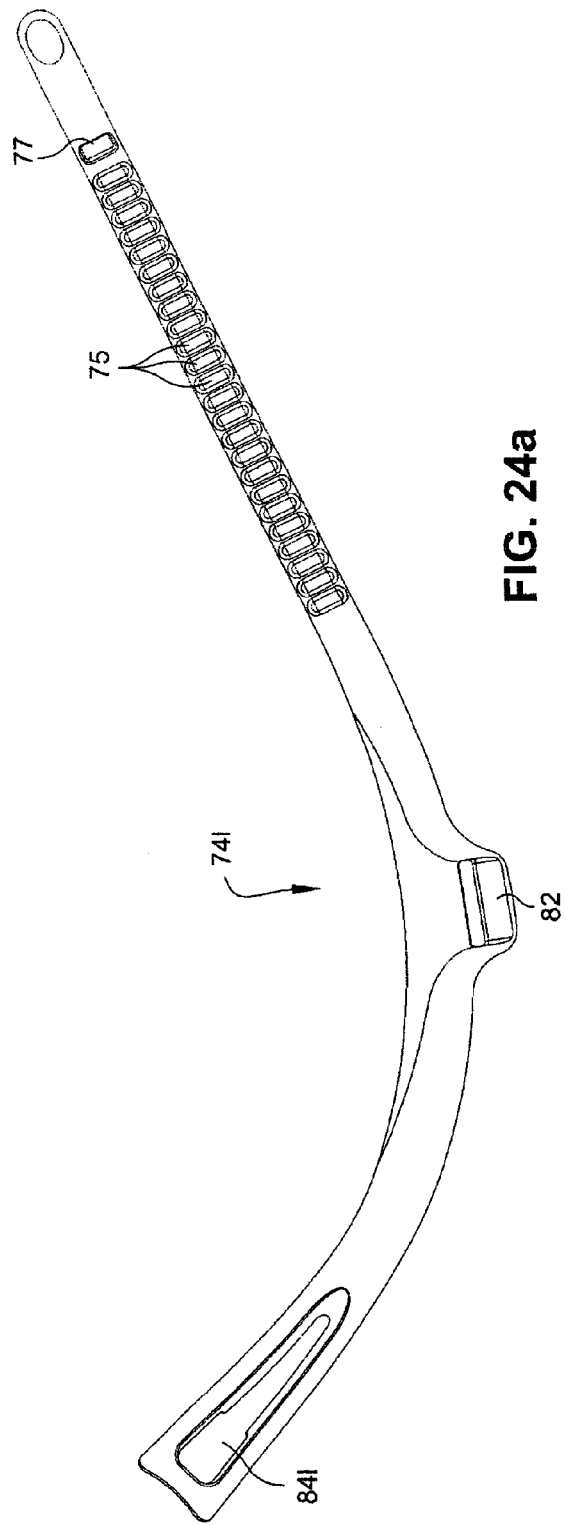
Figure 24B:
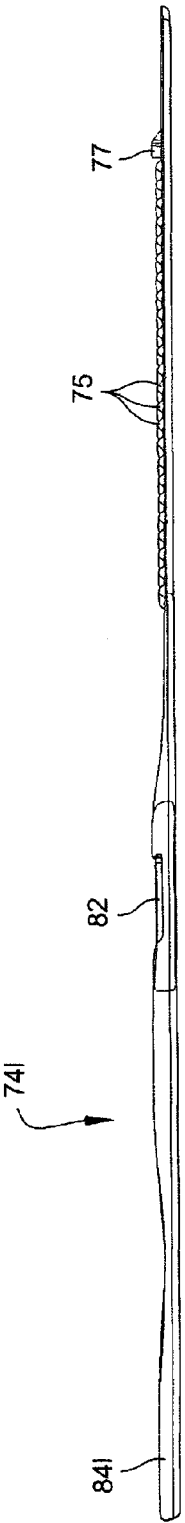
Figures 24C, 24D:
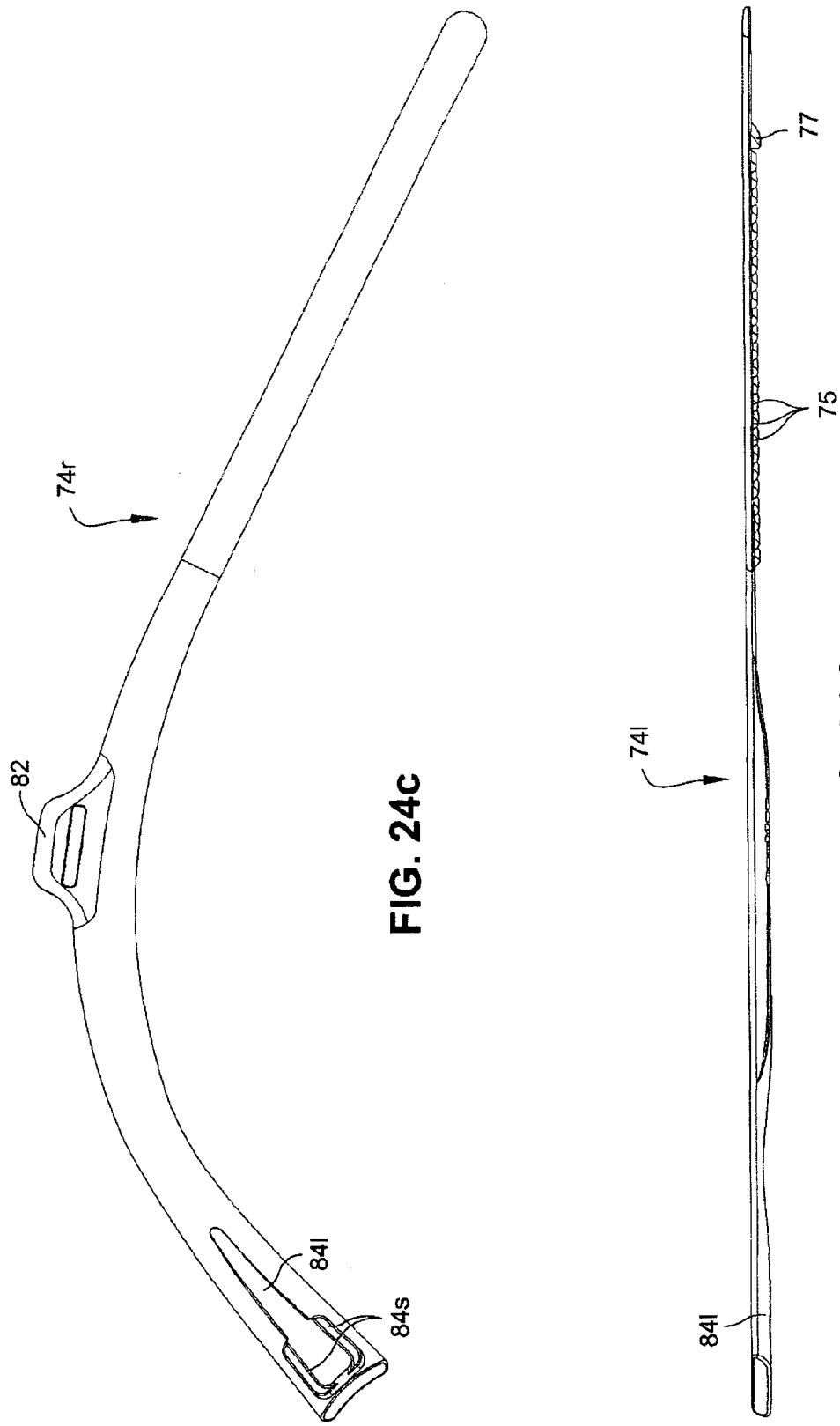
Figure 24G:
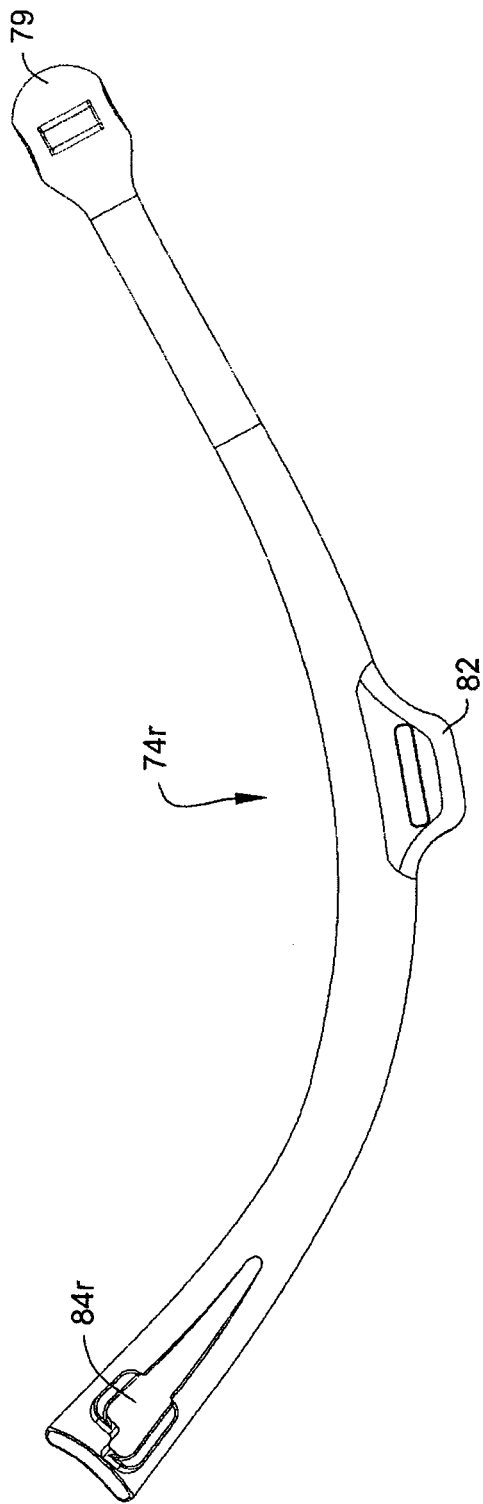
Figure 24H:
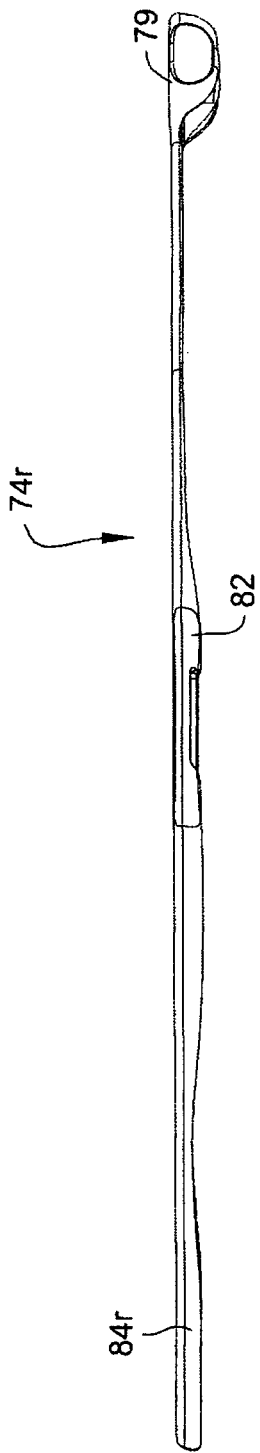
Figure 24I:
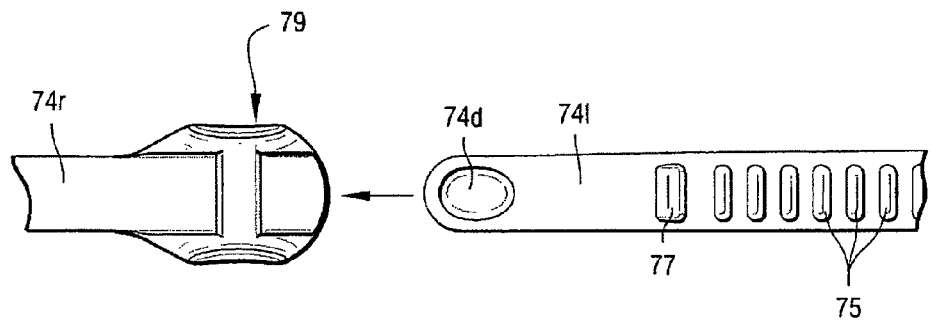
Figure 24J:
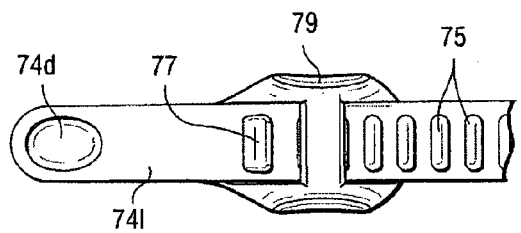
Figure 24K:
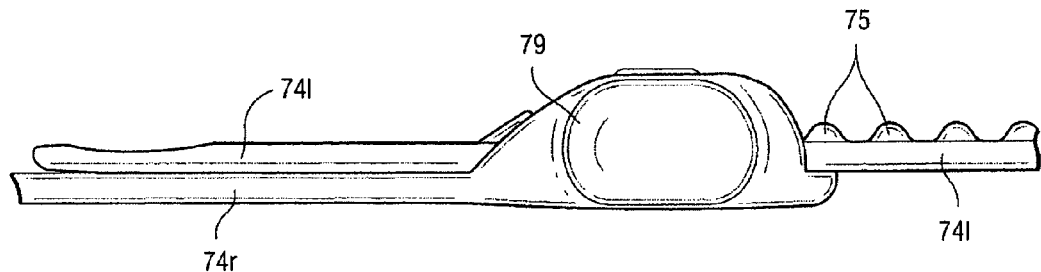
Figure 24L:
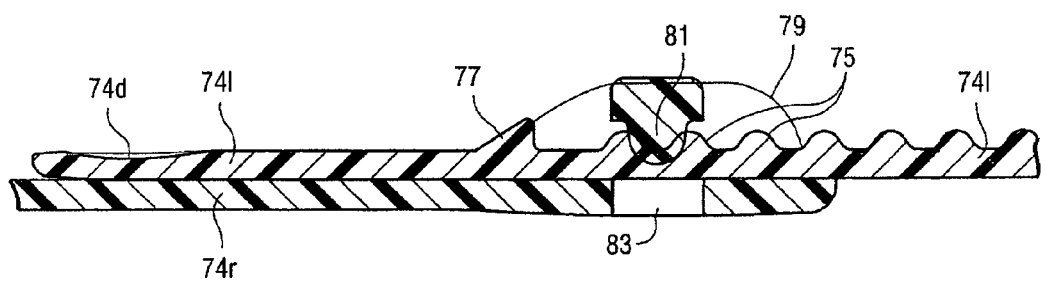
Figure 24M:
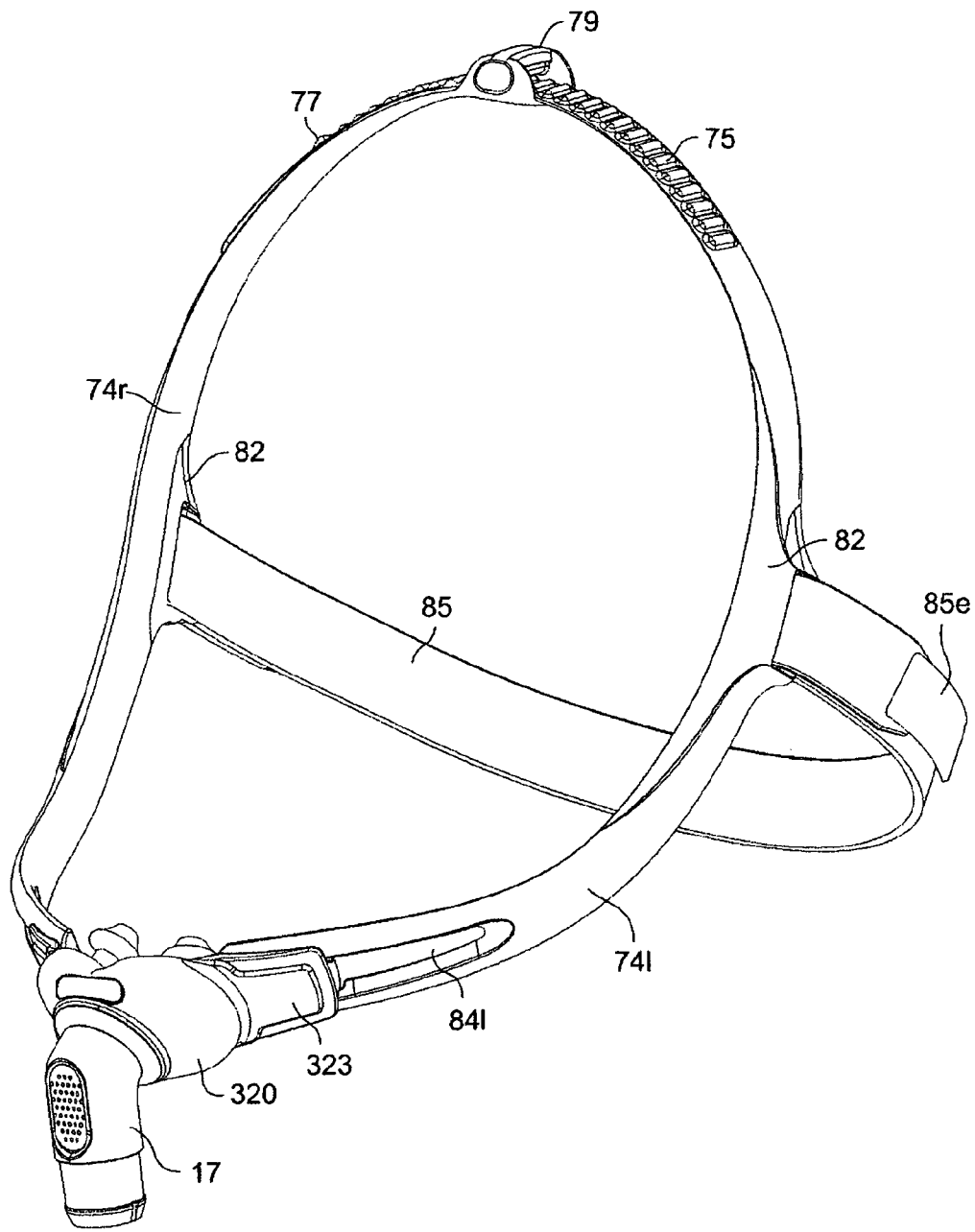
FIGS. 24m-24q schematically illustrate a patient interface system according to a sample embodiment including the seal positioning and stabilizing structure of FIGS. 24a-24l.
Figure 24N:
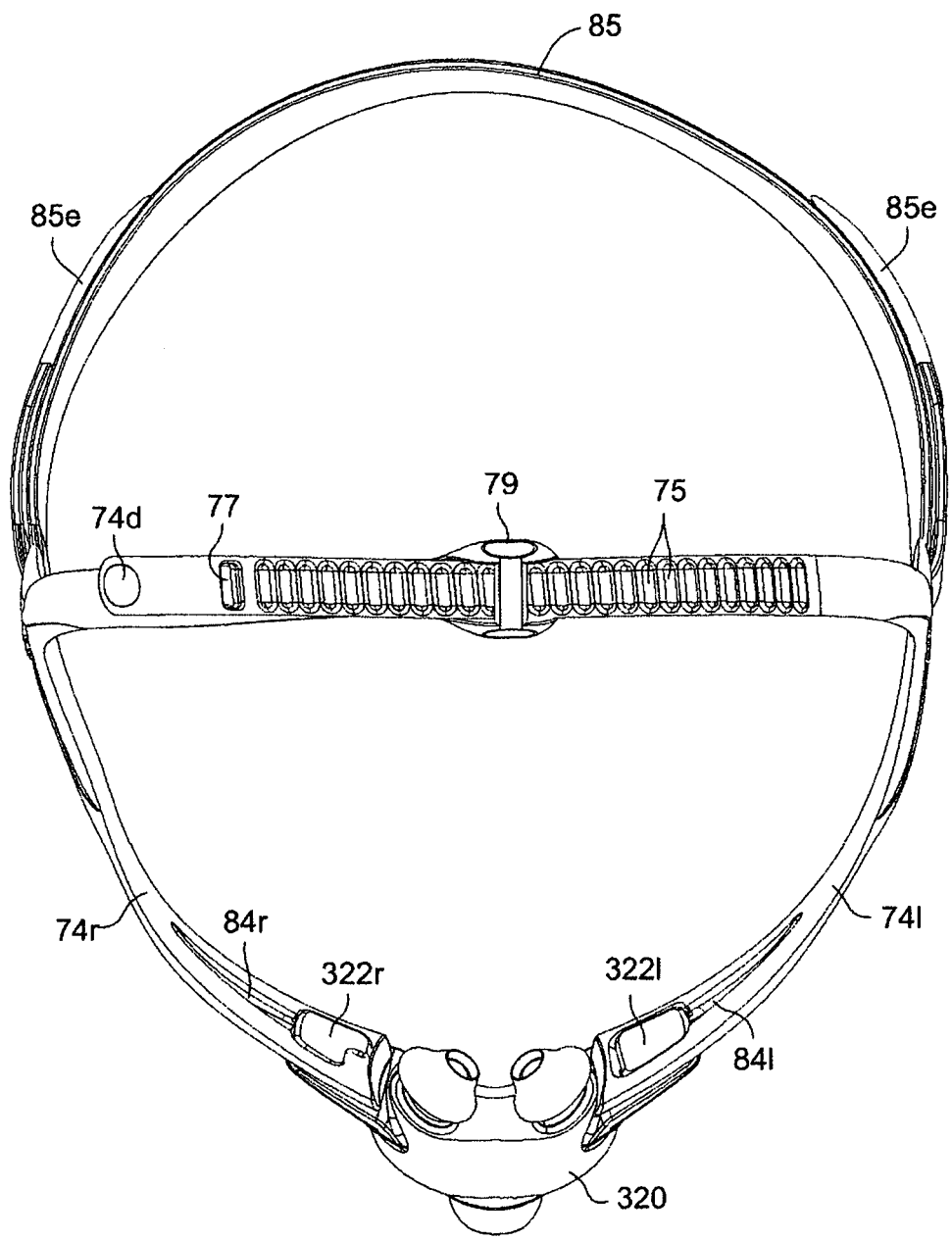
Figure 24O:
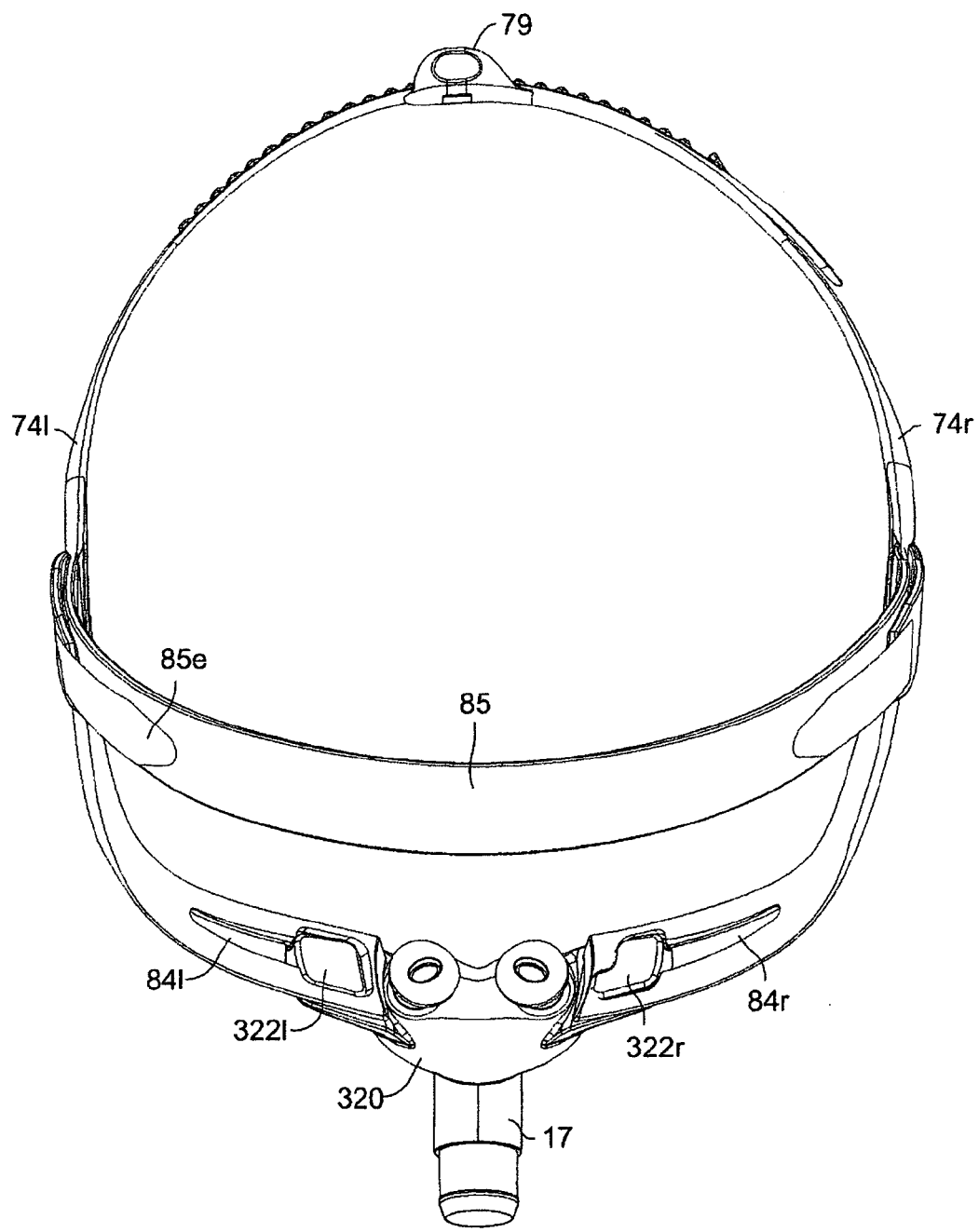
Figure 24P:
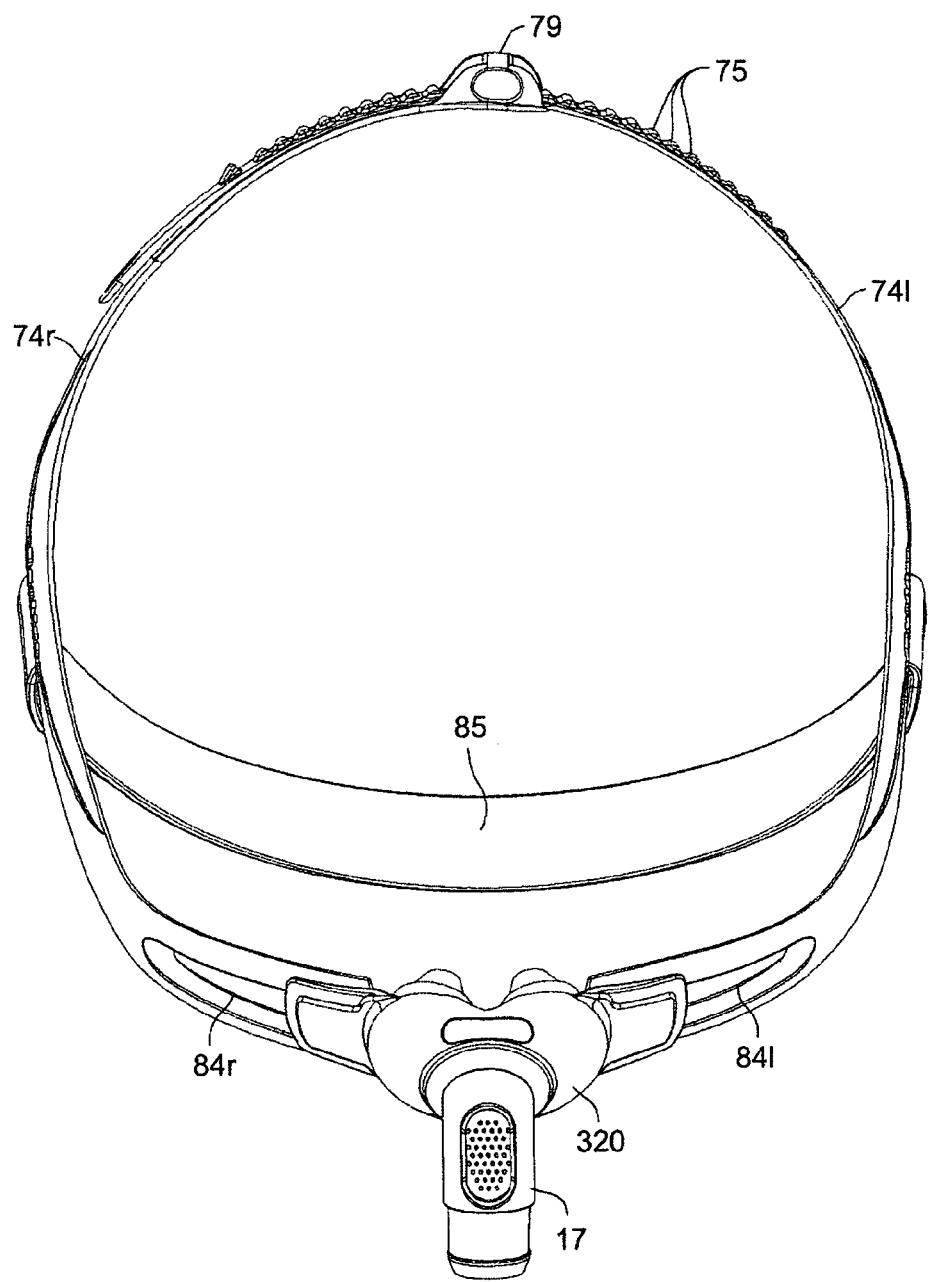
Figure 24Q:
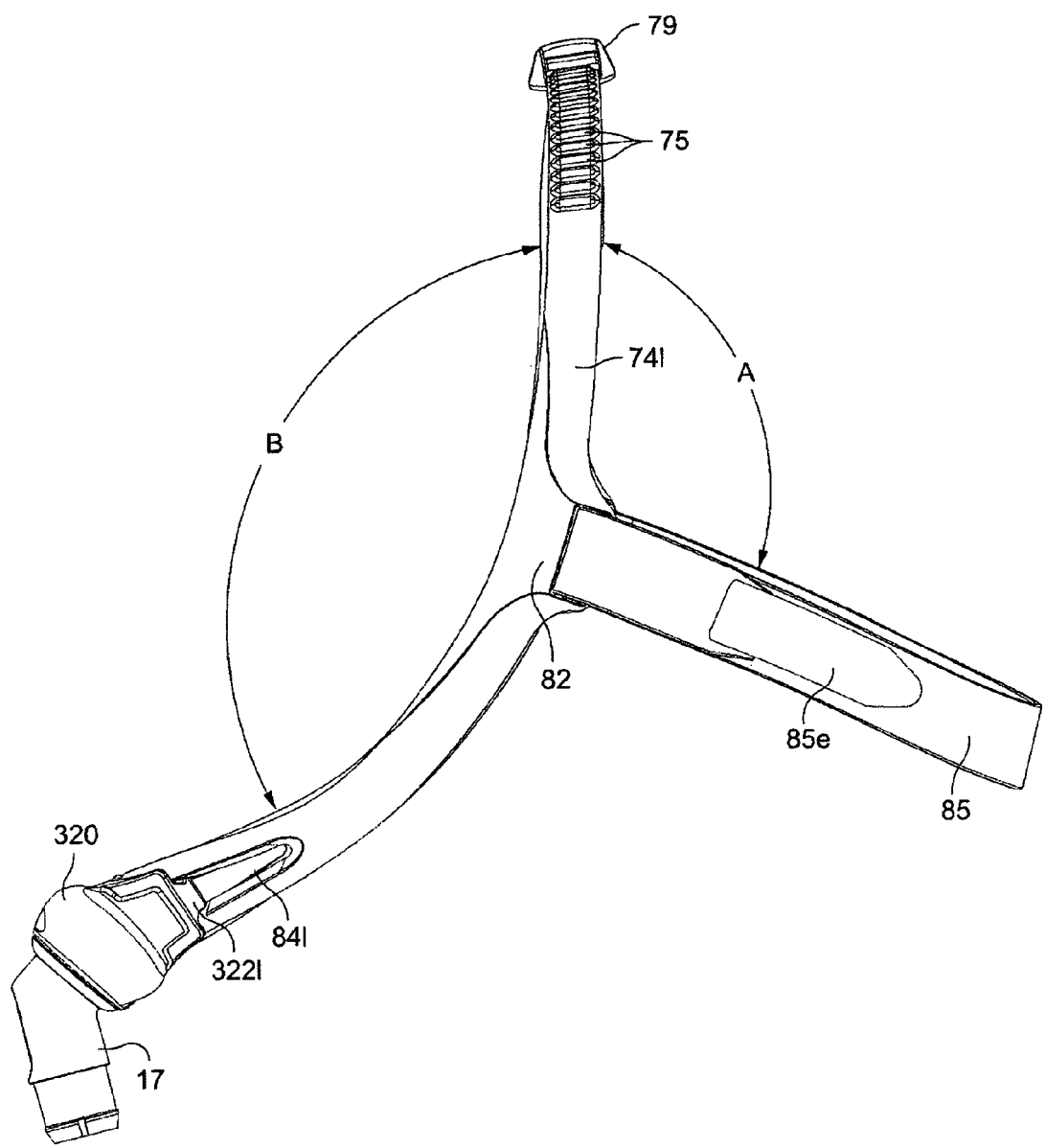

FIGS. 24m-24q show a patient interface assembly including an eighth embodiment of a seal positioning and stabilizing structure. The seal positioning and stabilizing structure includes a main strap loop 74, and rear strap 85. With reference to FIG. 24q main strap loop 74 includes a strap connector 82 arranged to connect rear strap 85 at an angle A with respect to the crown engaging top portion main loop 74 of about 90° to about 140°, preferably about 95° to about 110°, most preferably about 100°. The closer the angle A is to the preferred values there is a progressive improvement in the fit range of the headgear, allowing the patient interface to comfortably fit a range from smaller to larger heads.

With further reference to FIGS. 24q, 16a and 16d, the main strap loop 74 has a curved middle portion in between two generally straight portions. The first straight portion lies over the crown of the patient's head in use. The second straight portion has one end connected with a lateral portion of the patient interface structure, and is generally parallel therewith. The curved middle portion corresponds to the stiffened region 78 discussed below. The angle B between the two straight portions is preferably in the range of about 150° to about 90°, for example about 130° to about 90°, more preferably about 120° to about 100°, most preferably about 111°. The closer the angle B is to the preferred values there is a progressive improvement in the fit range of the headgear, allowing the patient interface to comfortably fit a range from smaller to larger heads. Furthermore, the stiffened, curved portions allows headgear tension forces to be applied to the underside of the patient's nose at a more effective angle, preferably orthogonal to the underside of the nose, without the headgear obscuring the patient's vision, or contacting sensitive eye regions. In the preferred arrangement there is no sharp change in direction, compared to for example, the ResMed Swift® LT. Furthermore this headgear (i.e. seal positioning and stabilizing structure) arrangement avoids impinging on patient's ears in a wider range of head sizes.

Referring to FIGS. 46a and 46b, an angle Y between a line generally perpendicular to the strap connector 82 and a line extending through the first end of the strap loop 74 may be in a range of from 90° to about 140°, preferably about 95° to about 125°, most preferably about 100°.

Figure 16G:
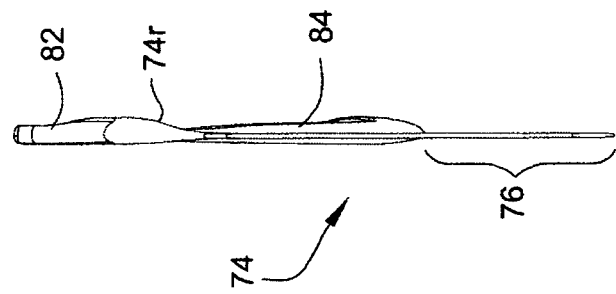
Figure 16F:
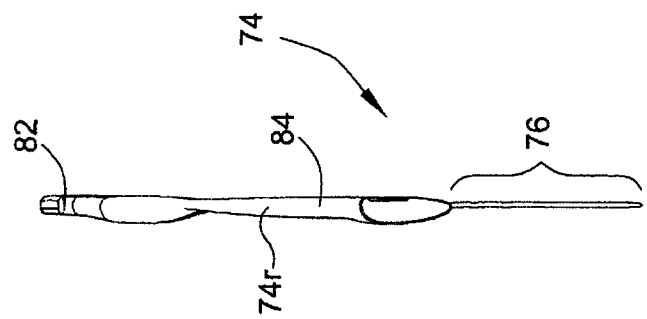

Referring to FIGS. 16a-16g, as discussed previously with respect to FIGS. 44a and 44b, the seal positioning and stabilizing structure may include a main strap loop 74 including right and left main straps 74r, 74l, shown in FIG. 16d and FIG. 16a, respectively. Each main strap 74r, 74l may include a first flexible region 76, a stiffened region 78, and a second flexible region 80. As shown in FIGS. 16a-16g, the thicknesses of the regions 76, 78, 80 along the main strap 74r, 74l may be varied to enable the main strap 74r, 74l to be sufficiently stiff in areas under load and flexible in areas where conformance to the face is required. The first flexible region 76 is thinner than the stiffened region 78 and may have a thickness of about 0.5 mm-1.5 mm, for example about 1 mm. The second flexible region 80 is also thinner than the stiffened region 78 and may have a thickness of about 1 mm-3 mm, for example 2 mm. As shown in FIGS. 16b, 16c, and 16e, the second flexible region 80 may have a varying thickness and the second flexible region may have increased flexibility at its thinnest portion. The stiffened region 78 is thicker than the first and second flexible regions 76, 80 and may have a thickness of about 3 mm-10 mm, for example about 6 mm.

Preferably the main strap loop 74 is molded from a silicone having a Shore A hardness in the range of about 40 to about 80, more preferably in the range of about 60 to about 70, most preferably about 65. Making the main strap loop 74 from a harder silicone makes it stiffer, and may allow it to be thinner than were it to be made from a softer silicone. Preferably the main loop 74 is not an air delivery tube, or not attached to an air delivery tube, although it may be either. Using the main loop as an air delivery tube, or coupled to one may reduce the benefits provided by the decoupling arrangements. While the main loop 74 made from the preferred silicone and thickness is more flexible than a foam and fabric structure reinforced with nylon stiffeners, it has sufficient structure that it retains a degree of shape when standing by itself, facilitating use by patients who might otherwise be confused by an overly floppy headgear structure that gives few clues as to how it should be used. Furthermore, making the main loop 74 from silicone in the preferred hardness range, and in the preferred thickness ranges means that improved stability of the seal may be provided, avoidance of sensitive regions of the face, and improved fit range without requiring the use of harder or stiffer materials (e.g. nylon stabilizers) that may cut into the patient's skin, or leave marks on their face. The curved shape of the stiffened region reduces or eliminates the need for harder, stiffer stabilizers that may be required were the angle between the crown-engaging top portion and the front portion of the main loop 74 sharper. Furthermore, the use of silicone in the main loop provides a degree of flexure upon movement of the air delivery tube, decoupling it from affecting seal, unlike a more rigid, or inextensible stabilizer. Silicone may provide an improved "grip" to the patient's skin. Molding the main loop is a relatively simple, low waste manufacturing step and does not require additional assembly processes (such as stitching a stiffener to a foam and fabric laminate). Die cutting a shape that cannot be readily nested from a sheet may result in wasted material. In accordance with a preferred form of the present technology, the rear strap 85 is relatively straight, and hence can be die cut from a sheet of material with relatively little waste. Hence the preferred form of seal positioning and stabilising structure is more cost effective.

The main straps 74r, 74l may have a width of about 5 mm to about 15 mm, for example about 10 mm, in the region configured to engage the crown of the patient's head and may widen to a width of about 15 mm to about 25 mm, for example about 20 mm in the region configured to contact the patient's face in the region of the cheek, for example in the region around the strap connector 82. The width of the straps 74r, 74l may narrow between strap connector 82 and the connector 84, for example from about 20 mm to about 10 mm, and then increase toward the connector, for example to about 15 mm to about 25 mm, for example about 20 mm.

A strap connector 82 may be provided in the stiffened region 78. The strap connector is configured to receive, for example, a rear strap configured to extend around the back of the head of the patient to secure the seal positioning and stabilizing structure to the patient, and facilitating lengthwise adjustment of the rear strap in one or two points. The back strap may be formed of the same material as the main straps 74r, 74l, for example, silicone, or formed from foam and fabric, such as BREATHOPRENE®. It should be appreciated that the back strap may be formed of a different material than the main straps 74r, 74l, such as elastic, or from a combination of materials. It should also be appreciated that the durometer of the main straps 74r, 74l may be varied along its length instead of, or in addition, to varying the thickness of the main straps 74r, 74l.

Each main strap 74r, 74l includes a patient interface structure connector 84 that is configured to receive a corresponding connector formed on the patient interface structure, described below with respect to FIGS. 17a-17f. As shown in FIGS. 16a-16g, the patient interface structure connector 84 may be in the form of a triangular cut out formed in the end of the main strap 74r, 74l. It should be appreciated, however, that the patient interface structure connector 84 may comprise a cut out having a different shape than triangular.

Seal Positioning and Stabilizing Structure—Strap Connectors

Silicone is more flexible than standard headgear materials, such as BREATHOPRENE®, and may not perform as desired in standard headgear strap connectors. For example, silicone has a tendency to slide in the connector(s) and become loose. As discussed in more detail below, sample embodiments of seal positioning and stabilizing structure strap connectors are particularly suitable for use with silicone seal positioning and stabilizing structure straps, although the sample embodiments are not limited to silicone seal positioning and stabilizing structure straps.

Ladder Lock Strap Connector

Figure 19A:
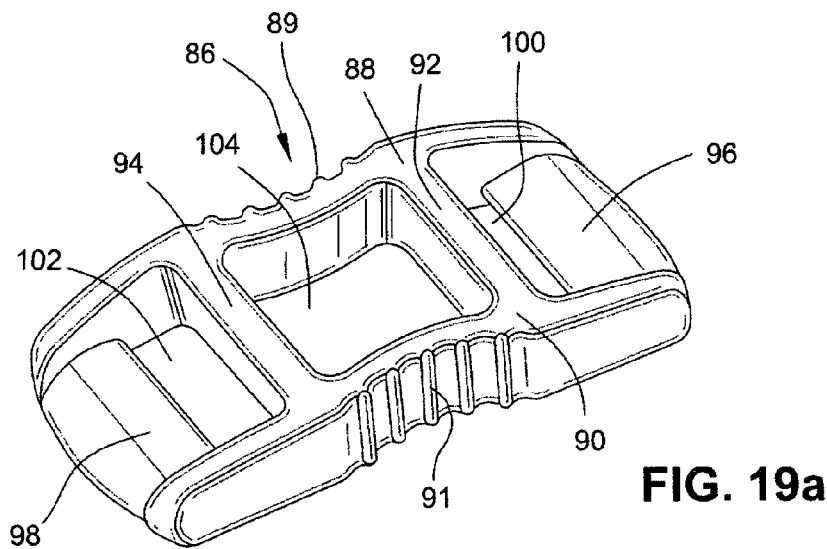
FIGS. 19a-19e schematically illustrate a ladder lock connector according to a sample embodiment.
Figure 19B:
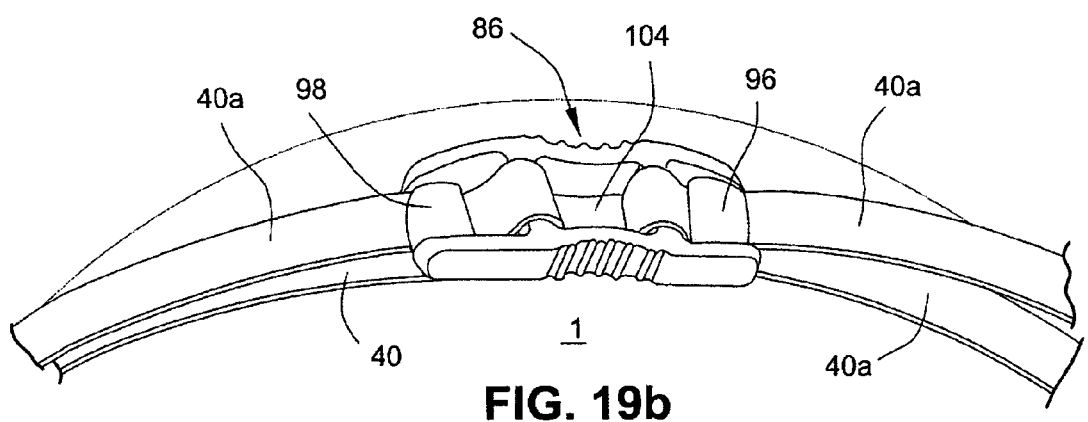

Referring to FIGS. 19a and 19b, the straps of the seal positioning and stabilizing structure, for example top straps 40, may be secured by a ladder lock connector 86. The ladder lock connector 86 may comprise a first side member 88 and a second side member 90. A first cross member 92 and a second cross member 94 extend between the first side member 88 and a second side member 90. A third cross member 96 is spaced from the first cross member 92 to define a first strap slot 100. A fourth cross member 98 is based from the second cross member 94 to define a second strap slot 102. A central aperture 104 is defined between the first cross member 92 and the second cross member 94 to allow threading of ends 40a of the top straps 40 through the central aperture 104 and over respective cross members 92, 94 and under respective cross members 96, 98, as shown in FIG. 19b. As shown in FIG. 19a, third and fourth cross members 96, 98 are wider than first and second cross members 92, 94 to increase the amount of contact between the cross members 96, 98 and the ends 40a of the straps 40. The increased width of the third and fourth cross members 96, 98 thus increases the frictional contact between the ladder lock connector 86 and the straps 40 to provide a more secure fitting of the seal positioning and stabilizing structure.

As shown in FIG. 19a, the first and second side members 88, 90 may include textured surfaces 89, 91, respectively, configured to improve a user's grip on the connector 86 to facilitate connection and/or adjustment of the straps 40 with respect to the connector 86. The textured surfaces 89, 91 may be, for example, ridges. Additionally, the side members 88, 90 may each include a depression at the textured surfaces 89, 91 to receive the user's fingers.

Figure 19C:
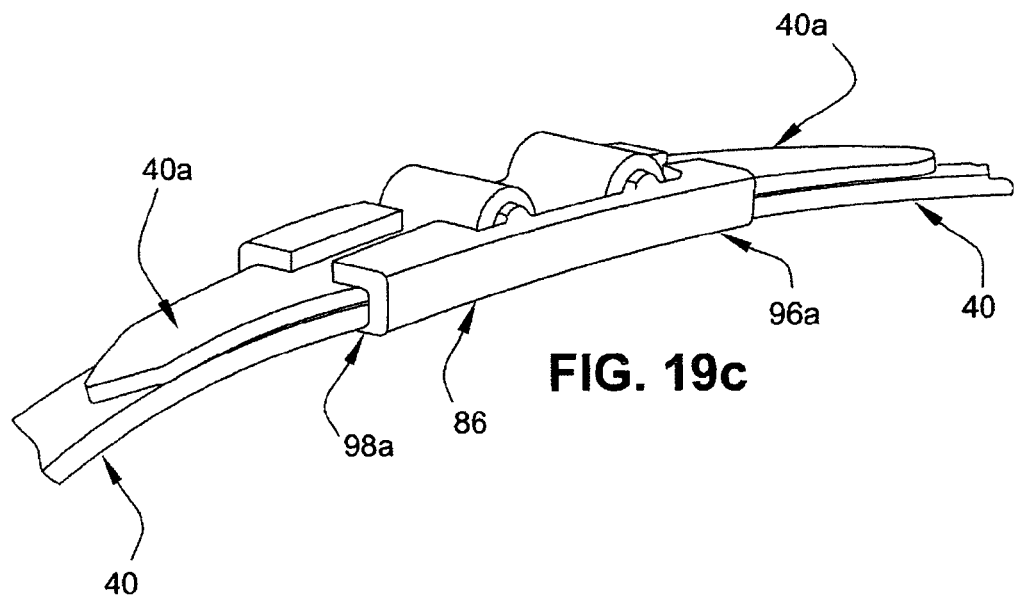
Figure 19D:
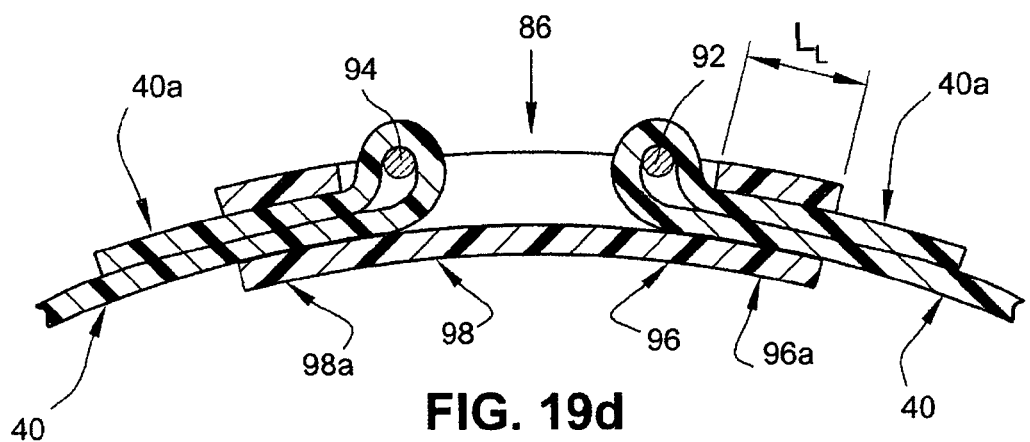
Figure 19E:
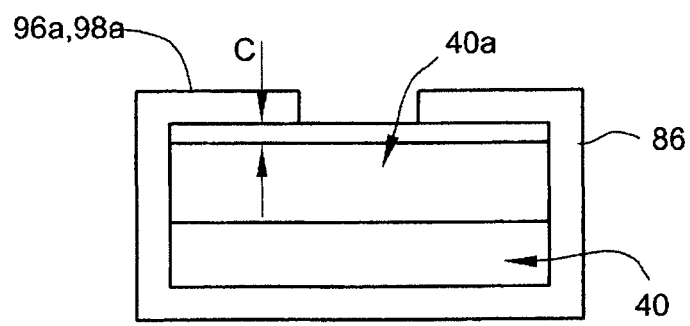

In a variant form, shown in FIGS. 19c-19e, ladder lock connector 86 may have leaders 96a and 98a to ensure that end 40a of straps 40 are aligned correctly. The ladder lock connector 86 may only be adjusted when in the configuration shown in FIG. 19b. If silicone seal positioning and stabilizing structure is used, it is unlikely that ladder lock connector 86 will remain aligned as shown in FIG. 19b due to the flexibility of silicone (for example, the ladder lock connector 86 tends to rotate 90°). To resolve this, leaders 96a and 98a may be extended distally from cross members 96 and 98. The leaders 96a and 98a may be generally rectangular or any other desirable shape. The leaders 96a and 98a may enclose straps 40 and ends 40a or may enclose only a portion of straps 40 and ends 40a. The leaders 96a and 98a may be about 5-30 mm long, for example about 10 mm long, as indicated by $L_L$ in FIG. 19d. The leaders 96a and 98a may closely conform to the perimeter formed by straps 40 and ends 40a, i.e. the outline of the strap 40 and the strap end 40a when looped through the connector. Alternatively, as shown in FIG. 19e the leaders 96a and 98a may leave at least a 1 mm clearance C, for example about 2 mm, as another example no more than about 10 mm, around the perimeter formed by straps 40 and ends 40a.

Discretely Adjustable Strap Connectors

Figure 20A:
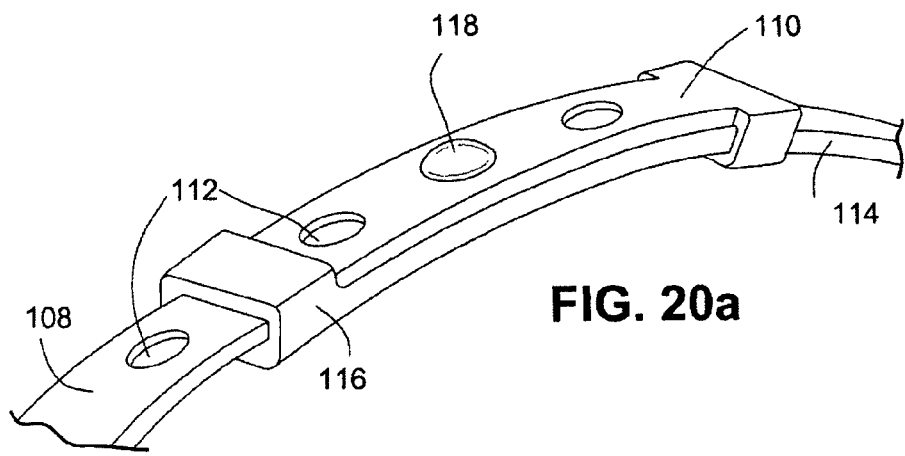
FIGS. 20a and 20b schematically illustrate a seal positioning and stabilizing structure strap connector according to a sample embodiment.
Figure 20B:
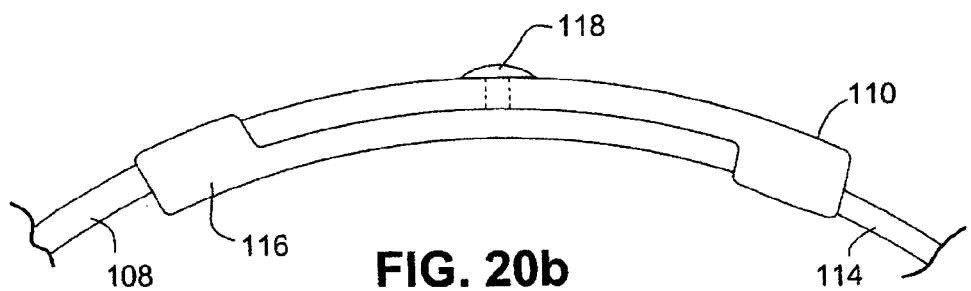

Referring to FIGS. 20a and 20b, a strap connector according to another sample embodiment comprises a first strap 108 having a first strap connector 110 formed at an end thereof. A second strap 114 has a second strap connector 116 provided at an end thereof. The second strap 114 may comprise a stud 118 that is insertable into a selected aperture 112 formed in the end of the first strap 108. The stud 118 may be generally mushroom shaped in order to lock the first strap 108 in position. The seal positioning and stabilizing structure may thus be adjusted by selecting the appropriate aperture 112 that provides the most comfortable fit for the patient while maintaining an effective seal between the patient interface structure and the patient's airways.

Figure 21A:
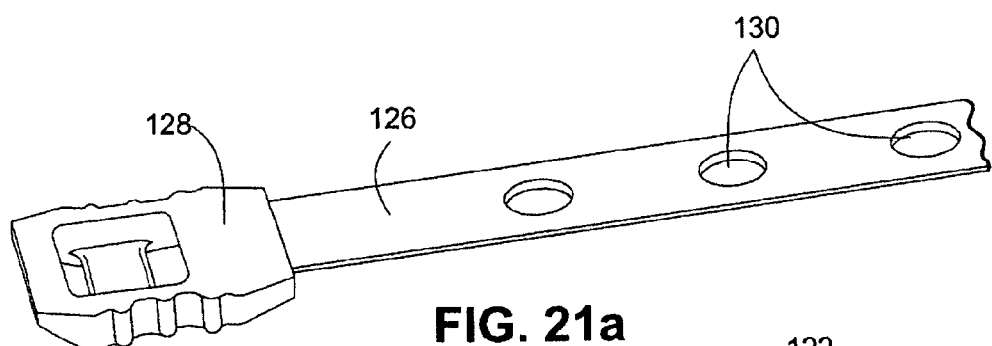
FIGS. 21a and 21b schematically illustrate another sample embodiment of a seal positioning and stabilizing structure strap connector.
Figure 21B:
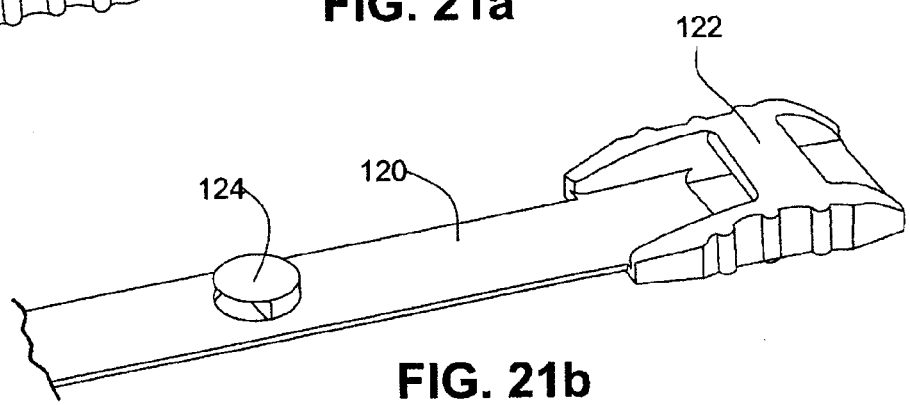

Referring to FIGS. 21a and 21b, a seal positioning and stabilizing structure strap connector assembly according to another sample embodiment comprises a first strap 120 having a stud 124 formed on an end thereof. A guide 122 is provided at the end of the first strap 120. A second strap 126 of the seal positioning and stabilizing structure may comprise a plurality of apertures or holes 130 that are selectively received by the stud 124 of the first strap 120. The second strap 126 may comprise a ladder lock connector 128 and an end thereof. The second strap 126 is threaded through the guide 122 of the first strap 120 and the stud 124 is inserted into a selected hole or aperture 130 to adjust the fitting of the seal positioning and stabilizing structure.

Referring to FIGS. 22a-23c, a seal positioning and stabilizing structure strap connector assembly according to another sample embodiment comprises a first strap 300 having a spring 302 attached on an end thereof. A second strap 301 of the seal positioning and stabilizing structure may comprise a plurality of ridges or corrugations 303 that are selectively received by the spring 302 of the first strap 300. Spring 302 may comprise a resilient finger 325 that is able to flex when corrugations 303 are pulled past the resilient finger 325 when force F is applied. As shown in FIG. 22a, the resilient finger may be provided on a resiliently cantilevered finger 305 of the spring 302. As also shown in FIG. 22a, the spring 302 may include a cross bar 307 and the first strap 300 may be connected to the spring 302 by looping an end of the first strap 300 around the cross bar 307. Alternatively, the spring 302 may be integrally formed with the first strap 300 as shown in FIGS. 23a-23c.

Main Strap Connectors

Referring to FIGS. 24a-24p, the left main strap 74l of the seal positioning and stabilizing structure comprises a strap connector 82 configured to receive one end of a rear strap of the seal positioning and stabilizing structure. The left main strap 74l also includes a patient interface structure connector 84l, e.g. a generally triangular cut out, is configured to receive left connector of the patient interface structure. The left main strap 74l also includes a plurality of locking projections 75 and a final locking projection 77. The locking projection 75 may have a generally round, oval, or elliptical configuration. The final locking projection 77 is larger than the locking projections 75 and extends above the locking projection 75, as shown for example in FIG. 24b, to prevent the seal positioning and stabilizing structure from being completely disassembled.

Referring to FIGS. 24e-24h, the right main strap 74r of the seal positioning and stabilizing structure comprises a strap connector 82 configured to receive the other end of the rear strap. The right main strap 74r also includes a patient interface structure connector 84r, e.g. cut out, that is configured for connection to a right connector of the patient interface structure. A locking connector 79, for example a ladder locking connector, is provided at an end of the right main strap 74r to receive the end of the left main strap 74l. As shown in FIG. 24i, the end of the left main strap 74l is inserted into the ladder locking connector 79 in the direction shown by the arrow to connect the left main strap 74l to the right main strap 74r. The end of the left main strap 74l may include a depression 74d to aid in insertion of the end through the locking connector 79.

As shown in FIG. 24l, the locking connector 79 includes a locking projection 81 that is configured to engage the left main strap 74l between locking projections 75 to maintain the connection between the left and right main straps 74l, 74r. The locking projection 81 is larger than the space between corresponding locking projections 75 to improve the retention of the main straps 74l, 74r. As shown in FIG. 24l, the final locking projection 77 is higher than the locking projection 75 to prevent the seal positioning and stabilizing structure from being completely disassembled. It should be appreciated that the main straps 74l, 74r and the locking projections 75, 77, 81 may be formed of material that is flexible enough to permit disassembly upon application of a sufficient force. The main straps 74l, 74r and the locking projections 75, 77, 81 may be configured to resist disassembly due to forces such as tube drag or forces normally applied to the seal positioning and stabilizing structure while wearing, and/or sleeping with, the mask system. An advantage of molding the main strap connectors into the straps is that it simplifies the manufacturing process, and is more cost-effective, since an additional fastener is not required.

As shown in FIG. 24l, a slot 83 is provided in the right main strap 74r to permit the end of the left main strap 74l to flex downwardly as the locking projection 81 engages the locking projections 75. The slot 83 permits the portion of the left main strap 74l that extends over the slot 83 to be displaced downwardly as the locking projection 81 engages the left main strap 74l between locking projections 75.

Referring to FIG. 24m, a rear strap 85 may be connected to the main straps 74l, 74r through the strap connectors 82. Ends 85e of the rear strap 85 may be provided with hook or loop type fasteners to engage corresponding loop or hook fastener material provided on the rest of the rear strap 85 to permit adjustment of the length of the rear strap 85 extending between the main straps 74l, 74r. Although FIGS. 24m-24q show the rear strap 85 as having two adjustable ends 85e, it should be appreciated that the rear strap 85 may be provided with only one adjustable end.

The durometer of the left main strap 74l may be higher in specific areas to provide increased durability, ease of adjustment, and maintenance of shape. For example, the strap connector 82, the portion surrounding the cut out 84l, the locking projections 75 and the final locking projection 77 may be provided with a higher durometer than the other portions of the left lateral member 74l. The higher durometer of the locking projection 75 and the final locking projection 77 improve the function of the ladder lock buckle formed by the connection of the locking projection 75 with the ladder locking connector 79 of the right main strap 74r. The higher durometer provided at the strap connector 82 may improve the durability of the seal positioning and stabilizing structure. The silicone material surrounding the slot of the strap connector 82 may also be of a thickness sufficient to prevent the slot from stretching too much in use. The higher durometer of the portion surrounding the cut out 84l may improve connection stability and improve durability.

Similarly, the right main strap 74r may have an increased durometer at the ladder locking connector 79, the strap connector 82 and the portion surrounding the cut out 84r to provide benefits similar to that discussed above with respect to the left main strap 74l.

As shown in FIGS. 24a-24q, the left and right main straps 74l, 74r are connected at top portion of the patient's head. The rear strap 85 does not include a connection such as a buckle or ladder lock connector. This configuration permits the patient to sleep on either side, or on the patient's back, without the ladder lock connector 79 causing any discomfort.

Figure 24R:
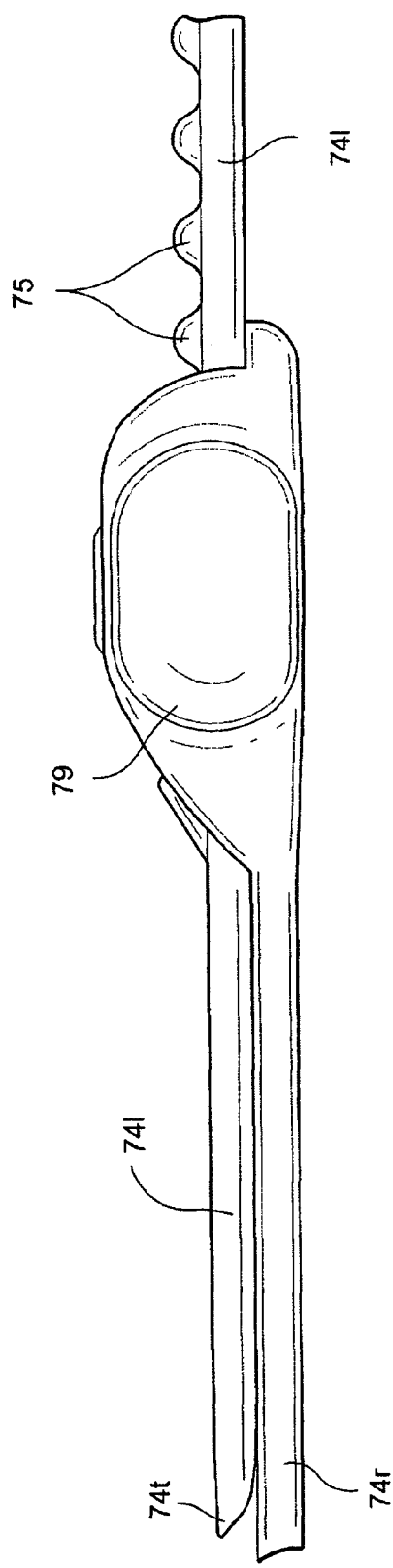
FIG. 24r schematically illustrates a strap connector according to another sample embodiment.

Referring to FIG. 24r, the left main strap 74l may include a tapered end 74t that facilitates insertion of the left main strap 74l into the connector 79 of the right main strap 74r.

Referring to FIGS. 25a-25d, according to a variant the left main strap 74l may be provided with locking projections 75, but without a final locking projection. As shown in FIG. 25d, the locking projection 81 of the ladder locking connector 79 may be generally about the same size as the locking projections 75 of the left main strap 74l. This permits the connection of the main straps 74l, 74r in a comparatively easier manner than the connection disclosed in FIGS. 24a-24p.

The right and left main straps 74r, 74l may be adjustable by a spring loaded clip that, when squeezed together, opens up and allows the lateral side members to pass through, but when not squeezed holds the straps in a locked position. Such a spring loaded clip is similar to a draw cord that is used to allow for adjustment of a cord, for example a cord that functions as a bag closure or a cord that adjust the fit of a hat or cap.

Referring to FIG. 25e, in an alternative embodiment, the right main strap 74r may be provided with a slit or opening that, when relaxed, is closed, but when squeezed at its furthest edges (as shown by the arrows), opens up and allows the left main strap 74l to pass through the slit or opening. It should be appreciated that the left main strap may include the slit or opening and the right main strap may be inserted therein.

The right and left main straps 74l, 74r of the main strap loop 74 may be formed, for example, from silicone. The silicone may be molded to comprise mushroom shaped studs 74m on both lateral side members 74l, 74r. The studs 74m, when pushed together, create an interference fit as shown in FIG. 25f. The studs 74m may be any other shape, such as a tree shape, an arrow shape, or a lollipop shape. The studs 74m may also be retrofittable to the lateral side members 74l, 74r or molded with the lateral side members 74l, 74r.

Additional Strap Connectors

Hook and loop fastener material, e.g. VELCRO®, may be provided to the main straps 74r, 74l, i.e. hook material on one lateral side member and loop material on the other. The hook and loop fastener material may be attached to the main straps by, for example, adhesive or overmolding the material into the main straps. Alternatively and/or additionally, other adjustment mechanisms, such as magnets, elastic or push clips, may be overmolded into the lateral side members. A preferred form of patient interface in accordance with the present technology includes three points of lengthwise adjustment: one on the crown of the patient's head for lengthwise adjustment of the main loop, and one on either side of the patient's head (a sub-total of two) generally above the ears for lengthwise adjustment of the rear strap. Some prior art patient interfaces may require adjustment of ten separate points in order to find a suitable seating for the headgear, making the process of fitting more complicated. Preferably the rear strap does not include a buckle at the rear of the patient's head, as such a buckle may be uncomfortable to lie on.

Figure 18A:
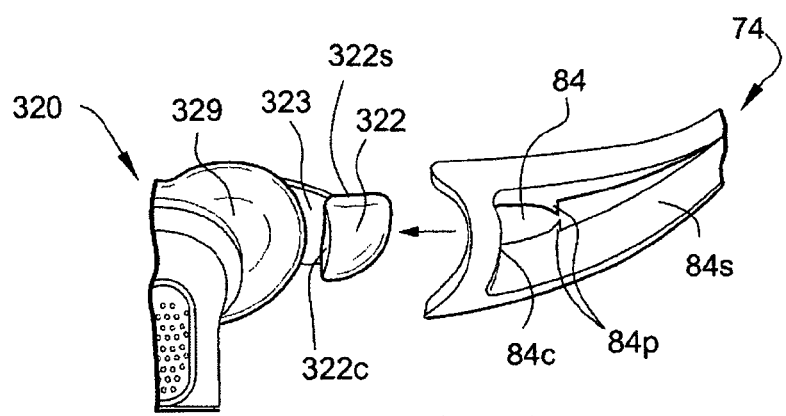
FIGS. 18a-18c schematically illustrate a connection of the patient interface structure to the seal positioning and stabilizing structure according to one sample embodiment.
Figure 18B:
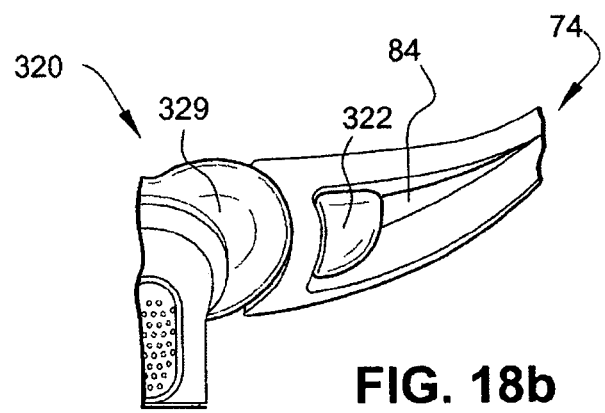
Figure 18C:
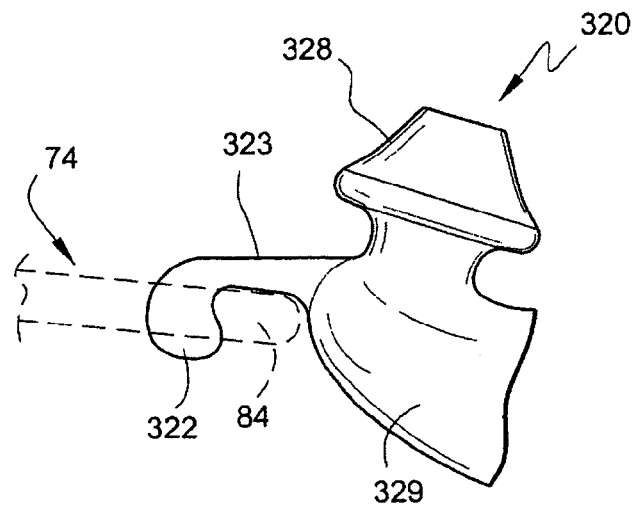

Patient Interface Structure and Seal Positioning and Stabilizing Structure Connectors Connectors Extend Toward Flexible Base of Patient Interface Structure In use, the patient interface structure 320 may be connected to the main strap loop 74 of the seal positioning and stabilizing structure by inserting a connector 322 into the patient interface structure connector (e.g. cut out) 84 of each main strap 74r, 74l. As shown, for example in FIG. 17c, the connector 322 is wider than the patient interface structure extension 323. The connector 322 is also wider than the cut out 84 in the main strap loop 74. The connector 322 is inserted through the cut out 84 to connect the patient interface structure 320 to the main strap loop 74, as shown in FIGS. 18a-18c. As shown in FIGS. 16a and 17a, the cut out 84 and the connector 322 include complementary surfaces 84c, 322c, respectively, that are engaged when the connector 322 is connected to the main strap 74r, 74l. The connector 322 also includes sloped side walls 322s (FIG. 17c) that engage with sloped walls 84s (FIG. 16a) of the cut out 84 when the connector 322 is connected to the main strap 74r, 74l so that the connector 322 and the main strap 74r, 74l present a flush surface upon connection, as shown in FIG. 18b. As shown in FIG. 18a, the cut out 84 may include inwardly directed projections 84p that will engage the end of the connector 322 upon connection of the patient interface structure 320 to the main strap loop 74 (i.e. the right and left main straps 74r, 74l) to provide a more secure attachment of the patient interface structure 320 to the main strap loop 74 of the seal positioning and stabilizing structure.

Connectors Extend Toward Seal of Patient Interface Structure

Figure 18D:
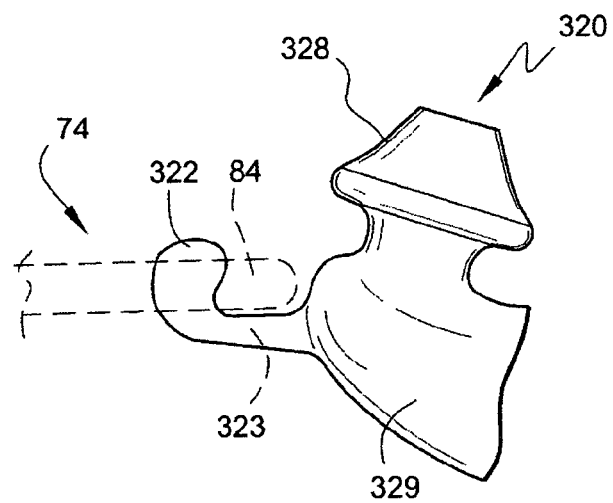
FIGS. 18d-18q schematically illustrate a connection of the patient interface structure to the seal positioning and stabilizing structure according to other sample embodiments.
Figure 18E:
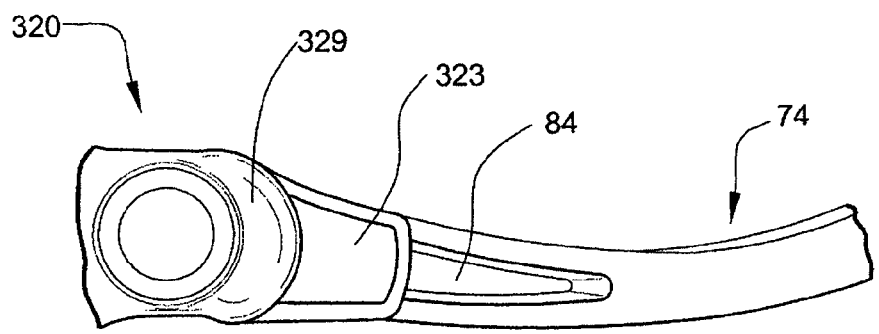
FIGS. 18r and 18s schematically illustrate cross sections of a patient interface structure according to a sample embodiment.
Figure 18F:
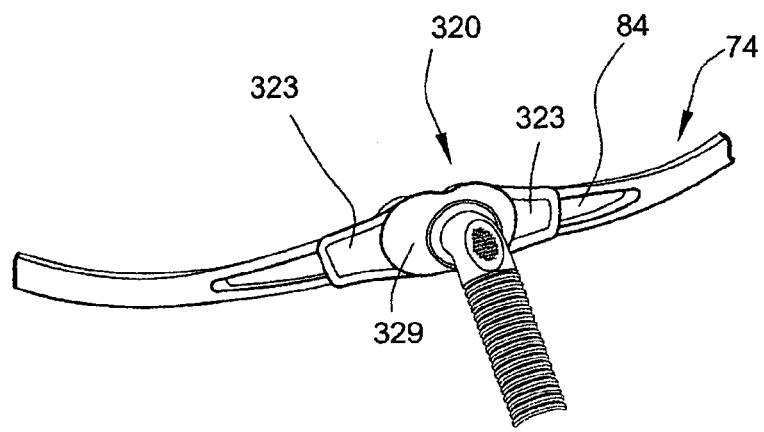

According to another sample embodiment, shown in FIGS. 18d-18f, the connector 322 may extend from the extension 323 generally in the direction of the nozzles 328 and away from the flexible base 329, as shown in FIG. 18d. The connector 84 is placed over the connector 322 so that when the connector 322 is engaged with the connector 84, the extension 323 is visible, as shown in FIGS. 18e and 18f. The assembly may be secured in the same manner described above with respect to FIGS. 18a-18c and may provide a more secure connection when the mask system is in use.

Figure 18G:
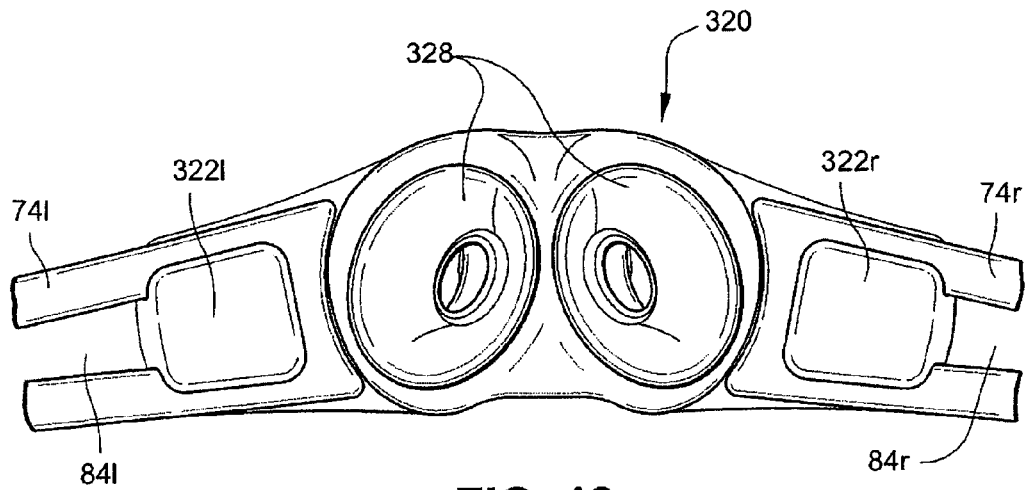

Referring to FIG. 18g, the left and right connectors 322l, 322r, respectively, of the patient interface structure 320 are connected to the left and right main straps 74l, 74r, respectively, of the seal positioning and stabilizing structure through the left and right connectors (e.g. cut outs) 84l, 84r, respectively. The geometry of the connectors 322l, 322r matches the geometry of the cut outs 84l, 84r to provide an intuitive assembly for the user. The user may get a tactile indication that the connectors 322l, 322r are properly inserted into the cut outs 84l, 84r and assembled in the connected position.

Connectors with Alignment Indicators

Figure 18H:
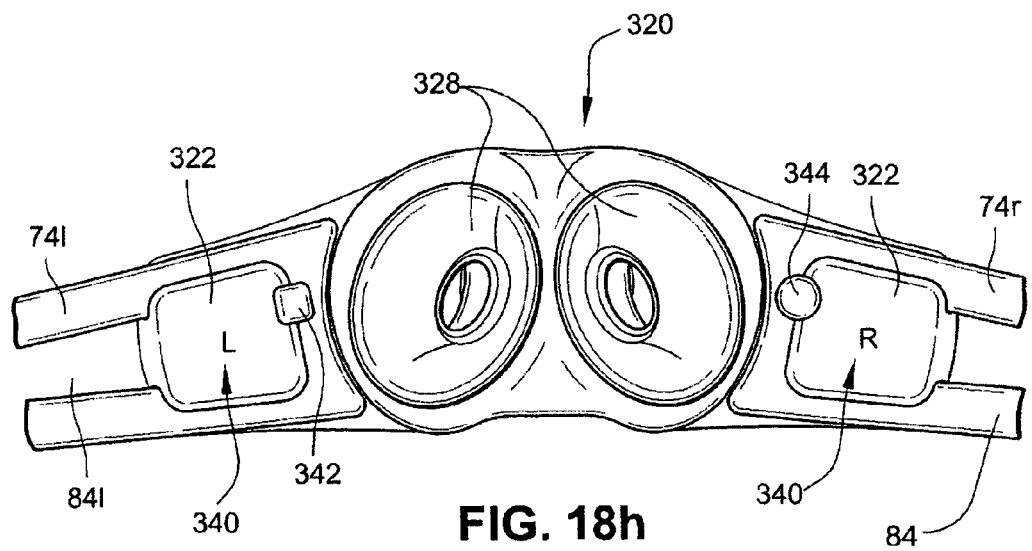

Referring to FIG. 18h, in order to ensure correct alignment of the patient interface structure 320 into the left main strap 74l and the right main strap 74r of the seal positioning and stabilizing structure, the connectors 322l, 322r may include indicia 340 which indicate the left side and the right side. The connectors 322l, 322r may also include a left indicator tab 342 and a right indicator tab 344 to align the patient interface structure 320 correctly in the seal positioning and stabilizing structure. As shown in FIG. 18h, the indicator tabs 342, 344 may have different shapes to facilitate alignment of the patient interface structure 320 in the seal positioning and stabilizing structure. Although the alignment indicator tabs 342, 344 are shown on the connectors 322l, 322r of the patient interface structure 320, it should be appreciated that the alignment indicator tabs may be provided on the main straps 74l, 74r of the seal positioning and stabilizing structure, or that the alignment indicator tabs may be provided on both the connectors of the patient interface structure and the main straps of the seal positioning and stabilizing structure.

Figure 18I:
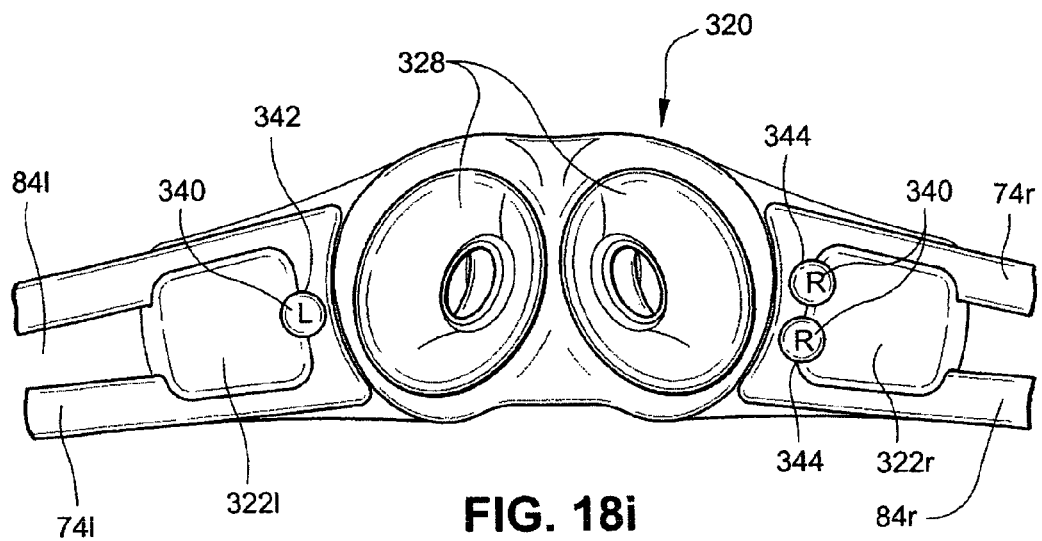

Referring to FIG. 18i, the connectors 322l, 322r, may include a different number of alignment indicator tabs 342, 344 to indicate the proper direction. For example, the left connector 322l may include one indicator tab 342 and the right connector 322r may include two indicator tabs 344. It should also be appreciated that the position of the alignment indicator tabs 342, 344 may be provided in different places to indicate the direction. For example, the left indicator tab 342 may be provided on a side of the connector 322l and the right indicator tabs 344 may be provided on top of the right seal positioning and stabilizing structure connector 322r. It should also be appreciated that the indicia 340 may also be provided, for example, on the alignment indicator tabs 342, 344.

Figure 18J:
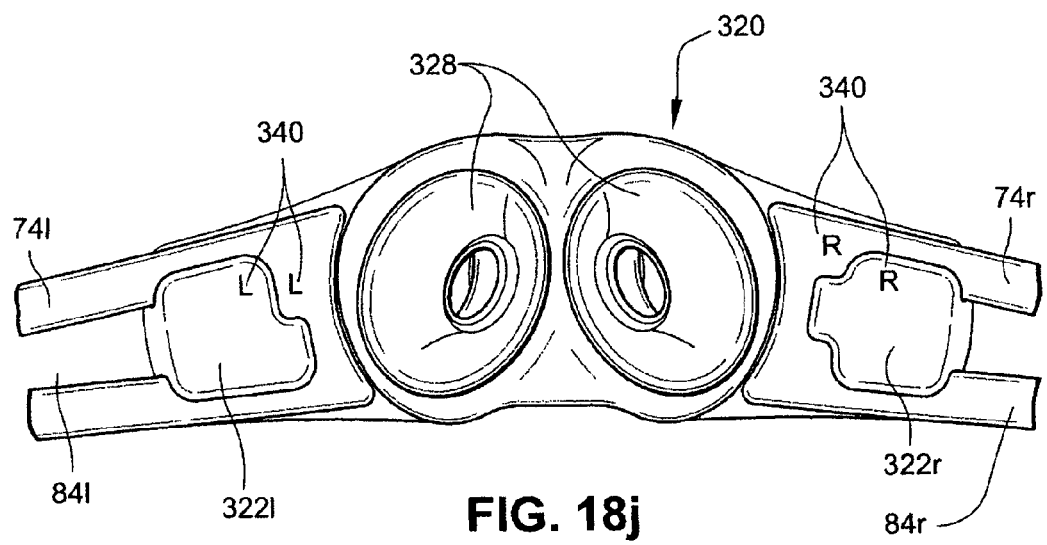
Figure 18M:
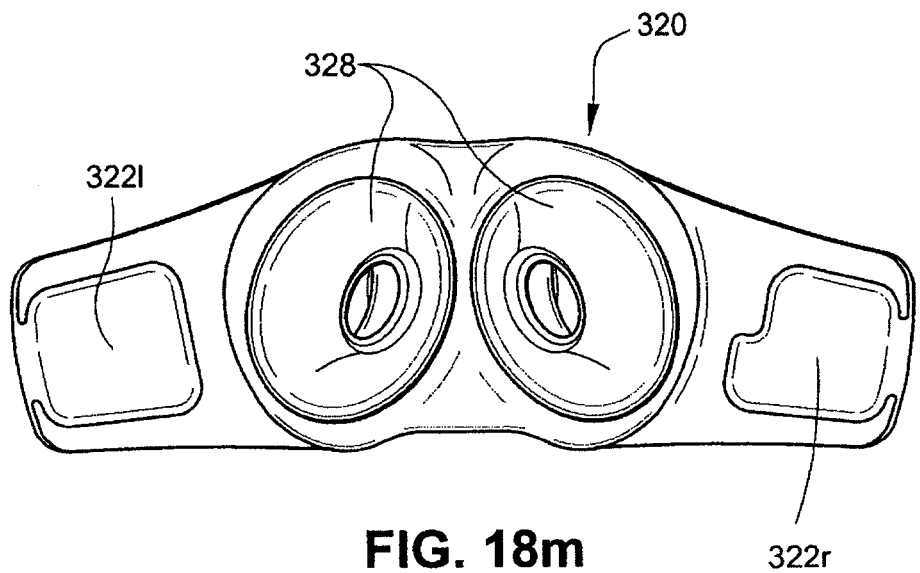
Figure 18N:
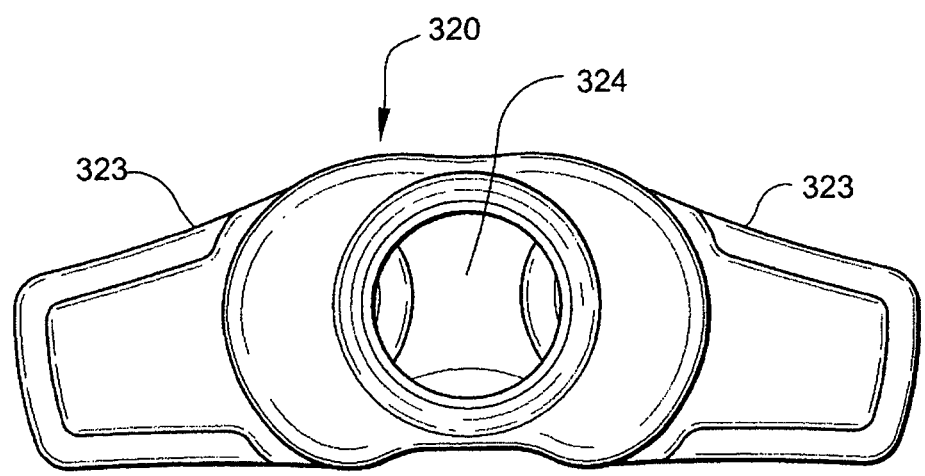

As shown in FIG. 18j, according to another sample embodiment, the patient interface structure 320 may be aligned properly with the seal positioning and stabilizing structure by providing the left seal positioning and stabilizing structure connector 322l with a different shape than the right seal positioning and stabilizing structure connector 322r. As shown in FIG. 18k, the left cut out 84l has a shape corresponding to the left connector 322l and the right cut out 84r has a different shape corresponding to the differently shaped right connector 322r. The differently shaped connectors and cut outs ensures proper alignment of the patient interface structure 320 with the seal positioning and stabilizing structure in the assembled position shown in FIG. 18l.

Figure 18O:
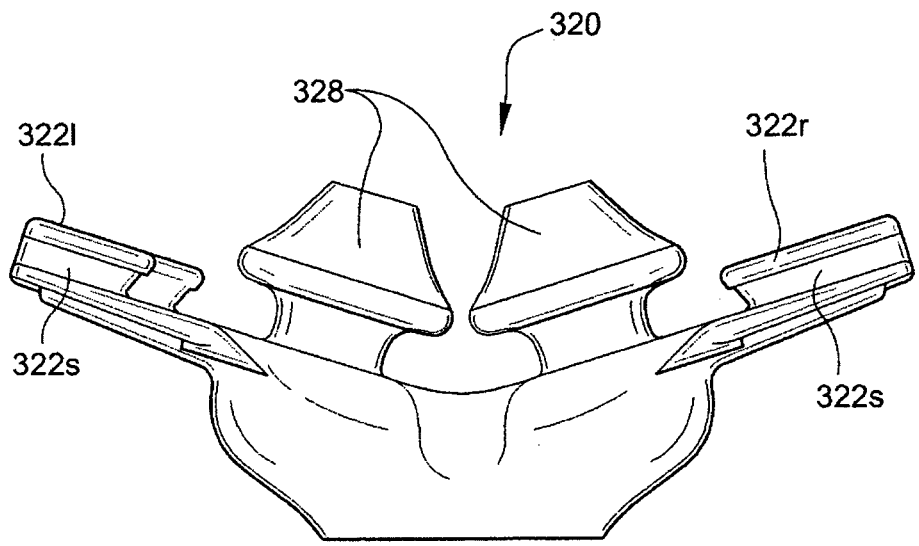
Figure 18P:
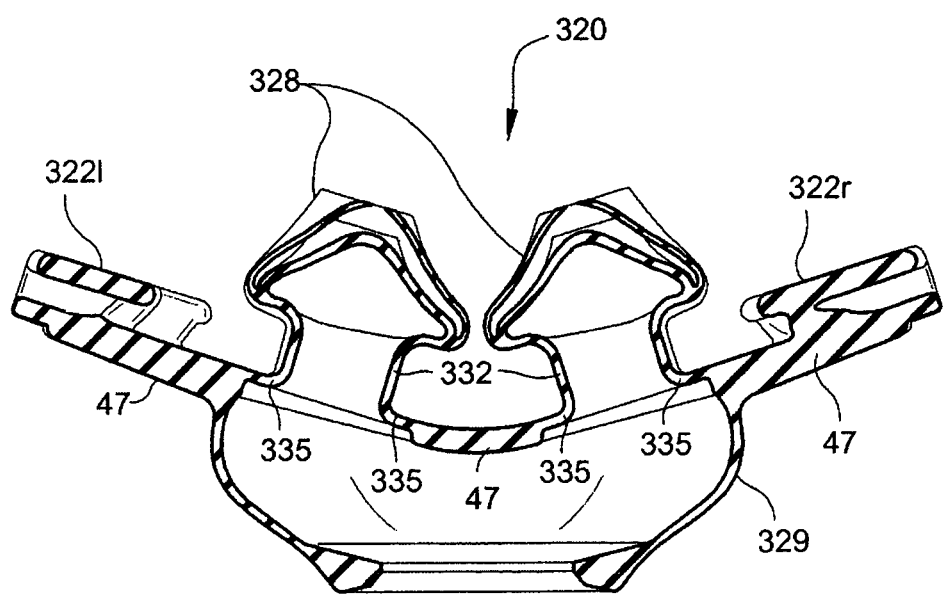

Referring to FIGS. 18m-18p, the seal positioning and stabilizing structure connectors 322l, 322r may face upwards towards the pillows 328 of the patient interface structure 320. This configuration may be provided to avoid accidental disassembly of the patient interface structure 320 from the seal positioning and stabilizing structure. As shown in FIGS. 18o and 18p, the connectors 322l, 322r may include stepped portions 322s that engage with stepped portions 84s of the lateral members 74l, 74r so that the connection between the patient interface structure and the seal positioning and stabilizing structure cannot be accidentally disassembled by pulling the seal positioning and stabilizing structure up from the tabs. The seal positioning and stabilizing structure must be pushed inwards towards the nasal pillows 328 to disengage the stepped portions 322s and then pulled upwards in order to disassemble the connection of the patient interface structure and the lateral members of the seal positioning and stabilizing structure.

Figure 18Q:
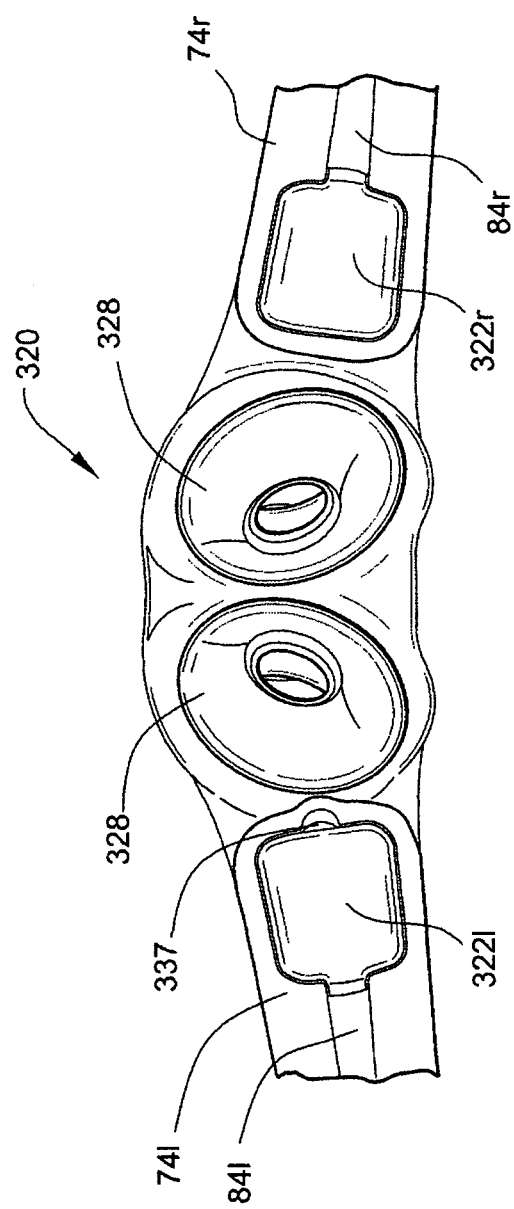

As shown in FIG. 18q, the cut out 84l may include a notch, or cut out 337, to improve bending of the material of the left strap loop 74l to facilitate connection and disconnection of the connector 322l from the cut out 84l. It should be appreciated that the cut out 337 may be alternatively, or additionally, provided to the right strap loop 74r.

As discussed above, the seal positioning and stabilizing structure is not connected to any "hard" parts, for example a rigid polycarbonate shell or frame such as used in prior art mask assemblies, although it should be appreciated that patient interface structure may be connected to a hard part, such as a rigid frame or shell, that is in turn connected to the seal positioning and stabilizing structure.

Decoupling Arrangements
Hinge or Universal Joint

Referring again to FIGS. 7a-7d, the air delivery tube 16 may be connected to the patient interface structure 32 by a decoupling arrangement 44. The decoupling arrangement 44 may comprise, for example, a hinge mechanism. The decoupling arrangement 44 may comprises a connection between the tube 16 and the patient interface structure 32 that provides more than one axis of rotation. Referring to FIG. 7d, the flexible base 6 of the patient interface structure may be divided into the lower portion 6l and the top portion 6t by a hinge or universal joint 440 to further isolate the tube drag forces from the forces of the seal positioning and stabilizing structure.

Flexible Elbow

Referring to FIG. 5b, a flexible elbow 409 may comprise a flexible "skeleton" 411 comprising a plurality of rigid hoops, or rings, 405 connected by a flexible lattice 406. An overmold 408 formed of, for example, silicone is provided over the skeleton 402 to form the flexible elbow. The rings 405 provide a minimal support structure that ensures that the elbow 400 does not collapse, but maintains the flexibility of the elbow 409 and prevent occluding.

Diaphragm

In another form, the decoupling arrangement 44 may comprise a diaphragm between an elbow connected to the tube 16 and the patient interface structure 32, or the flexible base 6 of the patient interface structure 32. The diaphragm may be a thinned section with a flat cross section. Alternatively, the cross section of the diaphragm may be wave-shaped, zigzagged, or any other desired shape.

Referring to FIGS. 5c and 5d, the elbow 400 may have a rigid collar 410 that is supported by a diaphragm 414 that is provided between the collar 410 and a rigid frame 412, or a relatively more rigid section, of the patient interface structure. The diaphragm 414 may be flat, or have a wave-shaped configuration, or a concertina-type configuration. The diaphragm 414 may be formed of, for example, silicone.

Linking Element

Referring to FIGS. 8l and 8m, seal positioning and stabilizing structure is used to stabilize a mask system on the face of the patient. However, the stabilization can be offset by air delivery tube drag forces. Typically, the frame of a mask system will direct forces from the headgear and the air delivery tube in such a way that the mask is still able to seal. In the sample embodiments, seal positioning and stabilizing structure is connected to the patient interface structure, not to the frame. The patient interface structure thus needs to direct the forces, i.e. seal positioning and stabilizing structure and air delivery tube drag forces. As shown in FIG. 8l, a patient interface structure according to an embodiment, for example the embodiment shown in FIG. 4, the air delivery tube drag force acts on the patient interface structure at the top portion 6t, which may cause the nasal pillows to be pulled away from the patient's nares. The patient interface structure shown in FIG. 8l may not be able to direct seal positioning and stabilizing structure and air delivery tube forces while maintaining a seal.

As shown in FIG. 8m, the provision of a linking element(s) to the top portion to isolate the seal positioning and stabilizing structure forces and direct the seal positioning and stabilizing structure and tube drag forces appropriately. The lines of tension force are directed through the top portion 6t of the patient interface structure 32, thereby allowing the base portion 6 of the patient interface structure 32 to decouple tube drag forces. The linking element facilitates decoupling of the top portion 6t with respect to the lower portion 6l by drawing the tension lines of force through the top portion of the patient interface structure 32 and isolates such forces from the base portion of the patient interface structure. The tension linking element isolates the tube drag force at the base portion 6 of the patient interface structure, for example the lower portion 6l, which may include, or be configured as, a gusset. By distributing the forces to the lower portion 6l, the patient interface structure is stabilized in the patient's nares in use.

Sealing Ring—First Embodiment

Figure 9A:
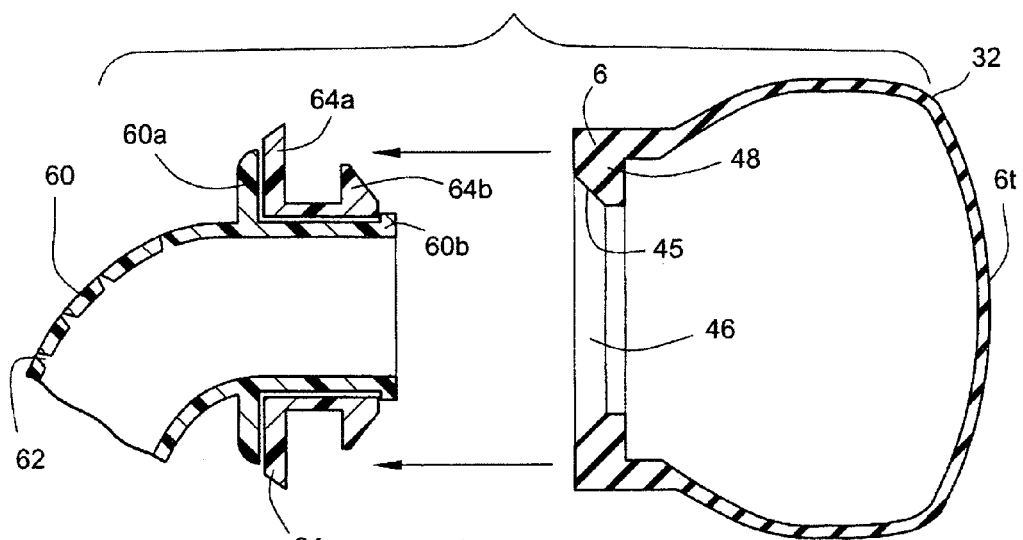
FIGS. 9a and 9b schematically illustrate a patient interface structure to elbow or frame connection in accordance with a sample embodiment.
Figure 9B:
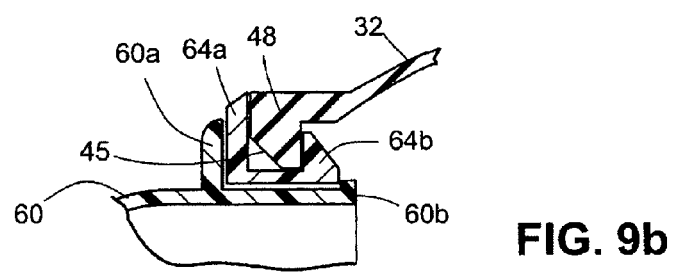

Referring to FIGS. 9a and 9b, a respiratory mask system according to another sample embodiment includes a patient interface structure 32. FIG. 9a illustrates a cross section through the flexible base 6 of the patient interface structure 32 in between the nasal pillows 4. It should be appreciated that the patient interface structure may be, for example, a nasal cushion or a full face cushion. It should also be appreciated that the patient interface structure may be formed as a compact oro-nasal interface in a manner similar to that disclosed in U.S. Patent Application Publication 2007/0144525 A1, the entire contents of which are incorporated herein by reference. For example, the compact oro-nasal interface may be modified to include connectors for the seal positioning and stabilizing structure straps provided on the patient interface structure or the nozzles. The patient interface structure 32 may be connected to an elbow 60 which may be connected to an air delivery tube. The elbow 60 may include a vent 62 to permit the exhaust of the patient's exhalation.

The patient interface structure 32 may be swivelably connected to the elbow 60 by a swivel seal ring 64. As shown in FIGS. 9a and 9b, the patient interface structure 32 may include a flexible base 6 having an aperture 46 for the introduction of the flow of breathable gas. The aperture 46 may be surrounded by a flange 48 which extends radially inwardly around the aperture 46. The flange may include a chamfer 45 extending around the circumference of the flange 48. As shown in FIG. 9b, the flange 48 of the patient interface structure 32 is received in a space between a first flange 64a and a second flange 64b of the swivel seal ring 64 to form a secure seal assembly. The chamfer 45 allows the flange 48 of the patient interface structure 32 to be inserted and removed from the space more easily. The swivel seal ring 64 is maintained on an end of the elbow 60 between a first flange 60a and a second flange 60b of the elbow 60. A radial seal is formed at the contact between the second flange 64b of the swivel seal ring 64 and the second flange 60b of the elbow 60. The connection of the flange 48 of the patient interface structure 32 to the swivel seal ring 64 permits the patient interface structure to swivel or rotate with respect to the elbow. The swivel seal ring 64 thus assists decoupling tube drag forces from the seal. The embodiment of FIGS. 9a and 9b thus replaces the patient interface structure-to-frame connection mechanism of the prior art with a patient interface structure-to-elbow connection.

Sealing Ring—Second Embodiment

Figure 17H:
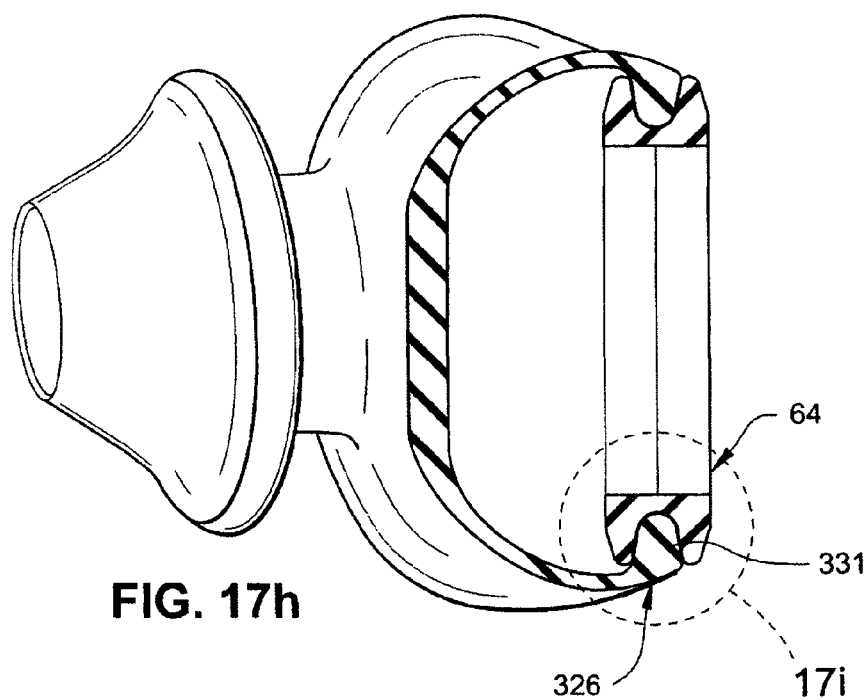
FIGS. 17h and 17i schematically illustrate a swivel seal ring according to a sample embodiment in connection with a patient interface structure according to a sample embodiment.
Figure 17I:
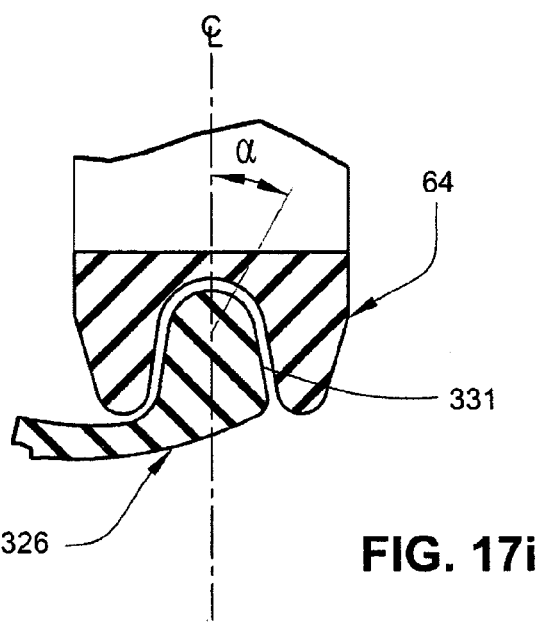

In a variant shown in FIGS. 17h and 17i, the flange 326 of the patient interface structure may have a varied thickness T3. For example, the flange 326 may be formed as a tapered flange 331 so that it is easier to insert into the swivel ring 64. The taper may be an angle a in the range of about 5°-50°, for example about 15°. The surface of the tapered flange 331 may be polished to improve sealing. Alternatively, the surface of the tapered flange 331 may be textured for easier sliding of the swivel ring 64.

Figure 17J:
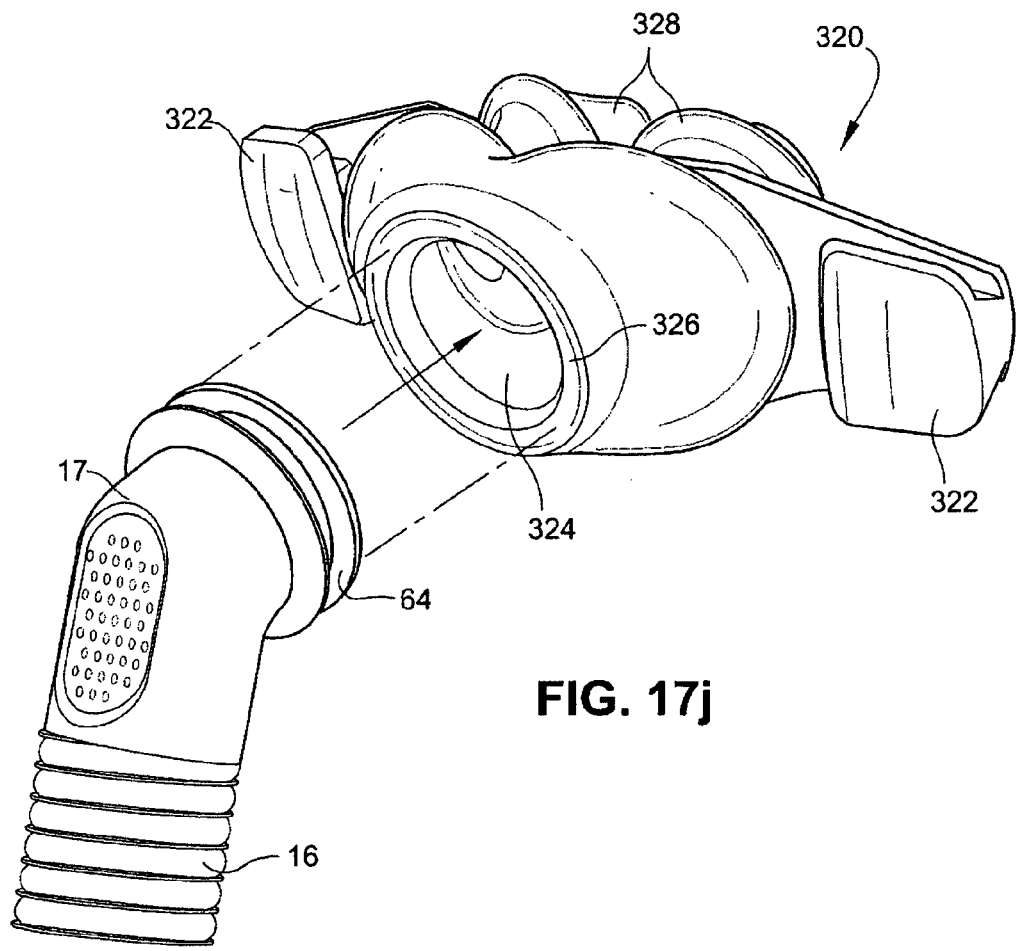
FIG. 17j schematically illustrates a patient interface system according to a sample embodiment including an air delivery tube, an elbow, a swivel seal ring, and a patient interface structure.
Figure 17K:
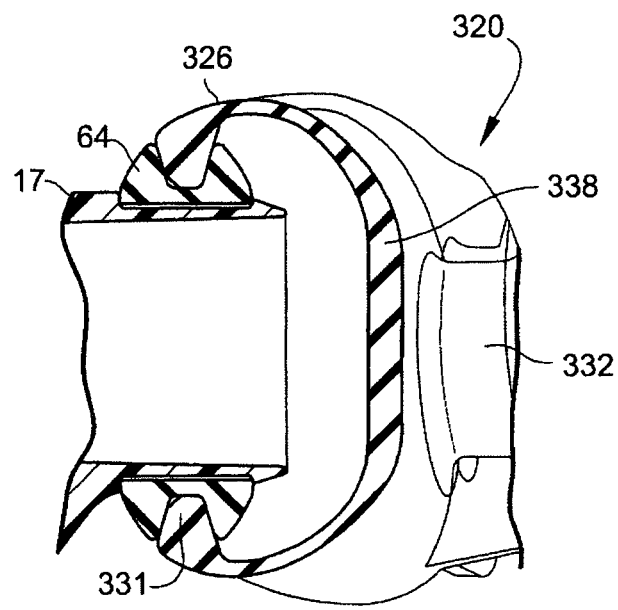
FIG. 17k schematically illustrate a seal formed between an elbow and a swivel seal ring according to a sample embodiment.

Referring to FIG. 17j, the patient interface structure 320 is connected to a swivel elbow assembly 17 having a hose 16 connected thereto by a sealing ring 64 that is insertable into the aperture 324 of the patient interface structure 320 for engagement with the flange 326. As shown in FIG. 17k, the flange 326 comprises a tapered flange 331 that is configured to be inserted into a groove or slot defined by the sealing ring 64.

The tapered flange 331 may be assembled to the sealing ring 64 by simply inserting the sealing ring 64 into the aperture 324 of the patient interface structure 320, or by inserting the tapered flange 331 of the patient interface structure 320 over the sealing ring 64, or by a combination of these actions.

The tapered flange 331 and sealing ring 64 provide a small and simple connection of the patient interface structure 320 to the swivel elbow assembly 17 that does not affect the patient interface structure performance. The sealing ring 64 also allows the swivel elbow assembly 17 to be assembled to the patient interface structure 320 in such a way as not to compromise the retention of the swivel elbow assembly 17 with the patient interface structure 320.

Sealing Ring—Third Embodiment

Figure 17L:
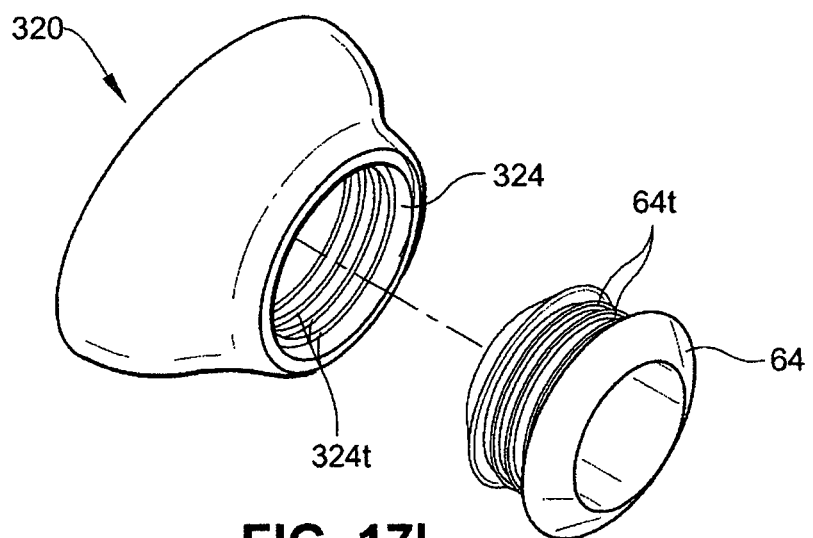
FIG. 17l schematically illustrates a seal ring according to another sample embodiment.

Referring to FIG. 17l, the aperture 324 of the patient interface structure 320 may include a threaded portion 324t and the sealing ring 64 may comprise a corresponding threaded portion 64t that allows the sealing ring 64 to be threadably fastened to the patient interface structure 320.

Sealing Ring—Fourth Embodiment

Figure 17M:
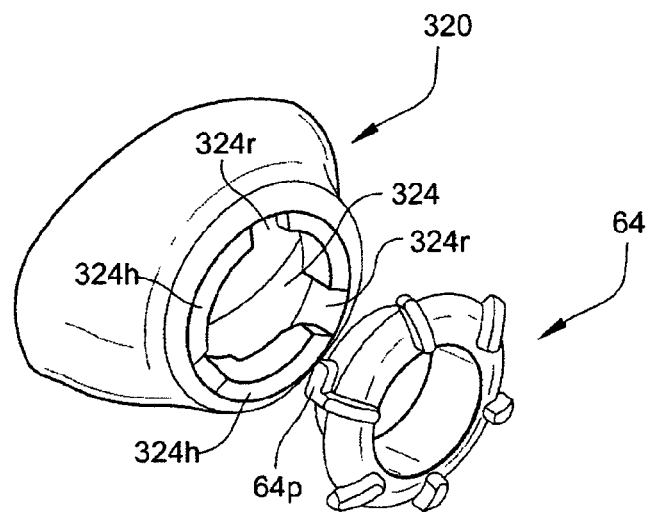
FIG. 17m schematically illustrates a seal ring according to another sample embodiment.

As shown in FIG. 17m, according to another variant, the aperture 324 of the patient interface structure 320 may have a plurality of holding portions 324h and a corresponding number of releasing portions, or openings, 324r. The sealing ring 64 comprises a corresponding number of projections 64p that are received in the releasing portions 324r and rotated into engagement with the holding portions 324h to form a bayonet type connection between the sealing ring 64 and the patient interface structure 320.

Sealing Ring—Fifth Embodiment

Figure 17N:
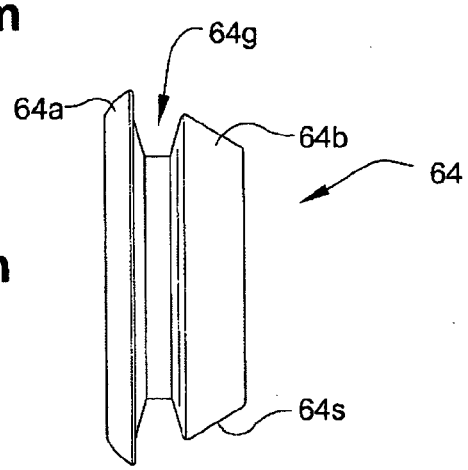
FIGS. 17n and 17o schematically illustrate a swivel seal ring according to another sample embodiment.
Figure 17O:
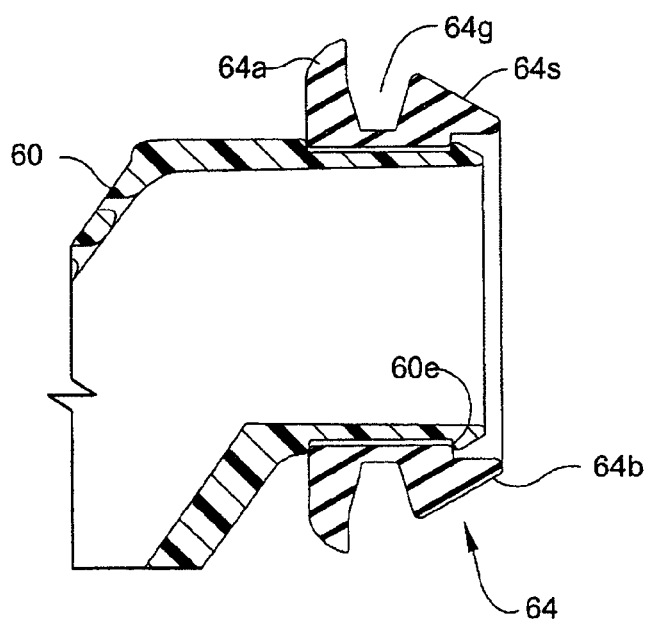

Referring to FIGS. 17n and 17o, a swivel seal ring 64 may have an asymmetrical configuration including a first flange 64a that has a larger diameter than a second flange 64b. A gap, or space, 64g is provided between the first and second flanges 64a, 64b to receive the flange of the patient interface structure. The second flange 64b comprises a sloped surface 64s that facilitates insertion of the sealing ring 64 into the aperture of the patient interface structure. The second flange 64b is configured to contact an edge 60e of the elbow 60 to form a radial seal.

Trampoline

Figure 26A:
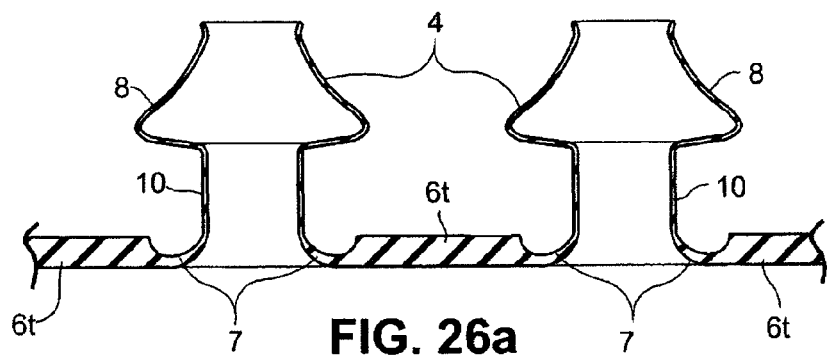
FIGS. 26a and 26b schematically illustrate nasal pillows according to a sample embodiment.
Figure 26B:
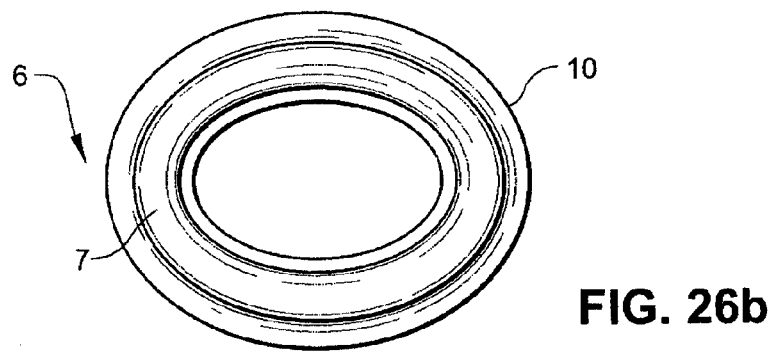

Referring to FIGS. 26a and 26b, the stalks or neck portions 10 of the nasal pillows 4 may be connected to the top portion 6t of the base portion 6 of the patient interface structure and comprise thinned, or reduced thickness, portions 7. The thinned portions 7 allow the pillows 4 to easily spring, or trampoline, and therefore adjust to suit the alar angle of the patient more readily.

In a variant shown in FIGS. 18p and 18s, the top portion 6t of the flexible base 6 may include thinned portions, or trampolines, 335 between the stalks, or neck portions, 332 of the nasal pillows 328 and the linking element 47.

Flexible Base

Figure 42A:
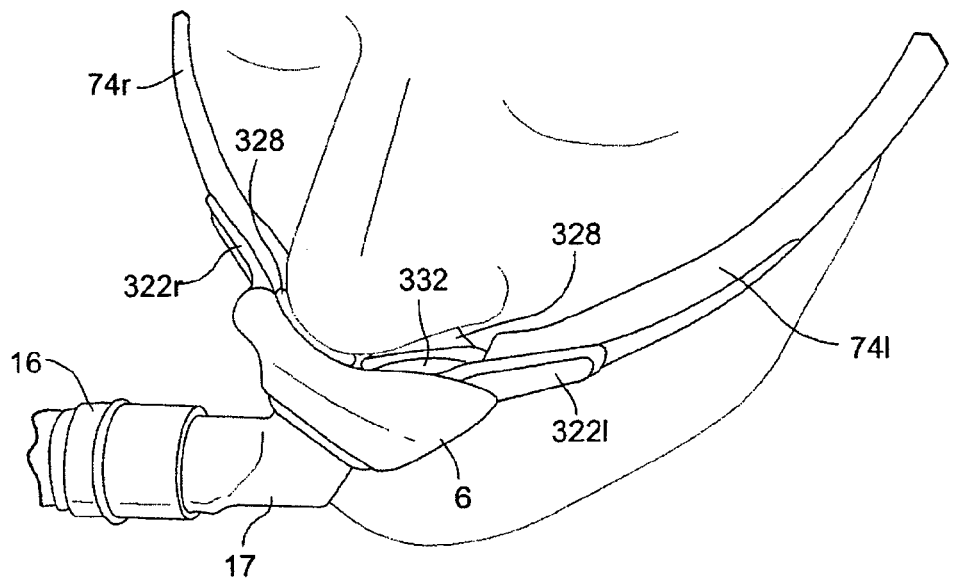
FIGS. 42a-42c schematically illustrate a patient interface system according to a sample embodiment in various stages of sealing engagement with a patient.
Figure 42B:
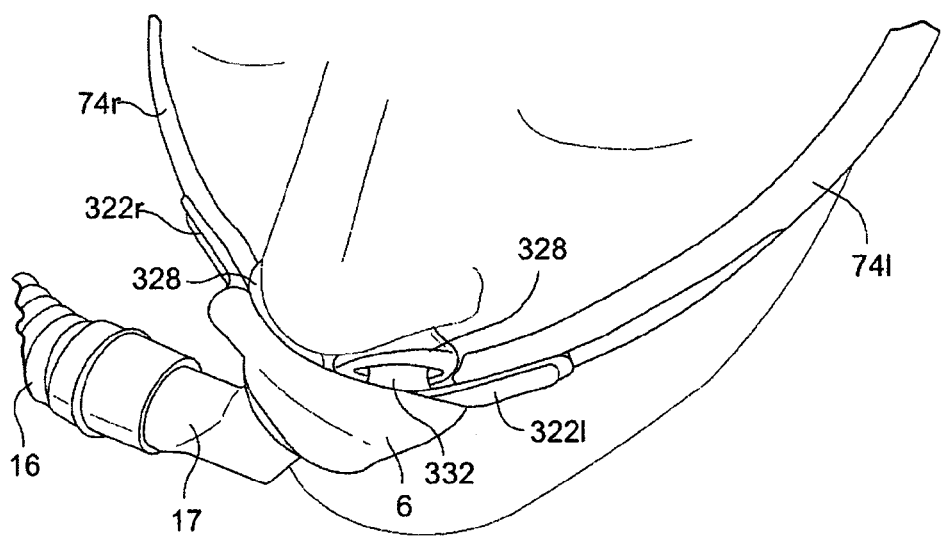
Figure 42C:
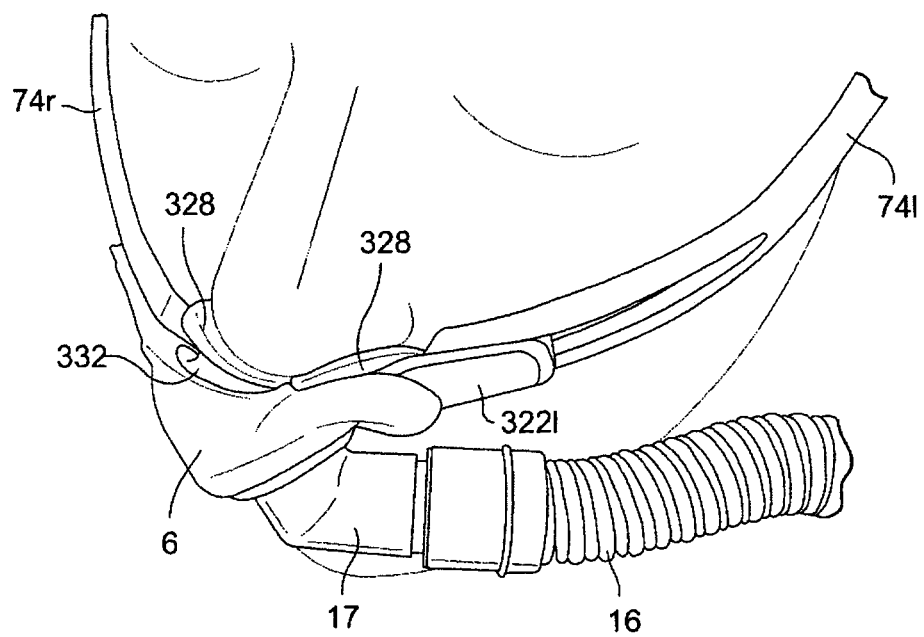

Referring to FIGS. 42a-42c, the flexible base 6 of the patient interface structure is configured to conform to wrap around the underside of the nose of the patient in use when under tension. The flexible base 6 can assist in decoupling the seal, e.g. the nasal pillows 328, from tube drag forces on the tube 16, which may be connected to the patient interface structure by the elbow 17. As shown in FIG. 42a, essentially no tube drag force is exerted on the patient interface structure. The nasal pillows 328 are both in sealing engagement with the patient's nare. Referring to FIG. 42b, a force may be exerted on the tube 16 on the right side of the patient's face. The flexible base 6 compresses on the right side of the patient's face while permitting the nasal pillow 328 on the left side of the patient's face to remain in sealing engagement with the patient's nare. As shown in FIG. 42b, stalk, or neck portion, 332 of the left nasal cushion 328 is less compressed than the stalk 332 of the right nasal cushion 328. It should be appreciated that the compressibility of the stalks 332 and, for example, thinned regions or trampolines around the stalks 332 may further assist in decoupling forces, for example tube drag, exerted on the tube or patient interface structure from the seal. As shown in FIG. 42c, in the case where tube drag is exerted to the left side of the patient's face, the left side of the flexible base 6 is compressed, as is the stalk of the left nasal pillow 328. The right nasal cushion 328 remains in sealing engagement with the patient's right nare. The stalk 332 of the right nasal cushion 328 may articulate to assist in maintaining the right nasal cushion 328 in sealing engagement.

Figure 43A:
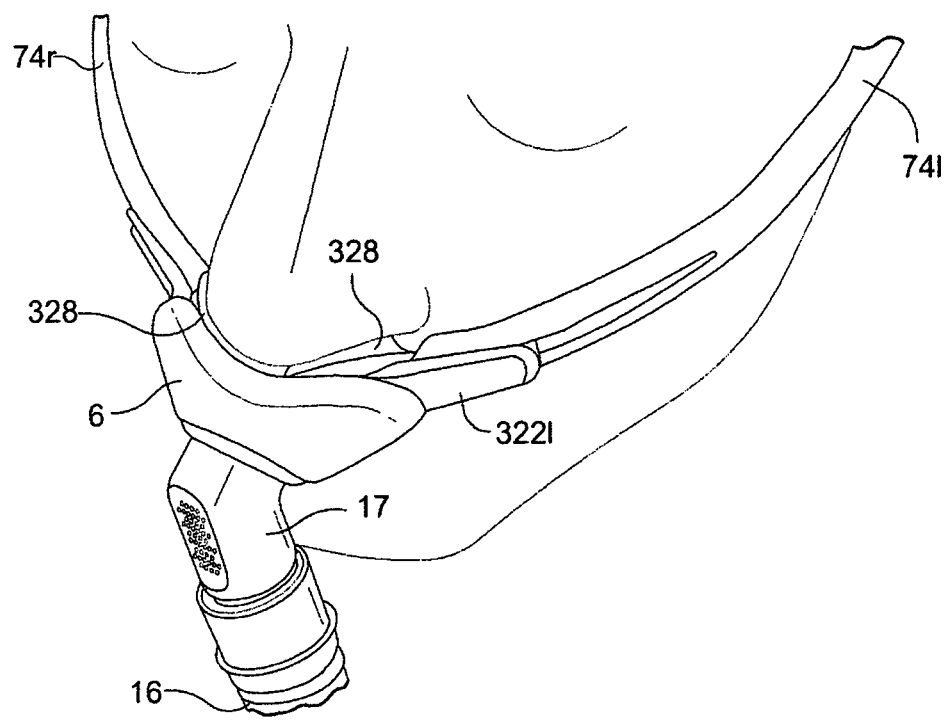
FIGS. 43a-43c schematically illustrate a patient interface system according to a sample embodiment in various stages of sealing engagement with a patient.
Figure 43B:
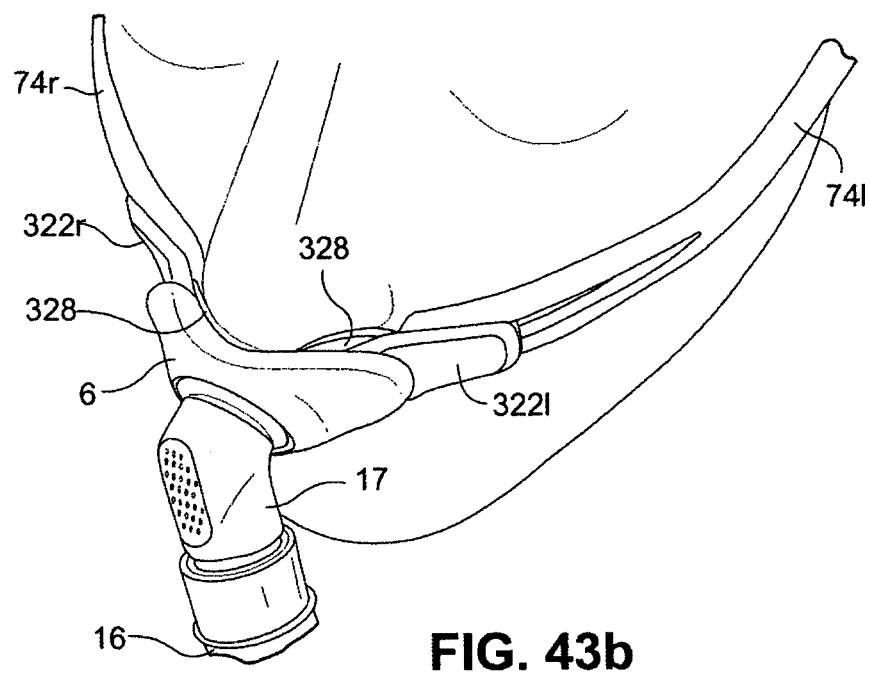
Figure 43C:
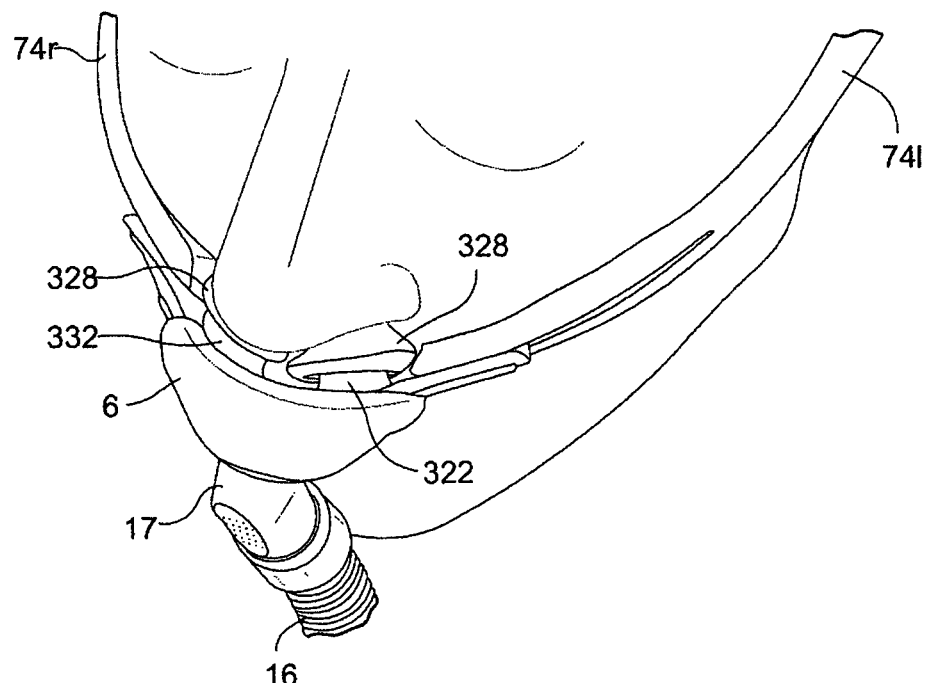

Referring to FIGS. 43a-43c, the flexible base 6 may also assist in forces, e.g. tube drag, applied in an up and down direction. As shown in FIGS. 43a, in a case where no external forces are applied, the nasal cushions 328 are in sealing engagement with the nares of the patient. As shown in FIG. 43b, if an upward force is applied to the patient interface structure, the flexible base 6 assists in decoupling the force so the nasal cushions 328 remain in sealing engagement. As shown in FIG. 43c, if a downward force is applied to the patient interface structure, the flexible base 6 assists in decoupling the force so that the nasal cushions 328 remain in sealing engagement with the nares. The stalks 332 may also compress, in the case of the upward force shown in FIG. 43b, or expand, in the case of the downward force shown in FIG. 43c, to assist in decoupling the force(s). It should also be appreciated that thinned regions, or trampolines, provided in the patient interface structure around the stalks and/or at the base of the frusto-conical sealing surface or zone may assist in decoupling the force(s).

Although FIGS. 42a-42c depict decoupling of force(s) in the left to right directions, and FIGS. 43a-43c depict decoupling of force(s) in the up and down directions, the flexible base may assist in decoupling forces in other directions, e.g. directions that are combinations of left to right, or up to down, or directions that are toward and away from the face of the patient.

As described above, the plenum of the base of the patient interface structure is semi-rigid, or flexible, so that the plenum will bend or flex when force, such as tube drag, is applied to the patient interface structure. The plenum is semi-rigid, or flexible, enough to maintain the venting of the patient interface structure, for example through a vent provided in an elbow connected to the patient interface structure. In other words, the plenum is semi-rigid, or flexible, enough to prevent the plenum from collapsing on itself and preventing venting of the patient interface structure.

Flexible Straps

As discussed above with respect to FIGS. 42a-43c, the straps, e.g. the flexible main straps 74r, 74l, may stretch to assist in decoupling force(s) applied to the patient interface structure, for example tube drag. The straps may also bend or flex to assist in decoupling force(s) applied to the patient interface structure. For example, the main strap(s) 74r, 74l may bend or flex, in and/or out of a plane defined by the strap(s) to assist in decoupling the force. As another example, the forked region of the strap(s) 74r, 74l defined by the connector 84 may bend, flex, and/or stretch in response to the applied force(s).

Although the various sample embodiments have been described in relation to a seal positioning and stabilizing structure generally including side straps, a top strap and a rear strap, and a main strap loop and a rear strap loop, it should be appreciated that other seal positioning and stabilizing structures may be used. For example, the seal positioning and stabilizing structure may include straps that are routed around and engage the ears of the patient. The seal positioning and stabilizing structure may comprise elastic and/or inelastic straps. The seal positioning and stabilizing structure may also be provided in various sizes. The seal positioning and stabilizing structure may be formed from silicone. For example, the seal positioning and stabilizing structure may be molded from silicone as one single piece. However, it should be appreciated that the seal positioning and stabilizing structure may be molded in several pieces, for example two, three or six pieces. Alternatively, silicones of varying durometer (i.e. hardness) may be co-molded. The silicone may also vary in width and depth (thickness) throughout the seal positioning and stabilizing structure, as shown for example in FIGS. 16a-16g, to strengthen the seal positioning and stabilizing structure in areas where force concentrations are higher, e.g. the cheek region. The straps may also have an anti-sweating feature. For example, the side of the straps configured to contact the patient's face may be textured to minimize or prevent sweating.

It should also be appreciated that the seal positioning and stabilizing structure and patient interface structure may be formed as one piece with interchangeable nasal pillows, for example as disclosed in Australian Application 2004308536, filed Dec. 24, 2004, the entire contents of which are incorporated herein by reference.

It should also be appreciated that the patient interface systems may comprise a nasal clip, instead of a seal positioning and stabilizing structure, to hold the patient interface structure in position on the patient's face.

The patient interface structures have been described above in relation to the illustrated sample embodiments as being formed of, for example, silicone. It should be appreciated that the patient interface structures may be formed of, for example, a foam material, such as disclosed in International Applications PCT/AU2007/001051, filed Jul. 30, 2007, and PCT/AU2007/001052, filed Jul. 27, 2007, and Australian Provisional Application 2007906102, filed Nov. 6, 2007, the entire contents of all three applications being incorporated herein by reference. It should also be appreciated that the patient interface structure may comprise a gel.

While various sample embodiments discussed above have been described with respect to nasal pillows or prongs, it should be appreciated that other forms of nozzles or nare seals maybe used, for example as disclosed in U.S. Pat. No. 4,782,832 (Trimble), U.S. Pat. No. 7,201,169 (Wilkie et al.), U.S. Pat. No. 7,059,328 (Wood), and WO 2000/074758 (Lovell).

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface system for delivery of a supply of air at positive pressure to the entrance of a patient's airways for treatment of sleep disordered breathing, comprising:
   a headgear assembly to provide a headgear tension force, said headgear assembly constructed and arranged to overlay a cheek region in use;
   an air delivery tube adapted to receive a supply of air at positive pressure;
   a pair of nasal pillows each having a frusto-cone shaped seal portion adapted to form a seal on an underside of a patient's nose in use in an area about a naris and a first decoupling assembly, said first decoupling assembly comprising a stalk, a first flexible region on the underside of the frusto-cone shaped seal portion and connected to said stalk and a second flexible region adjacent the base of the stalk; and
   a flexible base portion having a top portion to which said pair of nasal pillows is connected and having first and second lateral connectors, each of said lateral connectors being adapted to receive the headgear tension force from said headgear assembly, said flexible base portion having a lower portion opposite the top portion and adapted for interconnection with said air delivery tube, said lower portion forming a second decoupling assembly having a flexible portion configured to flex in response to forces applied thereto by the air delivery tube to decouple the forces from the pair of nasal pillows.

2. A patient interface system according to claim 1, wherein the flexible base lower portion comprises flexible bellows on lateral sides.

3. A patient interface system according to claim 1, further comprising a swivel or a ball and socket.

4. A patient interface system according to claim 3, further comprising a radial seal.

5. A patient interface system according to claim 1, wherein each of the stalks is adapted to articulate with respect to the corresponding frusto-cone shaped seal portion to assist in maintaining said seal portion in sealing engagement.

6. A patient interface system according to claim 5, wherein the nasal pillows are connected to the flexible base portion by thinned regions of the flexible base portion.

7. A patient interface system according to claim 1, wherein each nasal pillow is adapted to accommodate relative movement of the frusto-cone shaped seal portion and the flexible base portion.

8. A patient interface system according to claim 1, wherein the frusto-cone shaped seal portion of each of the pair of nasal pillows is adapted to rotate at an angle with respect to the stalk of the corresponding nasal pillow.

9. A patient interface system according to claim 1, wherein said headgear assembly comprises a third decoupling assembly wherein said headgear comprises a flexible strap and an end portion of said flexible strap adjacent said lateral connectors is constructed and arranged to stretch in response to a tube drag force.

10. A patient interface system according to claim 9, wherein the flexible strap comprises a flexible forked portion.

11. A patient interface system according to claim 1, wherein the tube comprises a retractable tube.

12. A patient interface system for delivery of a supply of air at positive pressure to the entrance of a patient's airways for treatment of sleep disordered breathing, comprising:
an air delivery tube adapted to receive a supply of air at positive pressure;
a patient interface comprising silicone and including:
a flexible base portion, the flexible base portion at least partially defining a plenum and having a lower portion, the lower portion including an aperture disposed on a first side of the plenum and in fluid communication with the air delivery tube, said lower portion forming a first decoupling assembly to decouple forces applied by the air delivery tube from the patient interface, the first decoupling assembly including a flexible portion configured to flex in response to the forces applied by the air delivery tube; and
a pair of nasal pillows, each nasal pillow having a neck portion and a frusto-conical seal portion connected to a first end portion of the neck portion and adapted to form a seal on an underside of a patient's nose in an area about the patient's naris, a second end portion of the neck portion being disposed on a second side of the plenum which is opposite the first side of the plenum;

a seal positioning and stabilizing structure connected to the patient interface, the seal positioning and stabilizing structure including:
a left strap and a right strap, each of the left and right straps having an end portion extending respectively from opposing sides of the patient interface so as to be provided on a respective side of the patient's face when the patient interface is worn, each of the left and right straps including a slot, wherein each of the left and right straps comprises silicone; and
a rear strap having end portions arranged to be provided, respectively, through the slots in the left and right straps such that the rear strap is configured to extend around a back of the patient's head when the patient interface is worn;
an elbow to connect the air delivery tube to the patient interface, the elbow including a vent to permit removal of exhaust gases; and
a swivel ring to connect the elbow to the patient interface, wherein the swivel ring permits the elbow to rotate with respect to the patient interface.

13. The patient interface system according to claim 12, wherein each nasal pillow includes a flexible region on an underside of the frusto-conical seal portion connecting the frusto-conical seal portion to the neck portion to decouple the forces applied by the air delivery tube from the frusto-conical seal portion.

14. The patient interface system according to claim 13, wherein each of the neck portions is adapted to articulate with respect to the corresponding frusto-conical seal portion to assist in maintaining said frusto-conical seal portion in sealing engagement.

15. The patient interface system according to claim 14, wherein each nasal pillow is adapted to accommodate relative movement of the frusto-conical seal portion and the flexible base portion.

16. The patient interface system according to claim 15, wherein the frusto-conical seal portion of each of the pair of nasal pillows is adapted to rotate at an angle with respect to the neck portion of the corresponding nasal pillow.

17. The patient interface system according to claim 16, further comprising a second decoupling structure adjacent a base of each said neck portion to decouple the forces applied by the air delivery tube from the neck portions.

18. The patient interface system according to claim 17, wherein the left and right straps are configured to stretch to assist in decoupling the forces applied by the air delivery tube from the patient interface.

19. The patient interface system according to claim 18, further comprising a pair of connectors respectively provided at the opposing sides of the patient interface, the pair of connectors configured to respectively connect the left and right straps to the patient interface.

20. A patient interface system for delivery of a supply of air at positive pressure to the entrance of a patient's airways for treatment of sleep disordered breathing, comprising:
an air delivery tube adapted to receive a supply of air at positive pressure;
a patient interface including:
a flexible base portion comprising silicone, the flexible base portion at least partially defining a plenum, the flexible base portion having a top portion and a lower portion opposite the top portion, the lower portion including an aperture formed therein and in fluid communication with the air delivery tube;
a pair of nasal pillows, each nasal pillow having a neck portion and a frusto-conical seal portion connected to a first end portion of the neck portion and adapted to form a seal on an underside of a patient's nose in an area about the patient's naris, a second end portion of the neck portion being disposed on the top portion of the flexible base portion; and a pair of connectors respectively provided at opposing sides of the patient interface;

a seal positioning and stabilizing structure connected to the patient interface, the seal positioning and stabilizing structure including:

a left strap and a right strap, each of the left and right straps having an end portion connected respectively to the pair of connectors so as to be provided on a respective side of the patient's face when the patient interface is worn, each of the left and right straps including a slot; and a rear strap having end portions arranged to be provided, respectively, through the slots in the left and right straps such that the rear strap is configured to extend around a back of the patient's head when the patient interface is worn;

an elbow to connect the air delivery tube to the patient interface, the elbow including a vent to permit removal of exhaust gases; and an elbow connector to connect the elbow to the patient interface, wherein the elbow connector permits the elbow to rotate with respect to the patient interface;

wherein the lower portion of the flexible base portion forms a first decoupling assembly to decouple forces applied by the air delivery tube from the patient interface, the first decoupling assembly including a flexible portion configured to flex in response to the forces applied by the air delivery tube.

21. The patient interface system according to claim 20, wherein the left and right straps are configured to pass respectively along a side of the patient's face between the patient's eye and ear.

22. The patient interface system according to claim 21, wherein each nasal pillow is adapted to accommodate relative movement of the frusto-conical seal portion and the flexible base portion.

23. The patient interface system according to claim 22, wherein the patient interface includes a frame connected to the flexible base portion, the pair of connectors being respectively provided at opposing sides of the frame.

24. The patient interface system according to claim 23, wherein the air delivery tube is configured to connect to the frame, the frame including an aperture formed therein which is in fluid communication with the air delivery tube.

25. The patient interface system according to claim 24, wherein the elbow connector is disposed on the frame and, along with the elbow, forms a ball and socket connection.

26. The patient interface system according to claim 25, wherein the flexible base portion includes a flange adjacent the aperture in the flexible base portion to connect to the frame such that the air delivery tube is configured to connect to a first side of the frame and the flexible base portion is configured to connect to a second side of the frame which is opposite the first side of the frame.

27. The patient interface system according to claim 26, wherein the patient interface includes a patient interface structure and the frame, the patient interface structure including the flexible base portion.

28. The patient interface system according to claim 27, wherein each of the neck portions is adapted to articulate with respect to the corresponding frusto-conical seal portion to assist in maintaining said frusto-conical seal portion in sealing engagement.

29. The patient interface system according to claim 28, wherein the frusto-conical seal portion of each of the pair of nasal pillows is adapted to rotate at an angle with respect to the neck portion of the corresponding nasal pillow.

30. The patient interface system according to claim 20, further comprising a second decoupling structure adjacent a base of each said neck portion to decouple the forces applied by the air delivery tube from the neck portions.

31. A patient interface system for delivery of a supply of air at positive pressure to the entrance of a patient's airways for treatment of sleep disordered breathing, comprising:

an air delivery tube adapted to receive a supply of air at positive pressure;

a patient interface structure comprising silicone and including:

a flexible base portion, the flexible base portion at least partially defining a plenum, the flexible base portion having a top portion and a lower portion opposite the top portion, the lower portion including an aperture formed therein and in fluid communication with the air delivery tube; and a pair of nasal pillows, each nasal pillow having a neck portion and a frusto-conical seal portion connected to a first end portion of the neck portion and adapted to form a seal on an underside of a patient's nose in an area about the patient's naris, a second end portion of the neck portion being disposed on the top portion of the flexible base portion;

a frame configured to connect to the air delivery tube and to the patient interface structure, the frame including:

a first aperture formed in a first side of the frame and configured to receive the air delivery tube, the first aperture being in fluid communication with the air delivery tube;

a second aperture formed in a second side of the frame which is opposite the first side of the frame; and a pair of connectors respectively provided at opposing sides of the frame, wherein the flexible base portion includes a flange adjacent the aperture in the flexible base portion to connect to the frame such that the air delivery tube is configured to connect to the first side of the frame and the flexible base portion is configured to connect to the second side of the frame;

a seal positioning and stabilizing structure connected to the patient interface, the seal positioning and stabilizing structure including:

a left strap and a right strap, each of the left and right straps having an end portion connected respectively to the pair of connectors so as to be provided on a respective side of the patient's face when the patient interface is worn, each of the left and right straps including a slot; and a rear strap having end portions arranged to be provided, respectively, through the slots in the left and right straps such that the rear strap is configured to extend around a back of the patient's head when the patient interface is worn, wherein the left and right straps are configured to pass respectively along the respective side of the patient's face between the patient's eye and ear;

an elbow to connect the air delivery tube to the frame, the elbow including a vent to permit removal of exhaust gases; and an elbow connector to connect the elbow to the frame, wherein the elbow connector is disposed on the frame and, along with the elbow, forms a ball and socket connection, wherein the lower portion of the flexible base portion forms a first decoupling assembly to decouple forces applied by the air delivery tube form the patient interface, the first decoupling assembly including a flexible portion configured to flex in response to the forces applied by the air delivery tube.

32. The patient interface system according to claim 31, wherein each nasal pillow is adapted to accommodate relative movement of the frusto-conical seal portion and the flexible base portion.

33. The patient interface system according to claim 32, wherein each of the neck portions is adapted to articulate with respect to the corresponding frusto-conical seal portion to assist in maintaining said frusto-conical seal portion in sealing engagement.

34. The patient interface system according to claim 33, wherein each nasal pillow includes a flexible region on an underside of the frusto-conical seal portion connecting the frusto-conical seal portion to the neck portion to decouple the forces applied by the air delivery tube from the frusto-conical seal portion.

35. The patient interface system according to claim 34, wherein the frusto-conical seal portion of each of the pair of nasal pillows is adapted to rotate at an angle with respect to the neck portion of the corresponding nasal pillow.

36. The patient interface system according to claim 35, wherein the frame is formed of a flexible material.

37. The patient interface system according to claim 31, further comprising a second decoupling structure adjacent a base of each said neck portion to decouple the forces applied by the air delivery tube from the neck portions.

38. A patient interface system for delivery of a supply of air at positive pressure to the entrance of a patient's airways for treatment of sleep disordered breathing, comprising:

a patient interface including:

a flexible base portion, the flexible base portion at least partially defining a plenum and having a lower portion including an aperture disposed on a first side of the plenum for receiving a supply of air, said lower portion forming a first decoupling assembly to decouple external forces from the patient interface, the first decoupling assembly including a flexible portion configured to flex in response to the forces applied by the air delivery tube; and a pair of nasal pillows configured to deliver the supply of air to the patient's airways, each nasal pillow having a neck portion and a seal portion connected to a first end portion of the neck portion and adapted to form a seal on an underside of a patient's nose in an area about the patient's naris, a second end portion of the neck portion being disposed on a second side of the plenum which is opposite the first side of the plenum.

39. The patient interface system according to claim 38, further comprising an air delivery tube adapted to deliver the supply of air to the patient interface, wherein the external forces are applied by the air delivery tube.

40. The patient interface system according to claim 39, wherein the flexible base portion comprises silicone.

41. The patient interface system according to claim 40, further comprising a seal positioning and stabilizing structure connected to the patient interface, the seal positioning and stabilizing structure including:

a left strap and a right strap, each of the left and right straps having an end portion extending respectively from opposing sides of the patient interface so as to be provided on a respective side of the patient's face when the patient interface is worn, each of the left and right straps including a slot; and a rear strap having end portions arranged to be provided, respectively, through the slots in the left and right straps such that the rear strap is configured to extend around a back of the patient's head when the patient interface is worn.

42. The patient interface system according to claim 41, further comprising an elbow to connect the air delivery tube to the patient interface, the elbow including a vent to permit removal of exhaust gases.

43. The patient interface system according to claim 42, further comprising an elbow connector to connect the elbow to the patient interface, wherein the elbow connector permits the elbow to rotate with respect to the patient interface.

44. The patient interface system according to claim 43, wherein the seal portion of each nasal pillow has a frusto-conical shape.

45. The patient interface system according to claim 44, wherein the elbow connector is a swivel ring.

46. The patient interface system according to claim 45, wherein each of the left and right straps comprises silicone.

47. The patient interface system according to claim 46, wherein each nasal pillow includes a flexible region on an underside of the frusto-conical seal portion connecting the frusto-conical seal portion to the neck portion to decouple the forces applied by the air delivery tube from the frusto-conical seal portion.

48. The patient interface system according to claim 47, wherein each of the neck portions is adapted to articulate with respect to the corresponding frusto-conical seal portion to assist in maintaining said frusto-conical seal portion in sealing engagement.

49. The patient interface system according to claim 48, wherein each nasal pillow is adapted to accommodate relative movement of the frusto-conical seal portion and the flexible base portion.

50. The patient interface system according to claim 49, wherein the frusto-conical seal portion of each of the pair of nasal pillows is adapted to rotate at an angle with respect to the neck portion of the corresponding nasal pillow.

51. The patient interface system according to claim 50, further comprising a second decoupling structure adjacent a base of each said neck portion to decouple the forces applied by the air delivery tube from the neck portions.

52. The patient interface system according to claim 51, wherein the left and right straps are configured to stretch to assist in decoupling the forces applied by the air delivery tube from the patient interface.

53. The patient interface system according to claim 52, further comprising a pair of connectors respectively provided at the opposing sides of the patient interface, the pair of connectors configured to respectively connect the left and right straps to the patient interface.

54. The patient interface system according to claim 44, wherein the patient interface includes a pair of connectors respectively provided at the opposing sides of the patient interface, the pair of connectors configured to respectively connect to the left and right straps.

55. The patient interface system according to claim 54, wherein the left and right straps are configured to pass respectively along the respective side of the patient's face between the patient's eye and ear.

56. The patient interface system according to claim 55, wherein the patient interface includes a frame connected to the flexible base portion, the pair of connectors being respectively provided at opposing sides of the frame.

57. The patient interface system according to claim 56, wherein the patient interface includes a patient interface structure and the frame, the patient interface structure including the flexible base portion.

58. The patient interface system according to claim 57, wherein each of the neck portions is adapted to articulate with respect to the corresponding frusto-conical seal portion to assist in maintaining said frusto-conical seal portion in sealing engagement.

59. The patient interface system according to claim 58, wherein each nasal pillow is adapted to accommodate relative movement of the frusto-conical seal portion and the flexible base portion.

60. The patient interface system according to claim 59, wherein each nasal pillow includes a flexible region on an underside of the frusto-conical seal portion connecting the frusto-conical seal portion to the neck portion to decouple the forces applied by the air delivery tube from the frusto-conical seal portion.

61. The patient interface system according to claim 60, wherein the frusto-conical seal portion of each of the pair of nasal pillows is adapted to rotate at an angle with respect to the neck portion of the corresponding nasal pillow.

62. The patient interface system according to claim 61, further comprising a second decoupling structure adjacent a base of each said neck portion to decouple the forces applied by the air delivery tube from the neck portions.

63. The patient interface system according to claim 62, wherein the lower portion of the flexible base portion is interconnected with the air delivery tube via the frame.

64. The patient interface system according to claim 63, wherein the elbow connector is disposed on the frame and, along with the elbow, forms a ball and socket connection.

* * * * *